United States Patent
Maynard et al.

(10) Patent No.: US 6,673,811 B1
(45) Date of Patent: Jan. 6, 2004

(54) 1H-PYRROLO [3,2-B] PYRIDINE-3-CARBOXYLIC ACID AMINES AS GABA$_A$ RECEPTOR LIGANDS

(75) Inventors: George D. Maynard, Clinton, CT (US); Manuka Ghosh, Branford, CT (US); Christopher J. O'Donnell, Mystic, CT (US)

(73) Assignees: Neurogen Corporation, Branford, CT (US); Pfizer, Inc., New York, NY (US)

( * ) Notice: Subject to any disclaimer, the term of this patent is extended or adjusted under 35 U.S.C. 154(b) by 0 days.

(21) Appl. No.: 10/299,199

(22) Filed: Nov. 19, 2002

Related U.S. Application Data

(60) Provisional application No. 60/333,027, filed on Nov. 19, 2001.

(51) Int. Cl.[7] .................... A61K 31/4965; A61K 31/44; C07D 241/02
(52) U.S. Cl. .................. 514/300; 514/255.02; 544/405; 546/113
(58) Field of Search ............................ 514/255.02, 300; 544/405; 546/113

(56) References Cited

U.S. PATENT DOCUMENTS

| | | | | | |
|---|---|---|---|---|---|
| 5,750,702 A | * | 5/1998 | Albaugh et al. | ............. | 546/183 |
| 5,925,770 A | * | 7/1999 | Albaugh et al. | ............. | 548/452 |
| 6,096,887 A | * | 8/2000 | Albaugh et al. | ............. | 544/127 |

\* cited by examiner

*Primary Examiner*—D. Margaret Seaman
(74) *Attorney, Agent, or Firm*—McDonnell Boehnen Hulbert & Berghoff

(57) ABSTRACT

Disclosed are 1H-Pyrrolo[3,2-b]pyridine-3-carboxylic acid amides that bind to the benzodiazepine site of GABA$_A$ receptors. Such compounds can be used to modulate ligand binding to GABA$_A$ receptors in vivo and in vitro, and are particularly useful in the treatment of a variety of central nervous system (CNS) disorders in humans, domesticated companion animals, and livestock animals.

58 Claims, No Drawings

1H-PYRROLO [3,2-B] PYRIDINE-3-CARBOXYLIC ACID AMINES AS GABA$_A$ RECEPTOR LIGANDS

BACKGROUND OF THE INVENTION

This application claims priority from U.S. Provisional Application Ser. No. 60/333,027, filed Nov. 19, 2001, the disclosure of which is hereby incorporated by reference in its entirety.

FIELD OF THE INVENTION

This invention relates to 1H-Pyrrolo[3,2-b]pyridine-3-carboxylic acid amides that bind to the benzodiazepine site of GABA$_A$ receptors. This invention also relates to pharmaceutical compositions comprising such compounds and to the use of such compounds in the treatment of central nervous system (CNS) diseases.

DESCRIPTION OF THE RELATED ART

The GABA$_A$ receptor superfamily represents one of the classes of receptors through which the major inhibitory neurotransmitter, γ-aminobutyric acid, or GABA, acts. Widely, although unequally, distributed throughout the mammalian brain, GABA mediates many of its actions through a complex of proteins called the GABA$_A$ receptor, which causes alteration in chloride conductance and membrane polarization. In addition to being the site of neurotransmitter action, a number of drugs including the anxiolytic and sedating benzodiazepines bind to this receptor. The GABA$_A$ receptor comprises a chloride channel that generally, but not invariably, opens in response to GABA, allowing chloride to enter the cell. This, in turn, effects a slowing of neuronal activity through hyperpolarization of the cell membrane potential.

GABA$_A$ receptors are composed of five protein subunits. A number of cDNAs for these GABA$_A$ receptor subunits have been cloned and their primary structures determined. While these subunits share a basic motif of 4 membrane-spanning helices, there is sufficient sequence diversity to classify them into several groups. To date at least 6α, 3β, 3γ, 1ε, 1δ and 2ρ subunits have been identified. Native GABA$_A$ receptors are typically composed of 2α, 2β, and 1γ. Various lines of evidence (such as message distribution, genome localization and biochemical study results) suggest that the major naturally occurring receptor combinations are $α_1β_2γ_2$, $α_2β_2γ_2$, $α_3β_3γ_2$, and $α_5β_3γ_2$ (Mohler et al. *Neuroch. Res.* 1995; 20(5):631–36).

The GABA$_A$ receptor binding sites for GABA (2 per receptor complex) are formed by amino acids from the α and β subunits. Amino acids from the α and γ subunits together form one benzodiazepine site per receptor. Benzodiazepines exert their pharmacological actions by interacting with the benzodiazepine binding sites associated with the GABA$_A$ receptor. In addition to the benzodiazepine site (sometimes referred to as the benzodiazepine or BDZ receptor), the GABA$_A$ receptor contains sites of interaction for several other classes of drugs. These include a steroid binding site, a picrotoxin site, and a barbiturate site. The benzodiazepine site of the GABA$_A$ receptor is a distinct site on the receptor complex that does not overlap with the site of interaction for other classes of drugs that bind to the receptor or for GABA (see, e.g., Cooper, et al., The Biochemical Basis of Neuropharmacology, 6$^{th}$ ed., 1991, pp. 145–148, Oxford University Press, New York).

In a classic allosteric mechanism, the binding of a drug to the benzodiazepine site increases the affinity of the GABA receptor for GABA. Benzodiazepines and related drugs that enhance the ability of GABA to open GABA$_A$ receptor channels are known as agonists or partial agonists depending on the level of GABA enhancement. Other classes of drugs, such as β-carboline derivatives, that occupy the same site and negatively modulate the action of GABA are called inverse agonists. A third class of compounds exists which occupy the same site as both the agonists and inverse agonists and yet have little or no effect on GABA activity. These compounds will, however, block the action of agonists or inverse agonists and are thus referred to as GABA$_A$ receptor antagonists.

The important allosteric modulatory effects of drugs acting at the benzodiazepine site were recognized early, and the distribution of activities at different subtype receptors has been an area of intense pharmacological discovery. Agonists that act at the benzodiazepine site are known to exhibit anxiolytic, sedative, and hypnotic effects, while compounds that act as inverse agonists at this site elicit anxiogenic, cognition enhancing, and proconvulsant effects. While benzodiazepines have enjoyed long pharmaceutical use as anxiolytics, these compounds are known to exhibit a number of unwanted side effects. These may include cognitive impairment, sedation, ataxia, potentiation of ethanol effects, and a tendency for tolerance and drug dependence.

GABA$_A$ selective ligands may also act to potentiate the effects of certain other CNS active compounds. For example, there is evidence that selective serotonin reuptake inhibitors (SSRIs) may show greater antidepressant activity when used in combination with GABA$_A$ selective ligands than when used alone.

SUMMARY OF THE INVENTION

This invention provides 1H-pyrrolo[3,2-b]pyridine-3-carboxylic acid amides that bind preferably with high affinity and high selectivity to the benzodiazepine site of GABA$_A$ receptors, including human GABA$_A$ receptors. Compounds of the invention preferably bind with high selectivity and/or high affinity to GABA$_A$ receptors and thereby act as agonists, antagonists or inverse agonists of such receptors. As such, they are useful in the treatment of various CNS disorders.

The invention provides compounds of Formula I (shown below), and pharmaceutical compositions comprising compounds of Formula I.

The invention further provides methods of treating patients suffering from certain CNS disorders with an effective amount of a compound of the invention. The patient may be a human or other mammal. Treatment of humans, domesticated companion animals (pets) or livestock animals suffering from certain CNS disorders with an effective amount of a compound of the invention is encompassed by the invention.

In a separate aspect, the invention provides a method of potentiating the actions of other CNS active compounds. This method comprises administering an effective amount of a compound of the invention in conjunction with the administration of another CNS active compound.

Additionally this invention relates to the use of compounds of Formula I as probes for the localization of GABA$_A$ receptors in tissue sections.

In a first aspect the invention provides compounds and pharmaceutically acceptable salts of Formula I

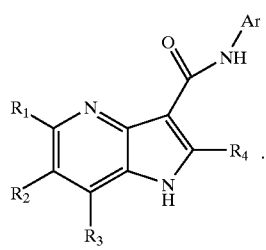

The invention includes 3 classes of compounds of Formula I, these classes of compounds will be referred to as Class 1, Class 2, and Class 3.

The substituents $R_1$, $R_2$, and $R_3$ carry the same definitions for all three classes of compounds 1, 2, and 3. Thus, for each of classes 1, 2, and 3, $R_1$, $R_2$, and $R_3$ independently represent:

A) hydrogen, halogen, halo($C_1$–$C_6$)alkyl, hydroxy, cyano, amino, alkyl, alkoxy, mono($C_1$–$C_6$)alkylamino, di-($C_1$–$C_6$)alkylamino, mono($C_1$–$C_6$)alkylamino($C_1$–$C_6$)alkyl, di-($C_1$–$C_6$)alkylamino($C_1$–$C_6$)alkyl, —C(=O)NR$_{10}$R$_{11}$, —C(=O)OR$_{10}$, and —OC(=O)R$_{10}$, —C(=O)R$_{10}$, where $R_{10}$ or $R_{11}$ are independently hydrogen, $C_1$–$C_6$ alkyl, phenyl, phenyl($C_1$–$C_6$)alkyl, pyridyl, or pyridyl($C_1$–$C_6$)alkyl; or B) haloalkoxy, alkenyl, alkynyl, hydroxyalkyl, —DR$_{20}$, —E—R$_{35}$, —$C_1$–$C_4$alkyl-DR$_{20}$, —$C_1$–$C_4$alkyl-O—R$_{20}$, —E—R$_{20}$—G—R$_{30}$, —E—L, —E—R$_{20}$—L, J, —C(=O)—L, or —$C_1$–$C_4$alkyl-J;
where
D represents —S(O)$_n$—, —S(O)$_n$NH—, —S(O)$_n$NH$_2$, —S(O)$_n$NR$_{30}$—, —NHC(=O)—, —NHC(=O)H, —NR$_{30}$C(=O)—, —NR$_{30}$C(=O)H, —NHS(O)$_n$—, or —NR$_{30}$S(O)$_n$—;
E and G are independently NH, N—$C_1$–$C_6$alkyl, S, and O;
each $R_{20}$ and $R_{30}$ is independently a ($C_1$–$C_8$)straight, ($C_1$–$C_8$)branched, ($C_3$–$C_8$)cyclic alkyl or ($C_3$–$C_8$) cycloalkyl($C_1$–$C_6$)alkyl group, where each alkyl and cycloalkyl group contains zero or one or more double or triple bonds and where each carbon atom in the $R_{20}$ and $R_{30}$ groups is optionally substituted with one or more subsitutents independently selected from group C), where group C) consists of oxo, hydroxy, halogen, cyano, amino, $C_1$–$C_6$alkoxy, —NH($C_1$–$C_6$alkyl), —N($C_1$–$C_6$alkyl)($C_1$–$C_6$alkyl), —NHC(=O)($C_1$–$C_6$alkyl), —N($C_1$–$C_6$alkyl)C(=O)($C_1$–$C_6$alkyl), —NHS(O)$_n$($C_1$–$C_6$alkyl), —S(O)$_n$($C_1$–$C_6$alkyl), —S(O)$_n$NH($C_1$–$C_6$alkyl), —S(O)$_n$N($C_1$–$C_6$alkyl)($C_1$–$C_6$alkyl), or L, where n is 0, 1, or 2;
each $R_{35}$ is independently a ($C_1$–$C_8$)straight, ($C_1$–$C_8$) branched, ($C_3$–$C_8$)cyclic alkyl or ($C_3$–$C_8$)cycloalkyl ($C_1$–$C_6$)alkyl group, where each alkyl and cycloalkyl group contains zero or one or more double or triple bonds and where each carbon atom in $R_{35}$ is substituted with one or more substituents independently selected from group C);
J and L are independently selected at each occurrence from saturated, partially unsaturated, and aromatic rings having from 4 to 7 ring atoms, where 0, 1, or 2 of the ring atoms are oxygen or nitrogen, and the remaining ring atoms are carbon atoms, where the rings are unsubstituted or substituted with one or more substituents which are independently i) halogen, oxo, hydroxy, amino, cyano, $C_1$–$C_6$alkyl, $C_1$–$C_6$alkoxy, $C_1$–$C_6$alkoxy($C_1$–$C_6$alkyl), $C_1$–$C_6$haloalkyl, $C_1$–$C_6$haloalkoxy, or mono- or di-($C_1$–$C_6$)alkylamino; or ii) phenyl, pyridyl, pyrimidyl, or pyrazinyl, each of which is unsubstituted or substituted with from 1 to 3 of halogen, hydroxy, amino, cyano, $C_1$–$C_4$alkyl, $C_1$–$C_4$alkoxy, $C_1$–$C_2$haloalkyl, $C_1$–$C_2$haloalkoxy, and mono- or di-($C_1$–$C_4$) alkylamino; or $R_4$ is hydrogen, halogen, or hydroxyl.

For compounds of Class 1, at least 1 of $R_1$, $R_2$, and $R_3$ is selected from B) and J is not phenyl or pyridyl.

The variable "Ar" is defined differently for each of Classes 1, 2, and 3.

For compounds and salts of Class 1:

Ar represents an aryl, arylalkyl, heteroarylalkyl or heteroaryl group, each aryl or heteroaryl having 1 or 2 aromatic rings and 4 to 7 ring atoms in each aromatic ring, where 0, 1, or 2 of the ring atoms chosen are oxygen, nitrogen, or sulfur and the remaining ring atoms are carbon atoms and where each ring is optionally substituted with 1 or more of $R_{40}$, where $R_{40}$ is independently selected at each occurrence from hydroxy, halogen, cyano, nitro, amino, XR$_{50}$, $C_1$–$C_4$alkyl-XR$_{50}$, and Y;

X is independently selected at each occurrence from the group consisting of a bond, —CH$_2$—, —CHR$_{60}$—, —O—, —C(=O)—, —C(=O)O—, —OC(=O)—, —S(O)$_n$—, —NH—, —NR$_{60}$—, —C(=O)NH—, —C(=O)NR$_{60}$—, —S(O)$_n$NH—, —S(O)$_n$NR$_{60}$—, —NHC(=O)—, —NR$_{60}$C(=O)—, —NHS(O)$_n$—, and —NR$_{60}$S(O)$_n$—; where n is 0, 1, or 2;

$R_{50}$ and $R_{60}$ are independently selected at each occurrence from hydrogen, $C_1$–$C_8$ alkyl, $C_3$–$C_8$cycloalkyl, and ($C_3$–$C_8$) cycloalkyl($C_1$–$C_6$)alkyl, where each alkyl and cycloalkyl contains zero or one or more double or triple bonds, and where each carbon atom of the alkyl, cycloalkyl or cycloalkylalkyl is optionally independently substituted with one or more of oxo, hydroxy, halogen, cyano, amino, $C_1$–$C_6$alkoxy, —NH($C_1$–$C_6$alkyl), —N($C_1$–$C_6$alkyl)($C_1$–$C_6$alkyl), —NHC(=O)($C_1$–$C_6$alkyl), —N($C_1$–$C_6$alkyl)C(=O)($C_1$–$C_6$alkyl), —NHS(O)$_n$($C_1$–$C_6$alkyl), —S(O)$_n$($C_1$–$C_6$alkyl), —S(O)$_n$NH($C_1$–$C_6$alkyl), —S(O)$_n$N($C_1$–$C_6$alkyl)($C_1$–$C_6$alkyl), and Z, where n is 0, 1, or 2; and Y and Z are independently selected at each occurrence from saturated, partially unsaturated, and aromatic rings having from 4 to 7 ring atoms in each aromatic ring, where 0, 1, or 2 ring atoms are oxygen or nitrogen and the remaining ring atoms are carbon, and wherein Y and Z are independently unsubstituted or substituted with one or more of halogen, oxo, hydroxy, amino, cyano, $C_1$–$C_6$alkyl, $C_1$–$C_6$alkoxy, $C_1$–$C_6$alkoxy($C_1$–$C_6$alkyl), $C_1$–$C_6$haloalkyl, $C_1$–$C_6$haloalkoxy, or mono- or di-($C_1$–$C_6$) alkylamino.

For compounds and salts of Class 2:

Ar represents heteroaryl or heteroaryl($C_1$–$C_6$)alkyl, where the heteroaryl is selected from quinolinyl, benzothienyl, indolyl, pryidazinyl, pyazinyl, isoindolyl, isoquinolyl, quinazolinyl, quinoxalinyl, phthalazinyl, imidazolyl, isoxazolyl, pyrazolyl, oxazolyl, thienyl, thiazolyl, indolizinyl, indazolyl, benzothiazolyl, benzimidazolyl, benzofuranyl, benzoisoxolyl, dihydrobenzodioxinyl, furanyl, pyrrolyl, oxadiazolyl, thiadiazolyl, triazolyl, tetrazolyl, oxazolopyridinyl, imidazopyridinyl, isothiazolyl, naphthyridinyl, cinnolinyl, carbazolyl, beta-carbolinyl, isochromanyl, chromanonyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, phenoxazinyl, phenothiazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromanyl, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, and benzothiopyranyl S,S-dioxide, wherein Ar is optionally substituted by 1 or more of $R_{40}$.

Each $R_{40}$ for the compounds of Class 2 is independently hydroxy, halogen, cyano, nitro, amino, $XR_{50}$, $C_1$–$C_4$alkyl-$XR_{50}$, or Y;

where each X is independently a bond, —$CH_2$—, —$CHR_{60}$—, —O—, —C(=O)—, —C(=O)O—, —OC(=O)—, —S(O)$_n$—, —NH—, —$NR_{60}$—, —C(=O)NH—, —C(=O)$NR_{60}$—, —S(O)$_n$NH—, —S(O)$_n$$NR_{60}$—, —NHC(=O)—, —$NR_{60}$C(=O)—, —NHS(O)$_n$—, and —$NR_{60}$S(O)$_n$—, where n is 0, 1, or 2;

$R_{50}$ and $R_{60}$ are independently selected at each occurrence from hydrogen, $C_1$–$C_8$ alkyl, $C_3$–$C_8$cycloalkyl, and ($C_3$–$C_8$)cycloalkyl($C_1$–$C_6$)alkyl, where each alkyl and cycloalkyl contains zero or one or more double or triple bonds, and where each carbon atom of the alkyl, cycloalkyl or cycloalkylalkyl is optionally independently substituted with one or more of oxo, hydroxy, halogen, cyano, amino, $C_1$–$C_6$alkoxy, —NH($C_1$–$C_6$alkyl), —N($C_1$–$C_6$alkyl)($C_1$–$C_6$alkyl), —NHC(=O)($C_1$–$C_6$alkyl), —N($C_1$–$C_6$alkyl)C(=O)($C_1$–$C_6$alkyl), —NHS(O)$_n$($C_1$–$C_6$alkyl), —S(O)$_n$($C_1$–$C_6$alkyl), —S(O)$_n$NH($C_1$–$C_6$alkyl), —S(O)$_n$N($C_1$–$C_6$alkyl)($C_1$–$C_6$alkyl), and Z, where n is 0, 1, or 2; and Y and Z are independently selected at each occurrence from saturated, partially unsaturated, and aromatic rings having from 4 to 7 ring atoms in each aromatic ring, where 0, 1, or 2 ring atoms are oxygen or nitrogen and the remaining ring atoms are carbon, and wherein Y and Z are independently unsubstituted or substituted with one or more of halogen, oxo, hydroxy, amino, cyano, $C_1$–C6alkyl, $C_1$–$C_6$alkoxy, $C_1$–$C_6$alkoxy($C_1$–$C_6$alkyl), $C_1$–$C_6$haloalkyl, $C_1$–$C_6$haloalkoxy, or mono- or di-($C_1$–$C_6$)alkylamino.

For compounds and salts of Class 3:

Ar represents phenyl, pyridyl, or pyrimidinyl each of which is optionally substituted with 1 or more of $R_{40}$; where each $R_{40}$ is independently hydroxy, halogen, cyano, nitro, amino, $C_1$–$C_6$alkyl, $C_1$–$C_6$alkoxy, $C_1$–$C_6$alkanoyl, $C_3$–$C_7$cycloalkyl, $C_3$–$C_7$cycloalkyl($C_1$–$C_4$)alkyl, $C_3$–$C_7$cycloalkyl-O—, $C_3$–$C_7$cycloalkyl($C_1$–$C_4$)alkoxy-, $C_2$–$C_6$alkenyl, $C_1$–$C_6$alkylthio-, halo($C_1$–$C_6$)alkyl, or halo($C_1$–$C_6$)alkoxy.

In addition, Ar in the compounds and salts of Class 3 must is substituted by at least one of —E—$R_{50}$—G—$R_{60}$, —E—$R_{50}$—G—Y, $C_1$–$C_4$alkyl-$XR_{50}$, —NH—$R_{60}$—Y, —($NR_{50}$)$R_{60}$—Y, or Y;

where X is independently selected at each occurrence from the group consisting of —O—, —C(=O)—, —C(=O)O—, —OC(=O)—, —S(O)$_n$—, —NH—, —$NR_{60}$—, —C(=O)NH—, —C(=O)$NR_{60}$—, —S(O)$_n$NH—, —S(O)$_n$$NR_{60}$—, —NHC(=O)—, —$NR_{60}$C(=O)—, —NHS(O)$_n$—, and —$NR_{60}$S(O)$_n$—, where n is 0, 1, or 2;

$R_{50}$ and $R_{60}$ are independently selected at each occurrence from hydrogen, $C_1$–$C_8$ alkyl, $C_3$–$C_8$cycloalkyl, and ($C_3$–$C_8$)cycloalkyl($C_1$–$C_6$)alkyl, where each alkyl and cycloalkyl contains zero or one or more double or triple bonds, and where each carbon atom of the alkyl, cycloalkyl or cycloalkylalkyl is optionally independently substituted with one or more of oxo, hydroxy, halogen, cyano, amino, $C_1$–$C_6$alkoxy, —NH($C_1$–$C_6$alkyl), —N($C_1$–$C_6$alkyl)($C_1$–$C_6$alkyl), —NHC(=O)($C_1$–$C_6$alkyl), —N($C_1$–$C_6$alkyl)C(=O)($C_1$–$C_6$alkyl), —NHS(O)$_n$($C_1$–$C_6$alkyl), —S(O)$_n$($C_1$–$C_6$alkyl), —S(O)$_n$NH($C_1$–$C_6$alkyl), —S(O)$_n$N($C_1$–$C_6$alkyl)($C_1$–$C_6$alkyl), and Z, where n is 0, 1, or 2; and Y and Z are independently selected at each occurrence from saturated, partially unsaturated, and aromatic rings having from 4 to 7 ring atoms in each aromatic ring, where 0, 1, or 2 ring atoms are oxygen or nitrogen and the remaining ring atoms are carbon, and wherein Y and Z are independently unsubstituted or substituted with one or more of halogen, oxo, hydroxy, amino, cyano, $C_1$–$C_6$alkyl, $C_1$–$C_6$alkoxy, $C_1$–$C_6$alkoxy($C_1$–$C_6$alkyl), $C_1$–$C_6$haloalkyl, $C_1$–$C_6$haloalkoxy, or mono- or di-($C_1$–$C_6$)alkylamino.

DETAILED DESCRIPTION OF THE INVENTION

Specific embodiments of the invention include compounds and pharmaceutically acceptable salts, Classes 1, 2, and 3, in which $R_4$ is hydrogen.

Additionally, the invention is directed to Class 1 compounds and salts of Formula I wherein Ar represents an aryl, arylalkyl, heteroaryl, or heteroarylalkyl group, the aryl or heteroaryl of which is selected from phenyl, pyridyl, pyrimidinyl, pyrazinyl, pyrrolyl, imidazolyl, thienyl, thiazolyl, isothiazolyl, oxazolyl [1,3,4]thiadiazolyl, triazolyl, indolyl, quionolinyl, isoquinolinyl benzodioxolyl, benzofuranyl, benzimiazolyl, benzoisoxolyl, and dihydrobenzodioxinyl, and is optionally substituted by one or more of $R_{40}$, and $R_{40}$ is as defined above. Such compounds are hereinafter referred to as compounds of Class 1A.

The invention also includes compounds and pharmaceutically acceptable salts of Formula I, Class 1, wherein $R_1$ is selected from B).

In this aspect, $R_2$ and $R_3$ are independently selected from hydrogen, halogen, $C_1$–$C_6$haloalkyl, $C_1$–$C_6$haloalkoxy, hydroxy, cyano, amino, $C_1$–$C_6$alkyl, $C_1$–$C_6$alkoxy, and mono- or di-($C_1$–$C_6$)alkylamino; more preferably $R_2$ and $R_3$ are independently selected from hydrogen, halogen, $CF_3$, $CHF_2$, —$OCF_3$, hydroxy, cyano, $C_1$–$C_2$alkyl, $C_1$–$C_2$alkoxy, and mono- or di-($C_1$–$C_2$)alkylamino, or $R_2$ and $R_3$ may be independently selected from hydrogen, halogen, methyl and ethyl.

In this aspect, $R_4$ is preferably hydrogen; and Ar is as defined for compounds of Class 1A.

Further included in the invention are compounds and pharmaceutically acceptable salts of Formula I, Class 1A. Compounds and salts of Formula I, Class 1A are those where:

$R_1$ is selected from B);

$R_2$ and $R_3$ are independently selected from hydrogen, halogen, methyl and ethyl;

$R_4$ is preferably hydrogen; and $R_{40}$ is independently selected at each occurrence from $C_1$–$C_6$alkyl, $C_1$–$C_6$alkoxy; halogen, mono or di-($C_1$–$C_6$)alkylamino, mono or di-($C_1$–$C_6$)alkylamino ($C_1$–$C_6$)alkoxy, ($C_1$–$C_6$)alkoxy($C_1$–$C_6$)alkyl, and ($C_1$–$C_6$)alkoxy($C_1$–$C_6$)alkoxy.

The invention is directed to another embodiment that includes compounds and pharmaceutically acceptable salts of Formula I, Class 1A, in which:

$R_1$ is selected from B); and B) in this embodiment is —E—$R_{35}$, —$C_1$–$C_4$alkyl-O—$R_{20}$, —E—$R_{20}$—G—$R_{30}$, —E—L, —E—$R_{20}$—L, J, or —$C_1$–$C_4$alkyl-J; and E and G in this embodiment are independently NH, N—$C_1$–$C_6$alkyl, or O.

In this embodiment, $R_{20}$, $R_{30}$, and $R_{35}$ of the invention are independently selected at each occurrence from: straight, branched, and cyclic alkyl groups, and (cycloalkyl)alkyl groups, said straight, branched, and cyclic alkyl groups, and (cycloalkyl)alkyl groups consisting of 1 to 8 carbon atoms, and containing zero or one or more double or triple bonds, wherein in $R_{20}$ and $R_{35}$ each of which 1 to 8 carbon atoms may be further substituted with one or more substituent(s) independently selected from group C) and in $R_{35}$ at least one of which 1 to 8 carbon atoms is further substituted by one or more substituent(s) independently selected from group C) wherein group C) consists of: oxo, hydroxy, halogen, cyano, amino, $C_1$–$C_6$alkoxy, —NH($C_1$–$C_6$alkyl), —N($C_1$–$C_6$alkyl)($C_1$–$C_6$alkyl), —NHC(=O)($C_1$–$C_6$alkyl), —N($C_1$–$C_6$alkyl)C(=O)($C_1$–$C_6$alkyl), —NHS(O)$_n$($C_1$–$C_6$alkyl), —S(O)$_n$($C_1$–$C_6$alkyl), —S(O)$_n$NH($C_1$–$C_6$alkyl), —S(O)$_n$N($C_1$–$C_6$alkyl)($C_1$–$C_6$alkyl), and L.

J and L are independently selected at each occurrence from: saturated heterocyclic rings having from 4 to 7 ring atoms, wherein 1 or 2 ring atoms are nitrogen, with remaining ring atoms being carbon, which rings are unsubstituted or substituted with one or more substituents independently selected from halogen, oxo, hydroxy, amino, cyano, $C_1$–$C_6$alkyl, $C_1$–$C_6$alkoxy, $C_1$–$C_6$alkoxy($C_1$–$C_6$alkyl), $C_1$–$C_6$haloalkyl, $C_1$–$C_6$haloalkoxy, and mono- or di-($C_1$–$C_6$)alkylamino; with the proviso that J is not unsubstituted or substituted phenyl or unsubstituted or substituted pyridyl.

$R_2$ and $R_3$ in this embodiment are independently selected from hydrogen, halogen, $C_1$–$C_6$haloalkyl, $C_1$–$C_6$haloalkoxy, hydroxy, cyano, amino, $C_1$–$C_6$alkyl, $C_1$–$C_6$alkoxy, and mono- or di-($C_1$–$C_6$)alkylamino; more preferably $R_2$ and $R_3$ are independently selected from hydrogen, halogen, $CF_3$, $CHF_2$, —$OCF_3$, hydroxy, cyano, $C_1$–$C_2$alkyl, $C_1$–$C_2$alkoxy, and mono- or di-($C_1$–$C_2$)alkylamino, or $R_2$ and $R_3$ may be independently selected from hydrogen, halogen, methyl and ethyl;

$R_4$ is preferably hydrogen; and $R_{40}$ is independently selected at each occurrence from $C_1$–$C_6$alkyl, $C_1$–$C_6$alkoxy; halogen, mono or di-($C_1$–$C_6$)alkylamino, mono or di-($C_1$–$C_6$)alkylamino ($C_1$–$C_6$)alkoxy, ($C_1$–$C_6$)alkoxy($C_1$–$C_6$)alkyl, and ($C_1$–$C_6$)alkoxy($C_1$–$C_6$)alkoxy.

The invention further includes compounds and pharmaceutically acceptable salts of Formula I, Class 1 wherein Ar carries the definition set forth for compounds and salts of Class 1A and $R_{40}$ is independently selected at each occurrence from hydroxy, halogen, cyano, amino, $XR_{50}$, —($C_1$–$C_4$)alkyl-$XR_{50}$, and Y;

X is independently selected at each occurrence from the group consisting of a bond, —$CH_2$—, —$CHR_{60}$—, —O—, —C(=O)—, —S(O)$_n$—, —NH—, and —$NR_{60}$—, where n is 0, 1, or 2;

$R_{50}$ and $R_{60}$ are independently selected at each occurrence from hydrogen, and straight, branched, and cyclic alkyl groups, and (cycloalkyl)alkyl groups, said straight, branched, and cyclic alkyl groups, and (cycloalkyl)alkyl groups consisting of 1 to 8 carbon atoms, and containing zero or one or more double or triple bonds, each of which 1 to 8 carbon atoms may be further substituted with one or more substituent(s) independently selected from oxo, hydroxy, halogen, cyano, amino, $C_1$–$C_6$alkoxy, —NH($C_1$–$C_6$alkyl), —N($C_1$–$C_6$alkyl)($C_1$–$C_6$alkyl), —NHC(=O)($C_1$–$C_6$alkyl), —N($C_1$–$C_6$alkyl)C(=O)($C_1$–$C_6$alkyl), —NHS(O)$_n$($C_1$–$C_6$alkyl), —S(O)$_n$($C_1$–$C_6$alkyl), —S(O)$_n$NH($C_1$–$C_6$alkyl), —S(O)$_n$N($C_1$–$C_6$alkyl)($C_1$–$C_6$alkyl), and Z, where n is 0, 1, or 2; and Y and Z are independently selected at each occurrence from: saturated, partially unsaturated, or aromatic rings having from 4 to 7 ring atoms, 0, 1, or 2 ring atoms chosen from oxygen and nitrogen, with remaining ring atoms being carbon, wherein Y and Z are unsubstituted or substituted with one or more substituents independently selected from halogen, oxo, hydroxy, amino, cyano, $C_1$–$C_6$alkyl, $C_1$–$C_6$alkoxy, $C_1$–$C_6$alkoxy ($C_1$–$C_6$alkyl), $C_1$–$C_6$haloalkyl, $C_1$–$C_6$haloalkoxy, and mono- or di-($C_1$–$C_6$)alkylamino. Such compounds will be referred to as compounds of Class 1B.

Additional embodiments of the invention are directed to compounds and pharmaceutically acceptable salts of Class 1B in which $R_1$ is selected from B);

$R_2$ and $R_3$ are independently selected from hydrogen, halogen, methyl and ethyl; and $R_4$ is preferably hydrogen.

In another embodiment, the invention is directed to compounds and pharmaceutically acceptably salts of Formula I, Class 2. In this embodiment, Ar represents an aryl, arylalkyl, heteroaryl, or heteroarylalkyl group, the aryl or heteroaryl of which is selected from piperazinyl, pyrrolyl, imidazolyl, thienyl, thiazolyl, isothiazolyl, oxazolyl [1,3,4]thiadiazolyl, triazolyl, indolyl, quionolinyl, isoquinolinyl benzodioxolyl, benzofuranyl, benzimiazolyl, benzoisoxolyl, and dihydrobenzodioxinyl, and is optionally substituted by one or more of $R_{40}$, wherein $R_{40}$ carries the definition set forth above for compounds of Class 2. Such compounds will be referred to as compounds of Class 2A.

The invention is also directed to compounds and pharmaceutically acceptable salts of Formula I, Class 2A wherein $R_1$ is selected from hydrogen, halogen, $C_1$–$C_6$haloalkyl, $C_1$–$C_6$haloalkoxy, hydroxy, cyano, amino, $C_1$–$C_6$alkyl, $C_1$–$C_6$alkoxy, mono- or di-($C_1$–$C_6$)alkylamino and B).

$R_2$ and $R_3$ in this embodiment are independently selected from hydrogen, halogen, $C_1$–$C_6$haloalkyl, $C_1$–$C_6$haloalkoxy, hydroxy, cyano, amino, $C_1$–$C_6$alkyl, $C_1$–$C_6$alkoxy, and mono- or di-($C_1$–$C_6$)alkylamino, or more preferably $R_2$ and $R_3$ are independently selected from hydrogen, halogen, $CF_3$, $CHF_2$, —$OCF_3$, hydroxy, cyano, $C_1$–$C_2$alkyl, $C_1$–$C_2$alkoxy, and mono- or di-($C_1$–$C_2$)alkylamino, or $R_2$ and $R_3$ are independently selected from hydrogen, halogen, methyl and ethyl.

In the compounds of Formula I, Class 2A, $R_4$ is preferably hydrogen.

Another embodiment of the invention is directed to compounds and pharmaceutically acceptable salts of Formula I, Class 2A in which $R_1$ is selected from hydrogen, halogen, $C_1$–$C_6$haloalkyl, $C_1$–$C_6$haloalkoxy, hydroxy, cyano, amino, $C_1$–$C_6$alkyl, $C_1$–$C_6$alkoxy, mono- or di-($C_1$–$C_6$)alkylamino and B), and B) is —E—$R_{35}$, —$C_1$–$C_4$alkyl-O—$R_{20}$, —E—$R_{20}$—G—$R_{30}$, —E—L, —E—$R_{20}$—L, J, or —$C_1$–$C_4$alkyl-J.

E and G are independently NH, N—$C_1$–$C_6$alkyl, or O;

$R_2$ and $R_3$ are independently selected from hydrogen, halogen, methyl and ethyl; and $R_4$ is hydrogen.

Another embodiment of the invention is directed to compounds and pharmaceutically acceptable salts of Formula I, Class 2A in which Ar, which is defined as for compounds of Class 2A, is optionally substituted by one or more of $R_{40}$.

$R_{40}$ in this embodiment is independently selected at each occurrence from $C_1$–$C_6$alkyl, $C_1$–$C_6$alkoxy; halogen, mono or di-($C_1$–$C_6$)alkylamino, mono or di-($C_1$–$C_6$)alkylamino ($C_1$–$C_6$)alkoxy, ($C_1$–$C_6$)alkoxy($C_1$–$C_6$)alkyl, and ($C_1$–$C_6$)alkoxy($C_1$–$C_6$)alkoxy.

In this embodiment, $R_1$ in this embodiment is selected from hydrogen, halogen, $C_1$–$C_6$haloalkyl, $C_1$–$C_6$haloalkoxy, hydroxy, cyano, amino, $C_1$–$C_6$alkyl, $C_1$–$C_6$alkoxy, mono- or di-($C_1$–$C_6$)alkylamino and B).

$R_2$ and $R_3$ in this embodiment are independently selected from hydrogen, halogen, $C_1$–$C_6$haloalkyl, $C_1$–$C_6$haloalkoxy, hydroxy, cyano, amino, $C_1$–$C_6$alkyl, $C_1$–$C_6$alkoxy, and mono- or di-($C_1$–$C_6$)alkylamino, or more preferably $R_2$ and $R_3$ are independently selected from hydrogen, halogen, $CF_3$, $CHF_2$, —$OCF_3$, hydroxy, cyano, $C_1$–$C_2$alkyl, $C_1$–$C_2$alkoxy, and mono- or di-($C_1$–$C_2$)alkylamino, or $R_2$ and $R_3$ are independently selected from hydrogen, halogen, methyl and ethyl.

$R_4$ in this embodiment is hydrogen.

Another embodiment of the invention includes compounds and pharmaceutically acceptable salts of Formula I, Class 2A, in which Ar, which is defined as for compounds of Class 2A, is optionally substituted by one or more of $R_{40}$. $R_{40}$ for this embodiment is independently selected at each occurrence from $C_1$–$C_6$alkyl, $C_1$–$C_6$alkoxy; halogen, mono or di-($C_1$–$C_6$)alkylamino, mono or di-($C_1$–$C_6$)alkylamino ($C_1$–$C_6$)alkoxy, ($C_1$–$C_6$)alkoxy($C_1$–$C_6$)alkyl, and ($C_1$–$C_6$)alkoxy($C_1$–$C_6$)alkoxy.

$R_1$ is selected from hydrogen, halogen, $C_1$–$C_6$haloalkyl, $C_1$–$C_6$haloalkoxy, hydroxy, cyano, amino, $C_1$–$C_6$alkyl, $C_1$–$C_6$alkoxy, mono- or di-($C_1$–$C_6$)alkylamino and B).

B) in this embodiment is —$R_{35}$, —$C_1$–$C_4$alkyl-O—$R_{20}$, —E—$R_{20}$—G—$R_{30}$, —E—L, —E—$R_{20}$—L, J, or —$C_1$–$C_4$alkyl-J, where E and G are independently NH, N—$C_1$–$C_6$alkyl, or O.

$R_{20}$, $R_{30}$, and $R_{35}$ in this embodiment are independently selected at each occurrence from straight, branched, and cyclic alkyl groups, and (cycloalkyl)alkyl groups, said straight, branched, and cyclic alkyl groups, and (cycloalkyl) alkyl groups consisting of 1 to 8 carbon atoms, and containing zero or one or more double or triple bonds, wherein in $R_{20}$ and $R_{35}$ each of which 1 to 8 carbon atoms may be further substituted with one or more substituent(s) independently selected from group C) and in $R_{35}$ at least one of which 1 to 8 carbon atoms is further substituted by one or more substituent(s) independently selected from group C) wherein group C) consists of: oxo, hydroxy, halogen, cyano, amino, $C_1$–$C_6$alkoxy, —NH($C_1$–$C_6$alkyl), —N($C_1$–$C_6$alkyl)($C_1$–$C_6$alkyl), —NHC(=O)($C_1$–$C_6$alkyl), —N($C_1$–$C_6$alkyl)C(=O)($C_1$–$C_6$alkyl), —NHS(O)$_n$($C_1$–$C_6$alkyl), —S(O)$_n$($C_1$–$C_6$alkyl), —S(O)$_n$NH($C_1$–$C_6$alkyl), —S(O)$_n$N($C_1$–$C_6$alkyl)($C_1$–$C_6$alkyl), and L.

J and L in this embodiment are independently selected at each occurrence from: saturated heterocyclic rings having from 4 to 7 ring atoms, wherein 1 or 2 ring atoms are nitrogen, with remaining ring atoms being carbon, which rings are unsubstituted or substituted with one or more substituents independently selected from halogen, oxo, hydroxy, amino, cyano, $C_1$–$C_6$alkyl, $C_1$–$C_6$alkoxy, $C_1$–$C_6$alkoxy($C_1$–$C_6$alkyl), $C_1$–$C_6$haloalkyl, $C_1$–$C_6$haloalkoxy, and mono- or di-($C_1$–$C_6$)alkylamino; with the proviso that J is not phenyl or pyridyl;

$R_2$ and $R_3$ in this embodiment are independently selected from hydrogen, halogen, $C_1$–$C_6$haloalkyl, $C_1$–$C_6$haloalkoxy, hydroxy, cyano, amino, $C_1$–$C_6$alkyl, $C_1$–$C_6$alkoxy, and mono- or di-($C_1$–$C_6$)alkylamino, or more preferably $R_2$ and $R_3$ are independently selected from hydrogen, halogen, $CF_3$, $CHF_2$, —$OCF_3$, hydroxy, cyano, $C_1$–$C_2$alkyl, $C_1$–$C_2$alkoxy, and mono- or di-($C_1$–$C_2$)alkylamino, or $R_2$ and $R_3$ are independently selected from hydrogen, halogen, methyl and ethyl.

$R_4$ in this embodiment is preferably hydrogen.

The invention also includes compounds and pharmaceutically acceptable salts of Formula I, where Ar is as defined for compounds of Class 2A.

$R_{40}$ in this embodiment is independently selected at each occurrence from hydroxy, halogen, cyano, amino, $XR_{50}$, —($C_1$–$C_4$)alkyl-$XR_{50}$, and Y.

X in this embodiment is independently selected at each occurrence from the group consisting of a bond, —$CH_2$—, —$CHR_{60}$—, —O—, —C(=O)—, —S(O)$_n$—, —NH—, and —$NR_{60}$—, where n is 0, 1, or 2.

$R_{50}$ and $R_{60}$ in this embodiment are independently selected at each occurrence from hydrogen, and straight, branched, and cyclic alkyl groups, and (cycloalkyl)alkyl groups, said straight, branched, and cyclic alkyl groups, and (cycloalkyl)alkyl groups consisting of 1 to 8 carbon atoms, and containing zero or one or more double or triple bonds, each of which 1 to 8 carbon atoms may be further substituted with one or more substituent(s) independently selected from oxo, hydroxy, halogen, cyano, amino, $C_1$–$C_6$alkoxy, —NH($C_1$–$C_6$alkyl), —N($C_1$–$C_6$alkyl)($C_1$–$C_6$alkyl), —NHC(=O)($C_1$–$C_6$alkyl), —N($C_1$–$C_6$alkyl)C(=O)($C_1$–$C_6$alkyl), —NHS(O)$_n$($C_1$–$C_6$alkyl), —S(O)$_n$($C_1$–$C_6$alkyl), —S(O)$_n$NH($C_1$–$C_6$alkyl), —S(O)$_n$N($C_1$–$C_6$alkyl)($C_1$–$C_6$alkyl), and Z, where n is 0, 1, or 2.

Y and Z in this embodiment are independently selected at each occurrence from: saturated, partially unsaturated, or aromatic rings having from 4 to 7 ring atoms, 0, 1, or 2 ring atoms chosen from oxygen and nitrogen, with remaining ring atoms being carbon, wherein Y and Z are unsubstituted or substituted with one or more substituents independently selected from halogen, oxo, hydroxy, amino, cyano, $C_1$–$C_6$alkyl, $C_1$–$C_6$alkoxy, $C_1$–$C_6$alkoxy($C_1$–$C_6$alkyl), $C_1$–$C_6$haloalkyl, $C_1$–$C_6$haloalkoxy, and mono- or di-($C_1$–$C_6$)alkylamino. Such compounds will be referred to as compounds of Class 2B.

Other compounds and salts of Formula I, Class 2B included in the invention are those wherein $R_1$ is selected from hydrogen, halogen, $C_1$–$C_6$haloalkyl, $C_1$–$C_6$haloalkoxy, hydroxy, cyano, amino, $C_1$–$C_6$alkyl, $C_1$–$C_6$alkoxy, mono- or di-($C_1$–$C_6$)alkylamino and B);

$R_2$ and $R_3$ are independently selected from hydrogen, halogen, methyl and ethyl; and $R_4$ is hydrogen.

The invention is directed to compounds and pharmaceutically acceptable salts of Formula I, Class 3, in which $R_1$ is selected from hydrogen, halogen, $C_1$–$C_6$haloalkyl, $C_1$–$C_6$haloalkoxy, hydroxy, cyano, amino, $C_1$–$C_6$alkyl, $C_1$–$C_6$alkoxy, and mono- or di-($C_1$–$C_6$)alkylamino and B).

In this embodiment, $R_2$ and $R_3$ are independently selected from hydrogen, halogen, $C_1$–$C_6$haloalkyl, $C_1$–$C_6$haloalkoxy, hydroxy, cyano, amino, $C_1$–$C_6$alkyl, $C_1$–$C_6$alkoxy, and mono- or di-($C_1$–$C_6$)alkylamino or preferably $R_2$ and $R_3$ are independently selected from hydrogen, halogen, $CF_3$, $CHF_2$, —$OCF_3$, hydroxy, cyano, $C_1$–$C_2$alkyl, $C_1$–$C_2$alkoxy, and mono- or di-($C_1$–$C_2$)alkylamino; and $R_4$ is preferably hydrogen.

Other compounds of Formula I, Class 3 are those wherein Ar, which is phenyl, pyridyl, or pyrimidinyl, each of which is optionally substituted by 1 or more of $R_{40}$, where $R_{40}$ is preferably selected independently at each occurrence from hydroxy, halogen, cyano, amino, $C_1$–$C_6$alkyl, $C_1$–$C_6$alkoxy, halo($C_1$–$C_6$)alkyl, and halo($C_1$–$C_6$)alkoxy.

Ar in this embodiment is also substituted by at least one of —E—$R_{50}$—G—$R_{60}$—, —E—$R_{50}$—G—Y, $C_1$–$C_4$alkyl-X$R_{50}$, —NH—$R_{60}$—Y, —(N$R_{50}$)$R_{60}$—Y, and Y, where X is independently selected at each occurrence from the group consisting of —O—, —C(=O)—, —C(=O)O—, —OC(=O)—, —S(O)$_n$—, —NH—, —N$R_{60}$—, —C(=O)NH—, —C(=O)N$R_{60}$—, —NHC(=O)—, and —N$R_{60}$C(=O);

$R_{50}$ and $R_{60}$ are independently selected at each occurrence from hydrogen, and straight, branched, and cyclic alkyl groups, and (cycloalkyl)alkyl groups, said straight, branched, and cyclic alkyl groups, and (cycloalkyl)alkyl groups consisting of 1 to 8 carbon atoms, and containing zero or one or more double or triple bonds, each of which 1 to 8 carbon atoms may be further substituted with one or more substituent(s) independently selected from oxo, hydroxy, halogen, cyano, amino, $C_1$–$C_6$alkoxy, —NH($C_1$–$C_6$alkyl), —N($C_1$–$C_6$alkyl)($C_1$–$C_6$alkyl), —NHC(=O)($C_1$–$C_6$alkyl), —N($C_1$–$C_6$alkyl)C(=O)($C_1$–$C_6$alkyl), and Z.

$R_2$ and $R_3$ in preferred embodiments of the invention are independently selected from hydrogen, halogen, $C_1$–$C_6$haloalkyl, $C_1$–$C_6$haloalkoxy, hydroxy, cyano, amino, $C_1$–$C_6$alkyl, $C_1$–$C_6$alkoxy, and mono- or di-($C_1$–$C_6$)alkylamino or preferably $R_2$ and $R_3$ are independently selected from hydrogen, halogen, $CF_3$, $CHF_2$, —$OCF_3$, hydroxy, cyano, $C_1$–$C_2$alkyl, $C_1$–$C_2$alkoxy, and mono- or di-($C_1$–$C_2$)alkylamino, or from hydrogen, halogen, methyl and ethyl.

In this embodiment, $R_4$ is preferably hydrogen.

Other preferred compounds of Formula I include those where $R_1$ is amino($C_1$–$C_6$)alkoxy, mono($C_1$–$C_3$)alkylamino($C_1$–$C_6$)alkoxy, di($C_1$–$C_3$)alkylamino($C_1$–$C_6$)alkoxy, pyridyl($C_1$–$C_6$)alkoxy, hydroxy($C_1$–$C_6$)alkoxy, ($C_1$–$C_4$)alkoxy($C_1$–$C_6$)alkoxy, piperazinyl($C_1$–$C_6$)alkoxy wherein the piperazinyl group is optionally substituted with ($C_1$–$C_6$)alkyl, morpholinyl($C_1$–$C_6$)alkoxy, or thiomorpholinyl($C_1$–$C_6$)alkoxy;

$R_2$ and $R_3$ are independently selected from H, ($C_1$–$C_6$)alkyl, halogen or ($C_1$–$C_6$)alkoxy.

Within this preferred aspect, other preferred compounds of Formula I are those where both $R_2$ and $R_3$ are both hydrogen.

More preferred compounds of Formula I include those where $R_1$ is amino($C_1$–$C_4$)alkoxy, mono($C_1$–$C_4$)alkylamino($C_1$–$C_4$)alkoxy, di($C_1$–$C_4$)alkylamino($C_1$–$C_4$)alkoxy, pyridyl($C_1$–$C_4$)alkoxy, hydroxy($C_1$–$C_4$)alkoxy, piperazinyl($C_1$–$C_4$)alkoxy wherein the piperazinyl group is optionally substituted with ($C_1$–$C_4$)alkyl, or morpholinyl($C_1$–$C_6$)alkoxy.

Within this preferred aspect, other preferred compounds of Formula I are those where both $R_2$ and $R_3$ are both hydrogen.

Still more preferred compounds of Formula I include those where $R_2$ and $R_3$ are independently selected from H, ($C_1$–$C_4$)alkyl, halogen or ($C_1$–$C_4$)alkoxy, provided that at least one of $R_2$ and $R_3$ is H.

Other more preferred compounds of Formula I include those where $R_1$ is amino($C_1$–$C_4$)alkoxy, mono($C_1$–$C_4$)alkylamino($C_1$–$C_4$)alkoxy, di($C_1$–$C_4$)alkylamino($C_1$–$C_4$)alkoxy, pyridyl($C_1$–$C_4$)alkoxy, hydroxy($C_1$–$C_4$)alkoxy, piperazinyl($C_1$–$C_4$)alkoxy wherein the piperazinyl group is optionally substituted with ($C_1$–$C_4$)alkyl, or morpholinyl($C_1$–$C_6$)alkoxy;

$R_2$ and $R_3$ are independently selected from H, ($C_1$–$C_4$)alkyl, or ($C_1$–$C_4$)alkoxy, provided that at least one of $R_2$ and $R_3$ is H.

Within this preferred aspect, other preferred compounds of Formula I are those where both $R_2$ and $R_3$ are both hydrogen.

Yet other preferred compounds of Formula I include those where $R_1$ is amino($C_1$–$C_4$)alkoxy, mono($C_1$–$C_4$)alkylamino($C_1$–$C_4$)alkoxy, di($C_1$–$C_4$)alkylamino($C_1$–$C_4$)alkoxy, pyridyl($C_1$–$C_4$)alkoxy, hydroxy($C_1$–$C_4$)alkoxy, piperazinyl($C_1$–$C_4$)alkoxy wherein the piperazinyl group is optionally substituted with ($C_1$–$C_4$)alkyl, or morpholinyl($C_1$–$C_4$)alkoxy;

$R_2$ and $R_3$ are independently selected from H, and ($C_1$–$C_4$)alkyl, provided that at least one of $R_2$ and $R_3$ is H.

Within this preferred aspect, other preferred compounds of Formula I are those where both $R_2$ and $R_3$ are both hydrogen.

Even other preferred compounds of Formula I include those where $R_1$ is amino($C_2$–$C_4$)alkoxy, mono($C_1$–$C_4$)alkylamino($C_2$–$C_4$)alkoxy, di($C_1$–$C_4$)alkylamino($C_2$–$C_4$)alkoxy, pyridyl($C_2$–$C_4$)alkoxy, hydroxy($C_2$–$C_4$)alkoxy, piperazinyl($C_2$–$C_4$)alkoxy wherein the piperazinyl group is optionally substituted with ($C_1$–$C_4$)alkyl, or morpholinyl($C_2$–$C_4$)alkoxy;

$R_2$ is H or methyl; and $R_3$ is H.

Within this preferred aspect, other preferred compounds of Formula I are those where both $R_2$ and $R_3$ are both hydrogen.

Representative compounds of the present invention, which are encompassed by Formula I, include, but are not limited to the compounds set forth in Examples 1, 2, and 3 and their pharmaceutically acceptable acid and base addition salts. If the compound of the invention is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds.

Non-toxic pharmaceutical salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, HOOC-(CH$_2$)n-ACOOH where n is 0–4, and the like. Those skilled in the art will recognize a wide variety of non-toxic pharmaceutically acceptable addition salts.

The invention also includes hydrates of compounds of Formula I.

The invention includes all crystalline forms of the compounds of Formula I. Certain crystalline forms may be preferred.

The present invention also encompasses the acylated prodrugs of the compounds of Formula I. Those skilled in the art will recognize various synthetic methodologies that may be employed to prepare non-toxic pharmaceutically acceptable addition salts and acylated prodrugs of the compounds encompassed by Formula I. The invention further encompasses all enantiomers and diastereomers of the disclosed compounds. Those of ordinary skill in the art will readily recognize methods by which mixtures of enantiomers and diasteromers may be resolved. The definition of Formula I as used in herein include possible isomers, such as tautomers and rotamers.

This invention relates to 1H-pyrrolo[3,2-b]pyridine-3-carboxylic acid amides, preferred examples of which bind with high affinity to the benzodiazepine site of GABA$_A$ receptors, including human GABA$_A$ receptors. Preferred 1H-pyrrolo[3,2-b]pyridine-3-carboxylic acid amides, that bind with high selectivity to the benzodiazepine site of GABA$_A$ receptors, including human GABA$_A$ receptors, are also included in this invention. Without wishing to be bound to any particular theory, it is believed that the interaction of the compounds of Formula I with the benzodiazepine site results in the pharmaceutical utility of these compounds.

The invention further comprises methods of treating patients in need of such treatment with an amount of a compound of the invention sufficient to alter the symptoms of a CNS disorder. Compounds of the inventions that act as agonists at $\alpha_2\beta_3\gamma_2$ and $\alpha_3\ominus_3\gamma_2$ receptor subtypes are useful in treating anxiety disorders such as panic disorder, obsessive compulsive disorder and generalized anxiety disorder; stress disorders including post-traumatic stress, and acute stress disorders. Compounds of the inventions that act as agonists at $\alpha_2\beta_3\gamma_2$ and $\alpha_3\beta_3\beta_2$ receptor subtypes are also useful in treating depressive or bipolar disorders and in treating sleep disorders. Compounds of the invention that act as inverse agonists at the $\alpha_5\beta_3\gamma_2$ receptor subtype or $\alpha_1\beta_2\gamma_2$ and $\alpha_5\beta_3\gamma_2$ receptor subtypes are useful in treating cognitive disorders including those resulting from Down Syndrome, neurodegenerative diseases such as Alzheimer's disease and Parkinson's disease, and stroke related dementia. Compounds of the invention that act as inverse agonists at the $\alpha_5\beta_3\gamma_2$ are particularly useful in treating cognitive disorders through the enhancement of memory, and particularly short-term memory, in memory-impaired patients. Compounds of the invention that act as agonists at the $\alpha_1\beta_2\gamma_2$ receptor subtype are useful in treating convulsive disorders such as epilepsy. Compounds that act as antagonists at the benzodiazepine site are useful in reversing the effect of benzodiazepine overdose and in treating drug and alcohol addiction.

The diseases and/or disorders that can also be treated using compounds and compositions according to the invention include:

Depression, e.g. depression, atypical depression, bipolar disorder, depressed phase of bipolar disorder.

Anxiety, e.g. general anxiety disorder (GAD), agoraphobia, panic disorder +/− agoraphobia, social phobia, specific phobia, Post traumatic stress disorder, obsessive compulsive disorder (OCD), dysthymia, adjustment disorders with disturbance of mood and anxiety, separation anxiety disorder, anticipatory anxiety acute stress disorder, adjustment disorders, cyclothymia.

Sleep disorders, e.g. sleep disorders including primary insomnia, circadian rhythm sleep disorder, dyssomnia NOS, parasomnias, including nightmare disorder, sleep terror disorder, sleep disorders secondary to depression and/or anxiety or other mental disorders, substance induced sleep disorder.

Cognition Impairment, e.g. cognition impairment, memory impairment, short-term memory impairment, Alzheimer's disease, Parkinson's disease, mild cognitive impairment (MCI), age-related cognitive decline (ARCD), stroke, traumatic brain injury, AIDS associated dementia, and dementia associated with depression, anxiety or psychosis.

Attention Deficit Disorder, e.g. attention deficit disorder (ADD), and attention deficit and hyperactivity disorder (ADHD). Speech disorders, e.g. stuttering, including motor tic, clonic stuttering, dysfluency, speech blockage, dysarthria, Tourete syndrome or logospasm.

The invention also provides pharmaceutical compositions comprising one or more compounds of the invention together with a pharmaceutically acceptable carrier or excipient, for treating disorders responsive to GABA$_A$ receptor modulation, e.g., treatment of anxiety, depression, sleep disorders or cognitive impairment by GABA$_A$ receptor modulation. Pharmaceutical compositions include packaged pharmaceutical compositions comprising a container holding a therapeutically effective amount of at least one GABA$_A$ receptor modulator as described supra and instructions (e.g., labeling) indicating the contained GABA$_A$ receptor ligand is to be used for treating a disorder responsive to GABA$_A$ receptor modulation in the patient.

In a separate aspect, the invention provides a method of potentiating the actions of other CNS active compounds, which comprises administering an effective amount of a compound of the invention in combination with another CNS active compound. Such CNS active compounds include, but are not limited to the following: for anxiety, serotonin receptor (e.g. 5-HT$_{1A}$) agonists and antagonists; for anxiety and depression, neurokinin receptor antagonists or corticotropin releasing factor receptor (CRF$_1$) antagonists; for sleep disorders, melatonin receptor agonists; and for neurodegenerative disorders, such as Alzheimer's dementia, nicotinic agonists, muscarinic agents, acetylcholinesterase inhibitors and dopamine receptor agonists. Particularly the invention provides a method of potentiating the antidepressant activity of selective serotonin reuptake inhibitors (SSRIs) by administering an effective amount of a GABA agonist compound of the invention in combination with an SSRI.

Combination administration can be carried out in a fashion analogous to that disclosed in Da-Rocha, et al., *J. Psychopharmacology* (1997) 11(3) 211–218; Smith, et al., *Am. J. Psychiatry* (1998) 155(10) 1339–45; or Le, et al., *Alcohol and Alcoholism* (1996) 31 Suppl. 127–132. Also see, the discussion of the use of the GABA$_A$ receptor ligand 3-(5-methylisoxazol-3-yl)-6-(1-methyl-1,2,3-triazol-4-yl) methyloxy-1,2,4-triazolo [3,4-a]phthalzine in combination with nicotinic agonists, muscarinic agonists, and acetylcholinesterase inhibitors, in PCT International publications Nos.

WO 99/47142, WO 99/47171, and WO 99/47131, respectively. Also see in this regard PCT International publication No. WO 99/37303 for its discussion of the use of a class of GABA$_A$ receptor ligands, 1,2,4-triazolo[4,3-b]pyridazines, in combination with SSRIs.

The present invention also pertains to methods of inhibiting the binding of benzodiazepine compounds, such as Ro15-1788, or GABA to the GABA$_A$ receptors which methods involve contacting a solution containing compound of the invention with cells expressing GABA$_A$ receptors, wherein the compound is present at a concentration sufficient to inhibit benzodiazepine binding or GABA binding to GABA$_A$ receptors in vitro. This method includes inhibiting the binding of benzodiazepine compounds to GABA$_A$ receptors in vivo, e.g., in a patient given an amount of a compound of Formula I that would be sufficient to inhibit the binding of benzodiazepine compounds or GABA to GABA$_A$ receptors in vitro. In one embodiment, such methods are useful in treating benzodiazepine drug overdose. The amount of a compound that would be sufficient to inhibit the binding of a benzodiazepine compound to the GABA$_A$ receptor may be readily determined via a GABA$_A$ receptor binding assay, such as the assay described in Example 6. The GABA$_A$ receptors used to determine in vitro binding may be obtained from a variety of sources, for example from preparations of rat cortex or from cells expressing cloned human GABA$_A$ receptors.

The present invention also pertains to methods for altering the signal-transducing activity, particularly the chloride ion conductance of GABA$_A$ receptors, said method comprising exposing cells expressing such receptors to an effective amount of a compound of the invention. This method includes altering the signal-transducing activity of GABA$_A$ receptors in vivo, e.g., in a patient given an amount of a compound of Formula I that would be sufficient to alter the signal-transducing activity of GABA$_A$ receptors in vitro. The amount of a compound that would be sufficient to alter the signal-transducing activity of GABA$_A$ receptors may be determined via a GABA$_A$ receptor signal transduction assay, such as the assay described in Example 7. The cells expressing the GABA receptors in vivo may be, but are not limited to, neuronal cells or brain cells. Such cells may be contacted with compounds of the invention through contact with a body fluid containing the compound, for example through contact with cerebrospinal fluid. Alteration of the signal-transducing activity of GABA$_A$ receptors in vitro may be determined from a detectable change in the electrophysiology of cells expressing GABA$_A$ receptors, when such cells are contacted with a compound of the invention in the presence of GABA.

Intracellular recording or patch-clamp recording may be used to quantitate changes in electrophysiology of cells. A reproducible change in behavior of an animal given a compound of the invention may also be used to indicate that changes in the electrophysiology of the animal's cells expressing GABA$_A$ receptors has occurred.

The GABA$_A$ receptor ligands provided by this invention and labeled derivatives thereof are also useful as standards and reagents in determining the ability of a potential pharmaceutical to bind to the GABA$_A$ receptor. Radiolabeled derivatives the GABA$_A$ receptor ligands provided by this invention are also useful as radiotracers for positron emission tomography (PET) imaging or for single photon emission computerized tomography (SPECT).

More particularly compounds of the invention may be used for demonstrating the presence of GABA$_A$ receptors in cell or tissue) samples. This may be done by preparing a plurality of matched cell or tissue samples, at least one of which is prepared as an experiment sample and at least one of which is prepared as a control sample. The experimental sample is prepared by contacting (under conditions that permit binding of RO15-1788 to GABA$_A$ receptors within cell and tissue samples) at least one of the matched cell or tissue samples that has not previously been contacted with any compound or salt of the invention with an experimental solution comprising the detectably-labeled preparation of the selected compound or salt at the first measured molar concentration. The control sample is prepared by in the same manner as the experimental sample and also contains an unlabelled preparation of the same compound or salt of the invention at a greater molar concentration.

The experimental and control samples are then washed to remove unbound detectably-labeled compound. The amount of remaining bound detectably-labeled compound is then measured and the amount of detectably-labeled compound in the experimental and control samples is compared. A comparison that indicates the detection of a greater amount of detectable label in the at least one washed experimental sample than is detected in any of control samples demonstrates the presence of GABA$_A$ receptors in that experimental sample.

The detectably-labeled compound used in this procedure may be labeled with a radioactive label or a directly or indirectly luminescent label. When tissue sections are used in this procedure and the detectably-labeled compound is radiolabeled, the bound, labeled compound may be detected autoradiographically to generate an autoradiogram. The amount of detectable label in an experimental or control sample may be measured by viewing the autoradiograms and comparing the exposure density of the autoradiograms.

Chemical Description And Terminology

The compounds herein described may have one or more asymmetric centers or planes. Compounds of the present invention containing an asymmetrically substituted atom may be isolated in optically active or racemic forms. It is well known in the art how to prepare optically active forms, such as by resolution of racemic forms (racemates), by asymmetric synthesis, or by synthesis from optically active starting materials. Resolution of the racemates can be accomplished, for example, by conventional methods such as crystallization in the presence of a resolving agent, or chromatography, using, for example a chiral HPLC column. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral (enantiomeric and diastereomeric), and racemic forms, as well as all geometric isomeric forms of a structure are intended, unless the specific stereochemistry or isomeric form is specifically indicated.

When any variable occurs more than one time in any constituent or formula for a compound, its definition at each occurrence is independent of its definition at every other occurrence. Thus, for example, if a group is shown to be substituted with 0 to 3 R*, (where R* indicates any variable group such as Ar, R$_1$, R$_2$, R$_3$ etc.) then said group may optionally be substituted with up to three R* groups and R* at each occurrence is selected independently from the definition of R*. Also, combinations of substituents and/or variables are permissible only if such combinations result in stable compounds.

A dash "–" that is not between two letters or symbols is used to indicate a point of attachement for a substituent. For example "—NH—R$_{60}$—Y" is attached through the nitrogen atom.

As used herein, "alkyl" is intended to include both branched and straight-chain aliphatic hydrocarbon groups, having the specified number of carbon atoms. Alkyl groups of 2 or more carbon atoms may contain double or triple bonds. Examples of alkyl include, but are not limited to, methyl, ethyl, n-propyl, i-propyl, n-butyl, s-butyl, t-butyl, n-pentyl, and s-pentyl. Preferred alkyl groups are $C_1$–$C_6$ alkyl groups. "$C_1$–$C_6$ alkyl" indicates alkyl groups having from 1 to about 6 carbon atoms. More preferred alkyl groups are methyl, ethyl and propyl groups.

As used herein, "alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy. "$C_1$–$C_6$ alkoxy" indicates alkoxy groups having from 1 to about 6 carbon atoms. Preferred alkoxy groups are methoxy, ethoxy, propoxy, and botoxy groups.

"Alkenyl" is intended to include hydrocarbon chains of either a straight or branched configuration comprising one or more unsaturated carbon-carbon bonds which may occur in any stable point along the chain, such as ethenyl and propenyl. Alkenyl groups typically have 2 to about 12 carbon atoms, more typically 2 to about 8 carbon atoms and preferably 2–6 carbon atoms.

"Alkynyl" is intended to include hydrocarbon chains of either a straight or branched configuration comprising one or more triple carbon-carbon bonds which may occur in any stable point along the chain, such as ethynyl and propynyl. Alkynyl groups typically have 2 to about 12 carbon atoms, more typically 2 to about 8 carbon atoms and preferably 2–6 carbon atoms.

"Aryl" refers to aromatic groups having 1 or more rings, wherein the members of the aromatic ring or rings are carbon. When indicated such groups may be substituted. Such groups include optionally substituted phenyl and optionally substituted naphthyl.

The term "cycloalkyl" is intended to include saturated ring groups, having the specified number of carbon atoms, such as cyclopropyl, cyclobutyl, cyclopentyl, or cyclohexyl. Cycloalkyl groups typically will have 3 to about 8 ring members.

In the terms "(cycloalkyl)alkyl" and "alkyl", defined above, the point of attachment is through a carbon atom in the alkyl group. This term encompasses, but is not limited to, cyclopropylmethyl, cyclohexylmethyl, cyclohexylmethyl. In the term "cycloalkyl", the point of attachment is through a ring carbon atom.

As used herein, "haloalkyl" is intended to include both branched and straight-chain saturated aliphatic hydrocarbon groups having the specified number of carbon atoms, substituted with 1 or more halogen atoms (for example —C$_v$F$_w$ where v=1 to 3 and w=1 to (2v+1). Examples of haloalkyl include, but are not limited to, trifluoromethyl, difluoromethyl, trichloromethyl, pentafluoroethyl, and pentachloroethyl.

As used herein, "haloalkoxy" indicates a haloalkyl group as defined above with the indicated number of carbon atoms attached through an oxygen bridge. Examples of haloalkoxy groups include, but are not limited to, trifluoromethoxy and trichloromethoxy.

As used herein the term "heteroaryl" is intended to mean a stable 5- to 7-membered monocyclic or bicyclic or 7-to 10-membered bicyclic heterocyclic aromatic ring which consists of carbon atoms and from 1 to 4 heteroatoms independently selected from the group consisting of N, O and S. It is preferred that the total number of S and O atoms in the aromatic heterocycle is not more than 1.

Examples of heteroaryl groups include, but are not limited to, pyrimidinyl, pyridyl, quinolinyl, benzothienyl, indolyl, pryidazinyl, pyazinyl, isoindolyl, isoquinolyl, quinazolinyl, quinoxalinyl, phthalazinyl, imidazolyl, isoxazolyl, pyrazolyl, oxazolyl, thienyl, thiazolyl, indolizinyl, indazolyl, benzothiazolyl, benzimidazolyl, benzofuranyl, benzoisoxolyl, dihydro-benzodioxinyl, furanyl, pyrrolyl, oxadiazolyl, thiadiazolyl, triazolyl, tetrazolyl, oxazolopyridinyl, imidazopyridinyl, isothiazolyl, naphthyridinyl, cinnolinyl, carbazolyl, beta-carbolinyl, isochromanyl, chromanonyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, phenoxazinyl, phenothiazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromanyl, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, and benzothiopyranyl S,S-dioxide.

Preferred heterocyclic groups include, but are not limited to, pyridinyl, pyrimidinyl, furanyl, thienyl, pyrrolyl, pyrazolyl, pyrrolidinyl, morpholinyl, piperidinyl, piperazinyl, and imidazolyl. Also included are fused ring and spiro compounds containing, for example, the above heterocycles.

The term "oxo" indicates the oxygen atom forming carbonyl group. When an oxo group appears as a substituent the allowed valence of the substituted position is not exceeded. When an aryl or heteroaryl group is substituted with oxo the aryl or heteroaryl group is converted to a partially saturated system. For example a pyridyl group substituted with oxo is a pyridone.

The phrase "pharmaceutically acceptable" is employed herein to refer to those compounds, materials, compositions, and/or dosage forms which are, within the scope of sound medical judgment, suitable for use in contact with the tissues of human beings or animals without excessive toxicity, irritation, allergic response, or other problem or complication, commensurate with a reasonable benefit/risk ratio. As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, malefic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, HOOC—$(CH_2)n$—COOH where n is 0–4, and the like. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., p. 1418 (1985).

The terms "trihaloalkyl" and "trihaloalkoxy" refer to particular types of haloalkyl and haloalkoxy groups that contain three halogen atoms, e.g., trichloromethyl, trifluormethyl, and trifluoromethoxy.

PHARMACEUTICAL COMPOSITIONS

The compounds of general Formulas I may be administered orally, topically, parenterally, by inhalation or spray or rectally in dosage unit formulations containing conventional non-toxic pharmaceutically acceptable carriers, adjuvants and vehicles. Oral administration in the form of a pill, capsule, elixir, syrup, lozenge, troche, or the like is particularly preferred. The term parenteral as used herein includes subcutaneous injections, intradermal, intravascular (e.g., intravenous), intramuscular, spinal, intrathecal injection or like injection or infusion techniques. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general Formulas I may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials are cocoa butter and polyethylene glycols.

Compounds of general Formulas I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

For administration to non-human animals, the composition may also be added to the animal feed or drinking water. It will be convenient to formulate these animal feed and drinking water compositions so that the animal takes in an appropriate quantity of the composition along with its diet. It will also be convenient to present the composition as a premix for addition to the feed or drinking water.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

Frequency of dosage may also vary depending on the compound used and the particular disease treated. However, for treatment of most disorders, a dosage regimen of 4 times daily or less is preferred. For the treatment of anxiety, depression, or cognitive impairment a dosage regimen of 1 or 2 times daily is particularly preferred. For the treatment of sleep disorders a single dose that rapidly reaches effective concentrations is desirable.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Preferred compounds of the invention will have certain pharmacological properties. Such properties include, but are not limited to high solubility (preferably 500 ng/ml or more) in aqueous solutions, oral bioavailability, low toxicity, low serum protein binding, lack of clinically relevant EKG effects, and desirable in vitro and in vivo half-lifes. Penetration of the blood brain barrier for compounds used to treat CNS disorders is necessary, while low brain levels of compounds used to treat periphereal disorders are often preferred.

Assays may be used to predict these desirable pharmacological properties. Assays used to predict bioavailability include transport across human intestinal cell monolayers, including Caco-2 cell monolayers. Toxicity to cultured hepatocyctes may be used to predict compound toxicity. Penetration of the blood brain barrier of a compound in humans may be predicted from the brain levels of the compound in laboratory animals given the compound intravenously.

Serum protein binding may be predicted from albumin binding assays. Such assays are described in a review by Oravcová, et al. (Journal of Chromatography B (1996) volume 677, pages 1–27).

Compound half-life is inversely proportional to the frequency of dosage of a compound. In vitro half-lifes of compounds may be predicted from assays of microsomal half-life as described by Kuhnz and Gieschen (Drug Metabolism and Disposition, (1998) volume 26, pages 1120–1127).

EXAMPLES

Preparation of Compounds

Representative synthetic routes for the preparation of the compounds of the invention are outlined in the following reaction schemes. The reactions shown below show specific methods for the synthesis compounds of the invention. However, one of ordinary skill in the art will recognize that reagents and reaction conditions may be varied to obtain additional specific end products. Further, it is readily apparent that additional compounds within the scope of Formula I but not specifically described within the experimental section may be prepared in analogous fashion. When a protecting group is employed, deprotection may be required. Suitable protecting groups and methodology for protection and deprotection such as those described in *Protecting Groups in Organic Synthesis* by T. Greene are well known and appreciated in the art. Compounds and intermediates requiring protection/deprotection will be readily apparent to those skilled in the art.

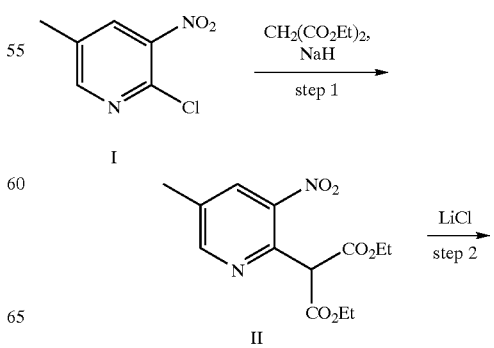

Scheme I

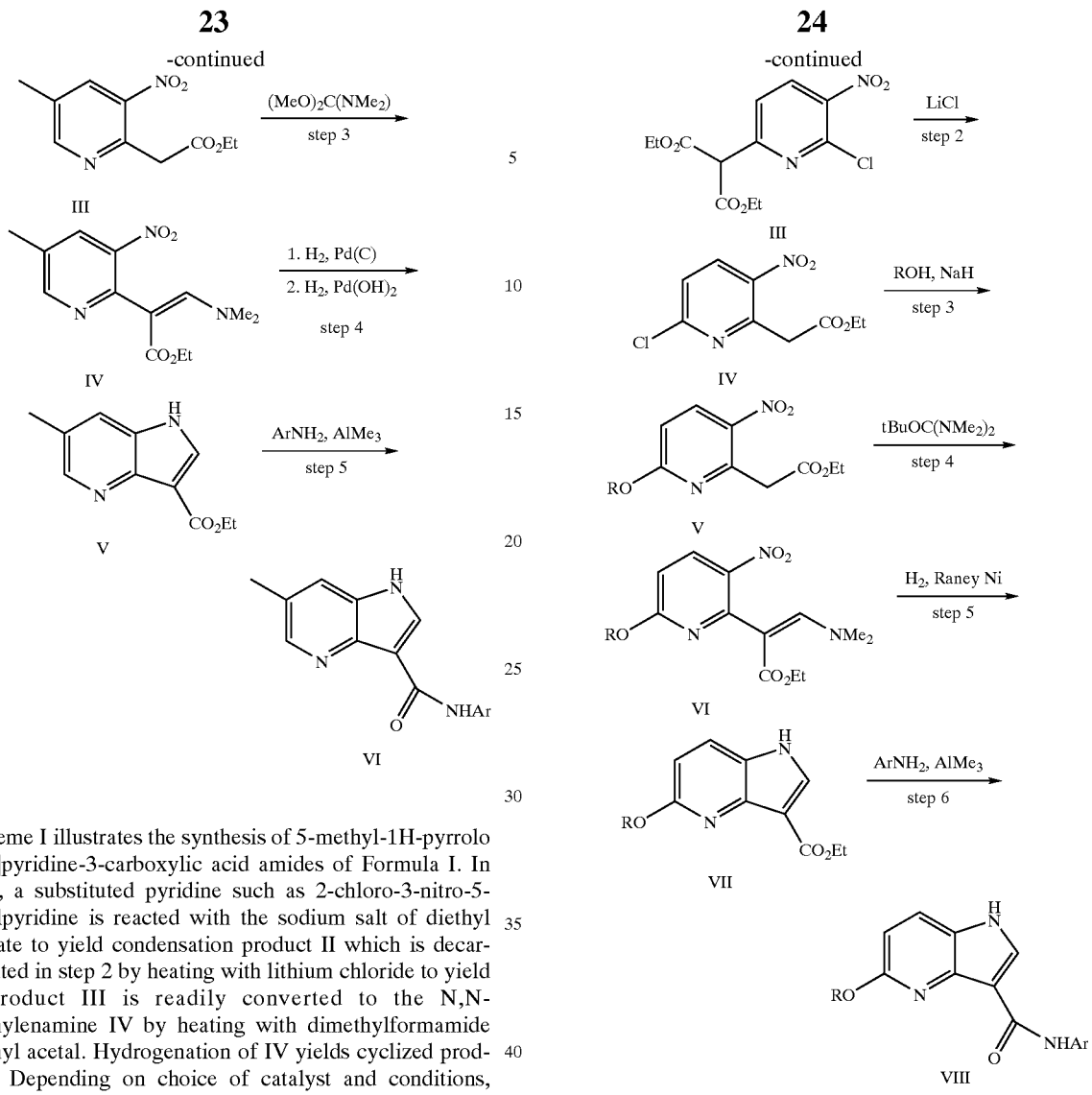

Scheme I illustrates the synthesis of 5-methyl-1H-pyrrolo[3,2-b]pyridine-3-carboxylic acid amides of Formula I. In step 1, a substituted pyridine such as 2-chloro-3-nitro-5-methylpyridine is reacted with the sodium salt of diethyl malonate to yield condensation product II which is decarboxylated in step 2 by heating with lithium chloride to yield III. Product III is readily converted to the N,N-dimethylenamine IV by heating with dimethylformamide dimethyl acetal. Hydrogenation of IV yields cyclized product V. Depending on choice of catalyst and conditions, hydrogenation may also yield 1-hydroxy-6-methyl-1H-pyrrolo[3,2-b]pyridine-3-carboxylic acid ethyl ester. If this occurs, subsequent further hydrogenation in the presence of palladium (II) hydroxide can be used to convert 1-hydroxy-6-methyl-1H-pyrrolo[3,2-b]pyridine-3-carboxylic acid ethyl ester to V. Amination of V is conveniently accomplished by reaction with an appropriate amine derivative in the presence of trimethylaluminum to yield a compound of formula VI.

Scheme II

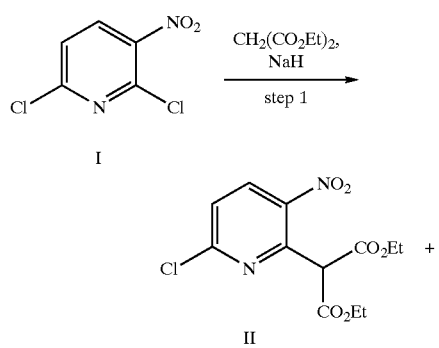

In Scheme II, an appropriate pyridine such as 2-chloro-3-nitro-6-chloropyridine I is reacted with the sodium diethylmalonate to obtain a mixture of condensation product II along with minor product III. In step 2, decarboxylation of the mixture of II and III by heating with lithium chloride followed by purification on silica gel provides IV. In step 3, product IV is reacted with a sodium alkoxide to provide the corresponding alkoxypyridine V. In step 4, alkoxypyridine V is heated with tert-butoxybis(dimethylamino)methane to provide N,N-dimethylenamine VI. Hydrogenation of enamine VI in the presence of Raney nickel cleanly provides 5-alkoxy-1H-pyrrolo[3,2-b]pyridine-3-carboxylic acid ethyl ester VII, in step 5. Amination is conveniently accomplished in step 6 by reaction with an appropriate amine derivative in the presence of trimehtylaluminum to yield a compound of formula VIII.

The following experimental examples illustrate but do not limit the present invention. In the examples, commercial reagents are used without further purification. Purification by chromatography is done on prepacked silica columns from Biotage (Dyax Corp, Biotage Division, Charlottesville, Va.). Melting points (mp) are obtained using a Mettler Toledo FP62 melting point apparatus (Mettler-Toledo, Inc., Worthington, Ohio) with a temperature ramp rate of 10° C./min and are uncorrected. Proton nuclear magnetic resonance ($^1$H NMR) spectra are recorded in deuterated solvents on a Varian INOVA400 (400 MHz) spectrometer (Varian NMR Systems, Palo Alto, Calif.). Chemical shifts are reported in parts per million (ppm, δ) relative to Me$_4$Si (δ 0.00). Proton NMR splitting patterns are designated as singlet (s), doublet (d), triplet (t), quartet (q), quintet (quin), sextet (sex), septet (sep), multiplet (m) apparent (ap) and broad (br). Coupling constants are reported in hertz (Hz). Carbon-13 nuclear magnetic resonance ($^{13}$C NMR) spectra are recorded on a Varian INOVA400 (100 MHz). Chemical shifts are reported in ppm (δ) relative to the central line of the 1:1:1 triplet of deuterochloroform (δ 77.00), the center line of deuteromethanol (δ 49.0) or deuterodimethylsulfoxide (δ 39.7). The number of carbon resonance's reported may not match the actual number of carbons in some molecules due to magnetically and chemically equivalent carbons and may exceed the number of actual carbons due to conformational isomers. Mass spectra (MS) are obtained using a Waters ZMD mass spectrometer using flow injection atmospheric pressure chemical ionization (APCI) (Waters Corporation, Milford, Mass.). Gas chromatography with mass detection (GCMS) are obtained using a Hewlett Packard HP 6890 series GC system with a HP 5973 mass selective detector and a HP-1 (crosslinked methyl siloxane) column (Agilent Technologies, Wilmington, Del.). HPLC spectra are recorded on a Hewlett Packard 1100 series HPLC system with a Zorbax SB-C8, 5 um, 4.6×150 mm column (Agilent Technologies, Wilmington, Del.) at 25° C. using gradient elution. Solvent A is water, Solvent B is acetonitrile, Solvent C is 1% trifluoroacetic acid in water. A linear gradient over four minutes is used starting at 80%A, 10%B, 10%C and ending at 0%A, 90%B, 10%C. The eluent remained at 0%A, 90%B, 10%C for three minutes. A linear gradient over one minute is used to return the eluent to 80%A, 10%B, 10%C and it is held at this until the run time equaled ten minutes. Room temperature (RT) refers to 20–25° C. The abbreviations "h" and "hrs" refer to "hours".

Example 1
Preparation of 6-Methyl-1H-pyrrolo[3,2-b]pyridine-3-carboxylic Acid Ethyl Ester A. Preparation of 2-Chloro-5-methyl-3-nitro-pyridine

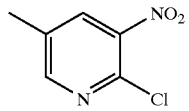

2-Chloro-5-methyl-3-nitro-pyridine is prepared according to the method given in J.Mol Struct (1991) 248: 189–200 or may be purchased from SPECS and BioSPECS B.V., Fleminglaan, The Netherlands.

B. Preparation of 2-(5-Methyl-3-nitro-pyridin-2-yl)-malonic Acid Diethyl Ester

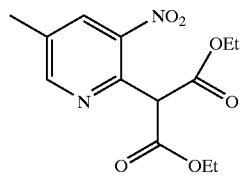

A solution of diethyl malonate (72 g, 0.436 mol) in DME (200 mL) is added dropwise to a magnetically stirred suspension of NaH (23 g, 0.58 mol) in dry 1,2-dimethoxyethane (DME, 350 mL). The mixture is stirred at room temperature for 1 hour and then a solution of 2-chloro-5-methyl-3-nitro-pyridine (50 g, 0.290 mol) in DME (100 mL) is added to give a dark red solution. After stirring for 18 hours, the reaction mixture is poured into ice-cold water and acidified to pH 3 with 6N HCl solution. The mixture is extracted with ethyl acetate. The organic phase is washed with water, brine, dried over Na$_2$SO$_4$, and concentrated. The excess diethymalonate is removed at 50° C. under high vacuum to give 2-(5-Methyl-3-nitro-pyridin-2-yl)-malonic acid diethyl ester i as a dark red-colored thick residue; $^1$H NMR (300 MHz, CDCl$_3$) δ 1.28 (t, J=9 Hz, 6H), 4.26 (q, J=9 Hz, 4H), 8.27 (s, 1H), 8.63 (s, 1H).

C. Preparation of (5-Methyl-3-nitro-pyridin-2-yl)-acetic Acid Ethyl Ester:

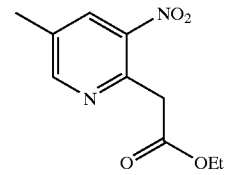

LiCl (10.6 g, 0.252 mol) is suspended in a solution of 2-(5-Methyl -3-nitro-pyridin-2-yl)-malonic acid diethyl ester (50 g, 0.168 mol) in DMSO (100 mL) containing water (12 g, 0.678 mol) and is stirred at 150° C. for 3 h. The reaction mixture is cooled, diluted with water (200 mL), and extracted with ethyl acetate. The combined organic phase are washed successively with saturated aqueous NaHCO$_3$, water, brine, dried over Na$_2$SO$_4$, and concentrated in vacuo. The residue is purified by silica gel chromatography eluting with 20% EtOAc-hexanes to afford (5-Methyl-3-nitro-pyridin-2-yl)-acetic acid ethyl ester as an oil; $^1$H NMR (300 MHz, CDCl$_3$) δ 1.23 (t, J=9 Hz, 3H), 4.15 (q, J=9 Hz, 2H), 4.25 (s, 2H), 8.2 (s, 1H), 8.58 (s, 1H).

D. Preparation of 3-Dimethylamino-2-(5-methyl-3-nitro-pyridin-2-yl]-acrylic Acid Ethyl Ester

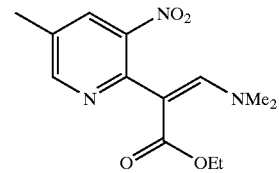

A solution of dimethylformamide dimethyl acetal (4 g, 0.033 mol) in dry DMF (10 mL) is added to a solution of (5-methyl-3-nitro-pyridin-2yl)-acetic acid ethyl ester (5 g, 0.022 mol) in dry DMF (20 mL) to give a red solution. This solution is heated at 60° C. under reduced pressure for 3 h. DMF and other volatile components are evaporated under reduced pressure to obtain 3-dimethylamino-2-(5-methyl-3-nitro-pyridin-2-yl)-acrylic acid ethyl ester as an viscous oil which was used without further purification.

E. Preparation of 1-Hydroxy-6-methyl-1H-pyrrolo[3,2-b] pyridine-3-carboxylic Acid Ethyl Ester

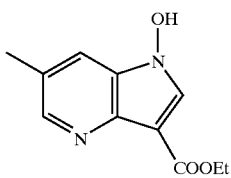

A solution of 3-Dimethylamino-2-(5-methyl-3-nitro-pyridin-2-yl]-acrylic acid ethyl ester (6.2 g, 0.022 mol) in ethanol (50 mL) is hydrogenated over 10% Pd-C at 50 psi for 48 h. The catalyst is removed by filtration through a pad of celite, and the solvent evaporated under vacuum. The residue is chromatographed over silica gel eluting with 7% MeOH-DCM containing few drops of $NH_4OH$ to afford 1-Hydroxy-6-methyl-1H-pyrrolo[3,2-b]pyridine-3-carboxylic acid ethyl ester $^1H$ NMR (300 MHz, DMSO-$d_6$) δ 1.25 (t, J=6.6 Hz, 3H), 4.21 (q, J=6.6 Hz, 2H), 7.59 (s, 1H), 8.15 (s, 1H), 8.29 (s, 1H); LRMS Calcd 220.2; found 221.12.

F. Preparation of 6-Methyl-1H-pyrrolo[3,2-b]pyridine-3-carboxylic Acid Ethyl Ester

Pd(OH)$_2$ (200 mg) is added to a solution of 1-Hydroxy-6-methyl-1H-pyrrolo[3,2-b]pyridine-3-carboxylic acid ethyl ester (1.2 g, 0.005 mole) in ethanol (20 mL) and is hydrogenated at 50 psi for 24 h. The catalyst is removed by filtration through a pad of celite and the solvent evaporated under vacuum. The residue is chromatographed over silica gel eluting with 5% MeOH-DCM containing few drops of $NH_4OH$ to afford 6-Methyl-1H-pyrrolo[3,2-b]pyridine-3-carboxylic acid ethyl ester (550 mg, 50%); $^1H$ NMR (300 MHz, DMSO-$d_6$) δ 1.28 (t, J=6 Hz, 3H), 2.38 (s, 3H), 4.24 (q, J=6.6 Hz, 2H), 7.62 (s, 1H); 8.17 (s, 1H), 8.31 (s, 1H); LRMS Calcd 204.23; found 205.15.

Example 2
Preparation of 5-(1-Methyl-piperidin-4-yloxy)-1H-pyrrolo[3,2-]pyridine-3-carboxylic Acid Pyridin-2-ylamide
A. Preparation of 2-(6-Chloro-3-nitro-pyridin-2-yl)-malonic Acid Diethyl Ester

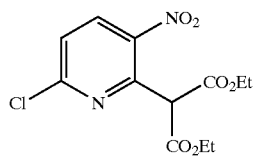

5-(1-Methyl-piperidin-4-yloxy)-1H-pyrrolo[3,2-b]pyridine-3-carboxylic acid pyridin-2-ylamide can be prepared as a 2:1 mixture of regioisomers II/III (Scheme I) according to the procedure of Robinson, R. P., et. al. *J. Heterocyclic Chem.* 1996, V33, p287. Alternatively, the title compound can be prepared as a 4.6:1 mixture of regioisomers II/III using the following reaction conditions. A mixture of diethylmalonate (7.95 mL, 52.3 mmol) in THF (20 mL) is added dropwise over a period of 35 minutes to a mixture of NaH (4.35 g, 108.8 mmol) in THF (150 mL) at room temperature. The resulting mixture is stirred at room temperature for a period of 40 minuters and then cooled until the internal temperature is –20° C. Next, a solution of 2,6-dicholoro-3-nitropyridine (10.0 g, 51.8 mmol) in THF (25 mL) is added over a period of 10 minutes while maintaining the internal temperature of –20° C. The reaction mixture is warmed to room temperature over a period of 3 h and stirred for an additonal 30 minuters. A saturated solution of $NH_4Cl$ (20 mL) is added over a period of 10 minutes followed by the addition of $H_2O$ (20 mL) and brine (20 mL). The mixture is diluted with EtOAc (100 mL), the layers partitioned, and the aqueous layer extracted with EtOAc (2×50 mL). The combined organic layers are washed with a 50% brine solution (100 mL) and then with brine (100 mL). The organic layers are dried over $Na_2SO_4$, filtered to remove the solid and concentrated (in vacuo) to give of the title compound as a 4.6:1 mixture of regioisomers II/III as a dark red oil: $^1H$ NMR (400 MHz, CDCl$_3$) δ 8.42 (d, 1H, J=8.7 Hz, major), 8.24 (d, J=8.3 Hz, minor), 7.69 (d, J=8.3 Hz, minor), 7.50 (d, 1H, J=8.7 Hz, major), 5.44 (s, 1H, major), 4.96 (s, 0.22H, minor), 4.32–4.27 (m, 4H), 1.30–1.23 (m, 6H); MS (CI) m/z 317.2/319.4 (M+1).

B. Preparation of (6-Chloro-3-nitro-pyridin-2-yl)-acetic Acid Ethyl Ester

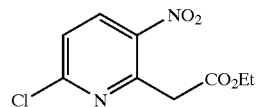

A mixture of 2-(6-Chloro-3-nitro-pyridin-2-yl)-malonic acid diethyl ester (32.45 g, 103 mmol), LiCl (16.18 g, 268 mmol), $H_2O$ (10 mL), and dimethyl sulfoxide (50 mL) is stirred at 120° C. for a period of 24 h. The mixture is cooled to room temperature and diluted with $H_2O$ (400 mL). 1 N HCl (aq.) is added until all of the solids are dissolved. The mixture is extracted with EtOAc (5×150 mL), and the combined organic extracts washed with $H_2O$ (2×100 mL), then brine (100 mL), and dried over $Na_2SO_4$. The mixture is filter to remove the solids, concentrated, and purified by flash chromatography on silica (elute with 5% EtOAc in hexanes) to give the title compound as a yellow oil: $^1H$ NMR (400 MHz, CDCl$_3$) δ 8.39 (d, 1H, J=8.7 Hz), 7.47 (d, 1H, J=8.7 Hz), 4.28 (s, 2H), 4.19 (q, 2H, J=7.1 Hz), 1.27 (t, 3H, J=7.1 Hz); $^{13}C$ (100 MHz, CDCl$_3$) δ 168.7, 166.8, 154.8, 151.4, 135.9, 124.4, 61.7, 41.9, 14.3; MS (CI) m/z 255.2 (M+1).

C. Preparation of [6-(1-Methyl-piperidin-4-yloxy)-3-nitro-pyridin-2-yl]-acetic Acid Ethyl Ester

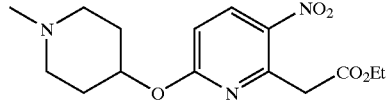

Sodium hydride (60%, 1.64 g, 41 mmol) is added to a solution of 4-hydroxy-1-methylpiperidine (4.72 g, 41 mmol) in THF (82 mL) at room temperature. The mixture is stirred for a period of 30 minutes. A solution of (6-chloro-3-nitro-pyridin-2-yl)-acetic acid ethyl ester (5.0 g, 20.5 mmol) in THF (10 mL) is then added. The resulting purple mixture is stirred at room temperature for a period of 70 minutes. An additional portion of NaH (410 mg, 10.3 mmol) is added. The resulting mixture is stirred for a period of 70 minutes at room temperature and a saturated solution of NaHCO$_3$ (30 mL) is then added slowly. The mixture is diluted with EtOAc (100 mL) and 1 N NaOH (aq, 10 mL). The layers are partititioned and the aqueous layer extracted with EtOAc (3×50 mL). The combined organic extracts are washed with $H_2O$ (50 mL) and brine (50 mL) and dried over $Na_2SO_4$. The mixture is filtered to remove the solids, concentrated, and purified by flash chromatography on silica (gradient elution: 50% EtOAc in hexanes to 2% MeOH/CHCl$_3$ with 0.1% NH$_4$OH to 4% MeOH/CHCl$_3$, with 0.1% NH$_4$OH) to give the title compound as a dark brown oil: $^1$H NMR (400 MHz, CDCl$_3$) δ 8.34 (d, 1H, J=9.1 Hz), 6.73 (d, 1H, J=9.1 Hz), 4.18 (q, 2H, J=7.1 Hz), 4.17 (s, 2H), 2.70–2.65 (m, 2H), 2.35–2.27 (m, 2H), 2.30 (s, 3H), 2.07–2.00 (m, 2H), 1.89–1.80 (m, 2H), 1.25 (t, 3H, J=7.1 Hz); $^{13}$C NMR (100 MHz, CDCl$_3$) δ 169.5, 164.6, 150.6, 139.5, 136.5, 111.3, 72.5, 61.4, 53.0, 46.3, 44.0, 30.9, 14.4; MS (CI) m/z 324.2 (M+1).

D. Preparation of 3-Dimethylamino-2-[6-(1-methyl-piperidin-4-yloxy)-3-nitro-pyridin-2-yl]-acrylic Acid Ethyl Ester

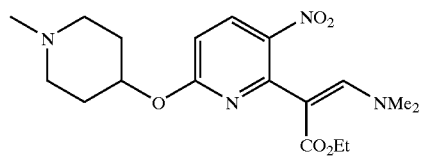

A mixture of [6-(1-methyl-piperidin-4-yloxy)-3-nitro-pyridin-2-yl]-acetic acid ethyl ester (5.93 g, 18.3 mmol) and tert-butoxybis(dimethylamino)methane (5.7 mL, 27.5 mmol) at is heated 65° C. for a period of 6 h. The mixture is cooled to room temperature and purified by flash chromatography on silica (gradient elution with 4% MeOH/CHCl$_3$ with 0.1% NH$_4$OH to 6% MeOH/CHCl$_3$ with 0.1% NH$_4$OH) to give the title compound as a dark orange oil: $^1$H NMR (400 MHz, CDCl$_3$) δ 8.03 (d, 1H, J=9.1 Hz), 7.5 (s, 1H), 6.49 (d, 1H, J=9.1 Hz), 5.00–4.96 (m, 1H), 3.97–3.82 (m, 2H), 2.69 (br s, 6H), 2.60–2.50 (m, 2H), 2.20–2.10 (m, 2H), 2.16 (s, 3H), 1.92–1.85 (m, 2H), 1.74–1.65 (m, 2H), 0.98 (t, 3H, J=7.1 Hz); $^{13}$C NMR (100 MHz, CDCl$_3$) δ 167.7, 163.3, 151.7, 150.8, 141.8, 135.5, 109.3, 96.8, 71.7, 59.8, 52.9, 46.3, 43.6, 31.4, 30.9, 14.4; MS (CI) m/z 379.3 (M+1).

E. Preparation of 5-(1-Methyl-piperidin-4-yloxy)-1H-pyrrolo[3,2-b]pyridine-3-carboxylic Acid Ethyl Ester

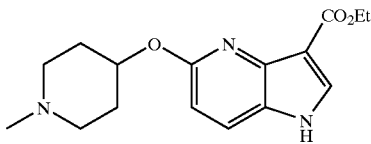

A mixture of 3-dimethylamino-2-[6-(1-methyl-piperidin-4-yloxy)-3-nitro-pyridin-2-yl]-acrylic acid ethyl ester (3.69 g, 9.76 mmol), RANEY 2400 nickel (3.7 g wet) in EtOH (100 mL) is shaken at room temperature under an atmosphere of hydrogen (50 psi) for a period of 7 h. During this time period, the pressure dropped to 20 psi. The reaction vessel is recharged with hydrogen (50 psi) and shaken at room temperature for a period of 17 h. The reaction mixture is filtered through celite and the filtrate washed with EtOH (300 mL) taking care to never allow the filtrate to become dry. The filtrate is concentrated and purified by chromatography on silica (gradient elution with 10% MeOH/CHCl$_3$ with 0.1% NH$_4$OH to 14% MeOH/CHCl$_3$ with 0.1% NH$_4$OH) to give the title compound as a yellow solid: m.p=231.9° C.; $^1$H NMR (400 MHz, CDCl$_3$) δ 7.93 (s, 1H), 7.64 (d, 1H, J=8.7 Hz), 6.51 (d, 1H, J=8.7 Hz), 5.36–5.28 (m, 1H), 4.26 (q, 2H, J=7.1 Hz), 3.15–3.06 (m, 2H), 3.00–2.90 (m, 2H), 2.61 (s, 3H), 2.30–2.20 (m, 2H), 2.18–2.08 (m, 2H), 1.30 (t, 3H, J–7.1 Hz); $^{13}$C NMR (100 MHz, CDCl$_3$) δ 165.0, 159.3, 140.5, 133.7, 125.8, 123.7, 107.3, 106.6, 66.1, 60.0, 51.6, 44.2, 28.5, 14.6; MS (CI) m/z 304.3 (M+1).

F. Preparation of 5-(1-Methyl-piperidin-4-yloxy)-1H-pyrrolo[3,2-b]pyridine-3-carboxylic Acid Pyridin-2-ylamide

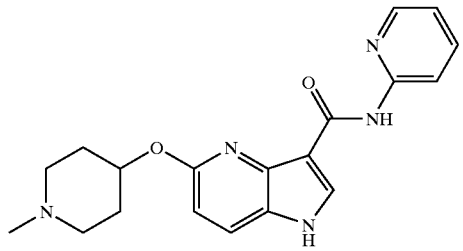

AlMe$_3$ (0.3 mL, 0.59 mmol, 2 M in PhCH$_3$) is added to a solution of 2-aminopyridine (56 mg, 0.59 mmol) in toluene (1.0 mL) and 1,2-dichloroethane (1.0 mL) at room temperature. The resulting solution is stirred for 30 minutes at room temperature, 5-(1-methyl-piperidin-4-yloxy)-1H-pyrrolo[3,2-b]pyridine-3-carboxylic acid ethyl ester (60 mg, 0.20 mmol) is then added. The resulting mixture is heated at 100° C. for a period of 3 h. The mixture is cooled to room temperature and Na$_2$SO$_4$.10H$_2$O (285 mg, 0.89 mmol) is added. The mixture is stirred for 30 minutes and MeOH (5 mL) is added. The resulting mixture is filtered through a pad of celite and washed with MeOH (3×5 mL) and CHCl$_3$ (3×5 mL). The filtrate is concentrated and purified by chromatography on silica (gradient elution with 5% MeOH/CHCl$_3$ with 0.1% NH$_4$OH to 8% MeOH/CHCl$_3$ with 0.1% NH$_4$OH to 10% MeOH/CHCl$_3$ with 0.1% NH$_4$OH) to give the title compound as a light yellow solid: (Cmp. #1) $^1$H NMR (400 MHz, CD$_3$OD) δ 8.29–8.27 (m, 2H), 8.01 (s, 1H), 7.73–7.69 (m, 2H), 7.03 (dd, 1H, J=7.1, 5.4 Hz), 6.63 (d, 1H, J=8.7 Hz), 5.40–5.34 (m, 1H), 2.86–2.80 (m, 2H), 2.57–2.52 (m, 2H), 2.35 (s, 3H), 2.30–2.26 (m, 2H), 1.91–1.86 (m, 2H); $^{13}$C NMR (100 MHz, CD$_3$OD) δ 163.9, 159.5, 152.4, 148.1, 139.1, 138.2, 131.6, 125.1, 124.1, 119.5, 114.2, 109.3, 107.2, 70.8, 53.6, 45.7, 30.8; MS (CI) m/z 352.3 (M+1).

Example 3

The compounds shown Tables I, II, and III are synthesized essentially according to the procedures set forth in the above schemes and examples.

TABLE I

5

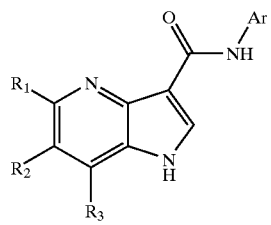

| Cpd. # | Name | R₁ | R₂ | R₃ | Ar | ¹H NMR | Mass Spec (Calc/Obs. M + 1 or M − 1) |
|---|---|---|---|---|---|---|---|
| 2 | 1H-Pyrrolo[3,2-b]pyridine-3-carboxylic acid (2-fluoro-phenyl)-amide | H | H | H | 2-fluorophenyl | | 255.25/256.2 |
| 3 | 1H-Pyrrolo[3,2-b]pyridine-3-carboxylic acid pyridin-2-ylamide | H | H | H | pyridin-2-yl | | 238.25/239.1 |
| 4 | 7-Chloro-1H-pyrrolo[3,2-b]pyridine-3-carboxylic acid (2-fluoro-phenyl)-amide | H | H | Cl | 2-fluorophenyl | | 289.7/288.2 |
| 5 | 6-Methyl-1H-pyrrolo[3,2-b]pyridine-3-carboxylic acid (4-methoxy-phenyl)-amide | H | CH₃ | H | 4-methoxyphenyl | | 281.32/282.2 |
| 6 | 6-Methyl-1H-pyrrolo[3,2-b]pyridine-3-carboxylic acid (5-propoxy-pyridin-2-yl)-amide | H | CH₃ | H | 5-chloropyridin-2-yl | | 310.36/311.2 |
| 7 | 6-Methyl-1H-pyrrolo[3,2-b]pyridine-3-carboxylic acid pyridin-3-ylamide | H | CH₃ | H | 6-bromopyridin-3-yl | | 252.28/253.2 |
| 8 | 5-Methoxy-1H-pyrrolo[3,2-b]pyridine-3-carboxylic acid (2-fluoro-phenyl)-amide | OCH₃ | H | H | 2-fluorophenyl | | 285.27/286.1 |
| 9 | 5-Methoxy-1H-pyrrolo[3,2-b]pyridine-3-carboxylic acid pyridin-2-ylamide | OCH₃ | H | H | pyridin-2-yl | | 268.27/268.31 |
| 10 | 5-Methoxy-1H-pyrrolo[3,2- | OCH₃ | H | H | OCH₃-aryl | | 297.32/298.2 |

TABLE II

[Structure: pyrrolo[3,2-b]pyridine-3-carboxamide core with R₁, R₂ substituents and N-Ar amide]

| Cpd. # | Name | R₁ | R₂ | Ar | ¹H NMR | Mass Spec (Calc/Obs. M + 1 or M − 1) |
|---|---|---|---|---|---|---|
| 20 | 1H-Pyrrolo[3,2-b]pyridine-3-carboxylic acid quinolin-8-ylamide | H | H | quinolin-8-yl | | 288.31/289.2 |
| 21 | 1H-Pyrrolo[3,2-b]pyridine-3-carboxylic acid [4-(3-methanesulfonylamino-propoxy)-phenyl]-amide | H | H | 4-(3-NHSO₂Me-propoxy)phenyl | | 388.4/389.2 |
| 22 | 1H-Pyrrolo[3,2-b]pyridine-3-carboxylic acid (3-propyl-[1,2,4]thiadiazol-5-yl)-amide | H | H | 3-propyl-[1,2,4]thiadiazol-5-yl | | 287.35/288.3 |
| 23 | 1H-Pyrrolo[3,2-b]pyridine-3-carboxylic acid (1-methyl-1H-pyrazol-3-yl)-amide | H | H | 1-methyl-1H-pyrazol-3-yl | | 241.25/242.1 |
| 24 | 6-Methyl-1H-pyrrolo[3,2-b]pyridine-3-carboxylic acid (1-propyl-1H-pyrazol-3-yl)-amide | H | CH₃ | 1-propyl-1H-pyrazol-3-yl | | 283.33/282.1 |
| 25 | 6-Methyl-1H-pyrrolo[3,2-b]pyridine-3-carboxylic acid pyrazin-2-ylamide | H | CH₃ | pyrazin-2-yl | | 253.27/254.2 |
| 26 | 5-Methoxy-1H-pyrrolo[3,2-b]pyridine-3-carboxylic acid [6-(3-diethylamino-propoxy)-pyridin-3-yl]-amide | CH₃ | H | 6-(3-NEt₂-propoxy)pyridin-3-yl | | 397.47/396.3 |
| 27 | 5-Methoxy-1H-pyrrolo[3,2-b]pyridine-3-carboxylic acid (pyridin-2-ylmethyl)-amide | CH₃ | H | pyridin-2-ylmethyl | | 282.3/281.1 |

TABLE II-continued

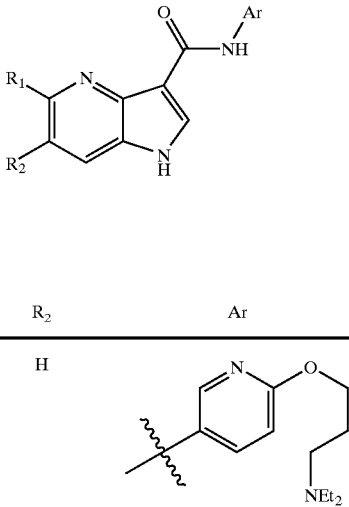

| Cpd. # | Name | R₁ | R₂ | Ar | ¹H NMR | Mass Spec (Calc/Obs. M + 1 or M − 1) |
|---|---|---|---|---|---|---|
| 28 | 5-Ethoxy-1H-pyrrolo[3,2-b]pyridine-3-carboxylic acid [6-(3-diethylamino-propoxy)-pyridin-3-yl]-amide | OEt | H | 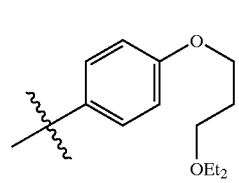 | | 411.51/410.3 |
| 29 | 5-Ethoxy-1H-pyrrolo[3,2-b]pyridine-3-carboxylic acid [4-(2-ethoxy-ethoxy)-phenyl]-amide | OEt | H | 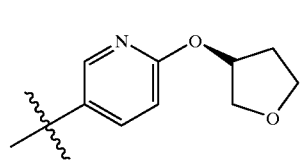 | | 369.42/370.2 |
| 30 | 5-Ethoxy-1H-pyrrolo[3,2-b]pyridine-3-carboxylic acid [6-(tetrahydro-furan-3-yloxy)-pyridin-3-yl]-amide | OEt | H | 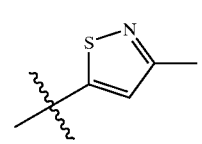 | | 368.4/369.2 |
| 31 | 5-Ethoxy-1H-pyrrolo[3,2-b]pyridine-3-carboxylic acid (3-methyl-isothiazol-5-yl)-amide | OEt | H | 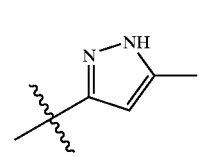 | | 302.36/303.1 |
| 32 | 5-Ethoxy-1H-pyrrolo[3,2-b]pyridine-3-carboxylic acid (5-methyl-1H-pyrazol-3-yl)-amide | OEt | H | 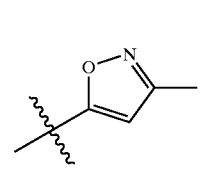 | | 285.31/286.2 |
| 33 | 5-Ethoxy-1H-pyrrolo[3,2-b]pyridine-3-carboxylic acid (3-methyl-isoxazol-5-yl)-amide | OEt | H | 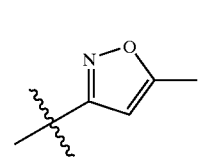 | | 286.29/287.2 |
| 34 | 5-Ethoxy-1H-pyrrolo[3,2-b]pyridine-3-carboxylic acid (5-methyl-isoxazol-3-yl)-amide | OEt | H |  | | 286.29/287.1 |

TABLE II-continued

| Cpd. # | Name | R₁ | R₂ | Ar | ¹H NMR | Mass Spec (Calc/Obs. M + 1 or M − 1) |
|---|---|---|---|---|---|---|
| 35 | 5-Ethoxy-1H-pyrrolo[3,2-b]pyridine-3-carboxylic acid (1-ethyl-1H-pyrazol-3-yl)-amide | OEt | H | | | 299.33/300.1 |
| 36 | 5-Ethoxy-1H-pyrrolo[3,2-b]pyridine-3-carboxylic acid [4-(2-hydroxy-ethyl)-phenyl]-amide | OEt | H | | | 325.37/326.3 |
| 37 | 5-Ethoxy-1H-pyrrolo[3,2-b]pyridine-3-carboxylic acid [4-(2-diethylamino-ethyl)-phenyl]-amide | OEt | H | | | 380.49/381.3 |
| 38 | 5-Ethoxy-1H-pyrrolo[3,2-b]pyridine-3-carboxylic acid (3-hydroxymethyl-phenyl)-amide | OEt | H | | | 311.34/312.3 |
| 39 | 5-Ethoxy-1H-pyrrolo[3,2-b]pyridine-3-carboxylic acid (3-pyrrolidin-1-ylmethyl-phenyl)-amide | OEt | H | | | 364.45/365.4 |
| 40 | 5-Ethoxy-1H-pyrrolo[3,2-b]pyridine-3-carboxylic acid [4-(2-pyrrolidin-1-yl-ethyl)-phenyl]-amide | OEt | H | | | 378.48/379.4 |
| 41 | 5-Isopropoxy-1H-pyrrolo[3,2-b]pyridine-3-carboxylic acid (3-methyl-isothiazol-5-yl)-amide | OiPr | H | | | 316.38/317.1 |

TABLE II-continued

| Cpd. # | Name | R₁ | R₂ | Ar | ¹H NMR | Mass Spec (Calc/Obs. M + 1 or M − 1) |
|---|---|---|---|---|---|---|
| 42 | 5-Isopropoxy-1H-pyrrolo[3,2-b]pyridine-3-carboxylic acid (3-methyl-isoxazol-5-yl)-amide | OiPr | H | | | 300.32/301.1 |
| 43 | 5-Isopropoxy-1H-pyrrolo[3,2-b]pyridine-3-carboxylic acid (5-methyl-isoxazol-3-yl)-amide | OiPr | H | | | 300.32/301.1 |
| 44 | 5-Isopropoxy-1H-pyrrolo[3,2-b]pyridine-3-carboxylic acid (5-methyl-1H-pyrazol-3-yl)-amide | OiPr | H | | | 299.33/300.1 |
| 45 | 5-Isopropoxy-1H-pyrrolo[3,2-b]pyridine-3-carboxylic acid (1-ethyl-1H-pyrazol-3-yl)-amide | OiPr | H | | | 313.36/314.1 |
| 46 | 5-(2-Methoxy-ethoxy)-1H-pyrrolo[3,2-b]pyridine-3-carboxylic acid (5-methyl-isoxazol-3-yl)-amide | | H | | | 316.32/317.0 |
| 47 | 5-(2-Methoxy-ethoxy)-1H-pyrrolo[3,2-b]pyridine-3-carboxylic acid (3-methyl-isoxazol-5-yl)-amide | | H | | | 316.32/317.0 |
| 48 | 5-(2-Methoxy-ethoxy)-1H-pyrrolo[3,2-b]pyridine-3-carboxylic acid (3-methyl-isothiazol-5-yl)-amide | | H | | | 332.38/333.1 |

TABLE II-continued

| Cpd. # | Name | R₁ | R₂ | Ar | ¹H NMR | Mass Spec (Calc/Obs. M + 1 or M − 1) |
|---|---|---|---|---|---|---|
| 49 | 5-(2-Methoxy-ethoxy)-1H-pyrrolo[3,2-b]pyridine-3-carboxylic acid (5-methyl-1H-pyrazol-3-yl)-amide | 1,3-dioxolan-2-yl (methyl) | H | 5-methyl-1H-pyrazol-3-yl | | 315.33/316.2 |
| 50 | 5-(1-Methyl-piperidin-4-yloxy)-1H-pyrrolo[3,2-b]pyridine-3-carboxylic acid (5-methyl-isoxazol-3-yl)-amide | 1-methylpiperidin-4-yloxy | H | 5-methyl-isoxazol-3-yl | 1H NMR (400 MHz, CD3OD) 7.96(s, 1H)), 7.63(d, 1H), 6.59(d, 1H), 6.23(s, 1H), 5.08–5.03(m, 1H), 2.85–2.80(m, 2H), 2.42–2.37(m, 2H), 2.29(s, 3H), 2.22(s, 3H), 2.21–2.17(m, 2H), 1.88–1.82(m, 2H) | 355.4/356.3 |
| 51 | 5-(1-Methyl-piperidin-4-yloxy)-1H-pyrrolo[3,2-b]pyridine-3-carboxylic acid pyridin-2-ylamide | 1-methylpiperidin-4-yloxy | H | pyridin-2-yl | 1H NMR (400 MHz, CD3OD) 8.29–8.27(m, 2H), 8.01(s, 1H), 7.73–7.69(m, 2H), 7.03(dd, 1H), 6.63(d, 1H), 5.40–5.34(m, 1H), 2.86–2.80(m, 2H), 2.57–2.52(m, 2H), 2.35(s, 3H), 2.30–2.26(m, 2H), 1.91–1.86(m, 2H) | 351.41/352.3 |
| 52 | 5-(1-Methyl-piperidin-4-yloxy)-1H-pyrrolo[3,2-b]pyridine-3-carboxylic acid (1-methyl-1H-pyrazol-3-yl)-amide | 1-methylpiperidin-4-yloxy | H | 1-methyl-1H-pyrazol-3-yl | 1H NMR (400 MHz, CD3OD) 11.2(s, 1H), 7.99(s, 1H), 7.72(d, 1H), 7.36(d, 1H), 6.65(dd, 2H), 5.31–5.26(m, 1H), 3.82(s, 3H), 2.95–2.87(m, 2H), 2.72–2.65(m, 2H), 2.42(s, 3H), 2.30–2.24(m, 2H), 1.95–1.90(m, 2H) | 354.42/355.4 |
| 53 | 5-(1-Methyl-piperidin-4-yloxy)-1H-pyrrolo[3,2-b]pyridine-3-carboxylic acid (6-methoxy-pyrazin-2-yl)-amide | 1-methylpiperidin-4-yloxy | H | 6-methoxy-pyrazin-2-yl | 1H NMR (400 MHz, CD3OD) 9.14(s, 1H), 8.06(s, 1H), 7.89(s, 1H), 7.76(d, 1H), 6.70(d, 1H), 5.57–5.52(m, 1H), 4.00(s, 3H), 2.68–2.60(m, 4H), 2.35(s, 3H), 2.10–2.03(m, 4H) | 382.43/383.3 |
| 54 | 5-(1-Methyl-piperidin-4-yloxy)-1H-pyrrolo[3,2-b]pyridine-3-carboxylic acid pyridin-4-ylamide | 1-methylpiperidin-4-yloxy | H | pyridin-4-yl | 1H NMR (400 MHz, CD3OD) 8.41(dd, 2H), 8.04(s, 1H), 7.74(d, 1H), 7.67(dd, 2H), 6.69(d, 1H), 5.30–5.25(m, 1H), 2.83–2.75(m, 2H), 2.55–2.48(m, 2H), 2.37(s, 3H), 2.21–2.14(m, 2H), 2.09–2.00(m, 2H) | 351.41/352.4 |

TABLE II-continued

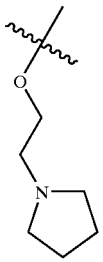

| Cpd. # | Name | R₁ | R₂ | Ar | ¹H NMR | Mass Spec (Calc/Obs. M + 1 or M − 1) |
|---|---|---|---|---|---|---|
| 55 | 5-(2-Diethylamino-ethoxy)-1H-pyrrolo[3,2-b]pyridine-3-carboxylic acid (5-methyl-isoxazol-3-yl)-amide | 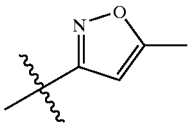 | H | 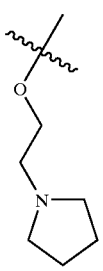 | 1H NMR (400 MHz, CDCl3) 8.01(s, 1H), 7.46(d, 1H), 6.38(d, 1H), 6.30(s, 1H), 4.58(t, 2H), 3.07(t, 2H), 2.80(q, 4H), 2.29(s, 3H), 1.14(t, 6H) | 357.42/358.3 |
| 56 | 5-(2-Diethylamino-ethoxy)-1H-pyrrolo[3,2-b]pyridine-3-carboxylic acid pyridin-2-ylamide | 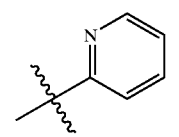 | H | 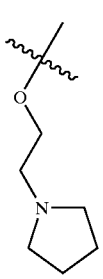 | 1H NMR (400 MHz, CDCl3) 8.38(d, 1H), 8.28(dd, 1h), 8.03 (s, 1h), 7.71–7.67(m, 1H), 7.54(d, 1H), 7.01–6.98(m, 1H), 6.46(d, 1H), 4.78(t, 2H), 3.21(t, 2H), 2.92(q, 4H), 1.20(t, 6H) | 353.43/354.0 |
| 57 | 5-(2-Diethylamino-ethoxy)-1H-pyrrolo[3,2-b]pyridine-3-carboxylic acid (1-methyl-1H-pyrazol-3-yl)-amide | 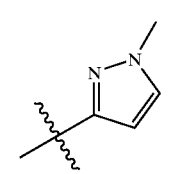 | H | 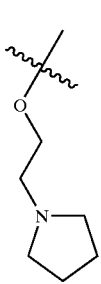 | 1H NMR (400 MHz, CDCl3) 8.00(s, 1H), 7.58(d, 1H), 7.22(d, 1H), 6.77(d, 1H), 6.46(d, 1H), 4.62(t, 2H), 3.78(s, 3H), 3.05(t, 2H), 2.78(q, 4H), 1.11(t, 6H) | 356.43/357.3 |
| 58 | 5-(2-Pyrrolidin-1-yl-ethoxy)-1H-pyrrolo[3,2-b]pyridine-3-carboxylic acid (5-methyl-isoxazol-3-yl)-amide | 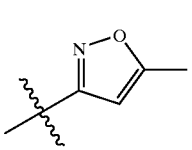 | H | 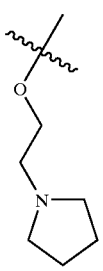 | 1H NMR (400 MHz, CDCl3) 8.00(s, 1H), 7.32(d, 1H), 6.30(s, 1H), 6.25(d, 1H), 4.65(t, 2H), 3.19(t, 2H), 2.90(br s, 4H), 2.29(s, 3H), 1.91(br s, 4H) | 355.4/356.3 |

TABLE II-continued

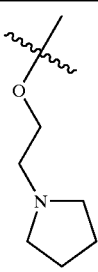

| Cpd. # | Name | R₁ | R₂ | Ar | ¹H NMR | Mass Spec (Calc/Obs. M + 1 or M − 1) |
|---|---|---|---|---|---|---|
| 59 | 5-(2-Pyrrolidin-1-yl-ethoxy)-1H-pyrrolo[3,2-b]pyridine-3-carboxylic acid pyridin-2-ylamide | 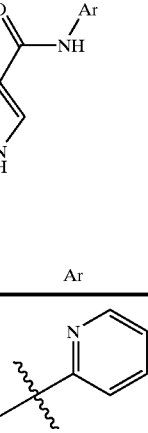 | H | 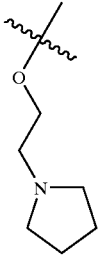 | 1H NMR (400 MHz, CDCl3) 8.26(d, 1H), 8.20(dd, 1H), 7.95 (s, 1H), 7.64(dt, 1H), 7.59(d, 1H), 6.97–6.94(M, 1h), 6.58(D, 1H), 4.72(T, 2h), 3.57(BR S, 1h), 3.19(T, 2h), 2.89(BR S, 4h), 1.86(BR S, 4h) | 351.4/352.3 |
| 60 | 5-(2-Pyrrolidin-1-yl-ethoxy)-1H-pyrrolo[3,2-b]pyridine-3-carboxylic acid (1-methyl-1H-pyrazol-3-yl)-amide | 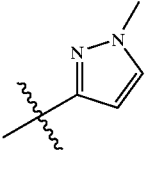 | H | 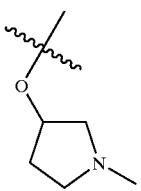 | 1H NMR (400 MHz, CDCl3) 7.96(s, 1h), 7.65(d, 1h), 7.24(d, 1h), 6.68(d, 1h), 6.67(s, 1H), 4.75(t, 2H), 3.75 (9s, 3H), 3.50–3.37(m, 2H), 3.17(br s, 4H), 1.98 (br s, 4H) | 354.4/355.3 |
| 61 | 5-(1-Methyl-pyrrolidin-3-yloxy)-1H-pyrrolo[3,2-b]pyridine-3-carboxylic acid (5-methyl-isoxazol-3-yl)-amide | 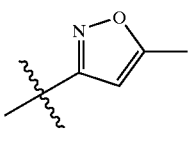 | H | 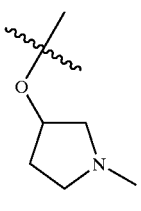 | 1H NMR (400 MHz, CDCl3) 7.967(s, 1H), 7.64(dd, 1H), 6.63 (d, 1H), 6.22(s, 1H), 5.48–5.47(m, 1H), 3.68(br s, 1H), 3.17 (d, 1H), 3.08–3.03(m, 1H), 2.89(dd, 1H), 2.59–2.45(m, 2H), 2.42(s, 3H), 2.21(s, 3H), 2.15–2.07(m, 1H) | 341.37/342.3 |
| 62 | 5-(1-Methyl-pyrrolidin-3-yloxy)-1H-pyrrolo[3,2-b]pyridine-3-carboxylic acid pyridin-2-ylamide | 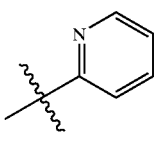 | H | 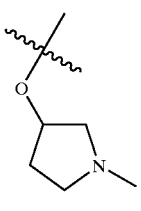 | 1H NMR (400 MHz, CDCl3) 8.22–8.20(m, 2H), 7.92(s, 1H), 7.63–7.58(m, 2H), 6.93–6.90(m, 1H), 6.56(d, 1H), 5.60(br s, 1H), 3.98(br s, 1H), 3.32–3.27(m, 1H), 2.98(d, 1H), 2.94–2.90(m, 1H), 2.64–2.52(m, 2H), 2.38(s, 3H), 2.07–2.04(m, 1H) | 337.38/338.3 |
| 63 | 5-(1-Methyl-pyrrolidin-3-yloxy)-1H-pyrrolo[3,2-b]pyridine-3-carboxylic acid (1-methyl-1H-pyrazol-3-yl)-amide | 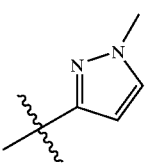 | H | 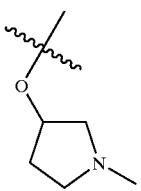 | 1H NMR (400 MHz, CDCl3) 8.01(s, 1H), 7.64(d, 1H), 7.27(s, 1H), 6.79(d, 1H), 6.58(d, 1H), 5.59(br s, 1H), 3.82(s, 3H), 3.24–3.20(m, 1H), 3.08(d, 1H), 3.04–2.99(m, 1H), 2.86–2.67(m, 2H), 2.50(s, 3H), 2.16–2.12(m, 1H) | 340.39/341.3 |

TABLE II-continued

| Cpd. # | Name | R₁ | R₂ | Ar | ¹H NMR | Mass Spec (Calc/Obs. M + 1 or M − 1) |
|---|---|---|---|---|---|---|
| 64 | 5-(2-Dimethylamino-ethoxy)-1H-pyrrolo[3,2-b]pyridine-3-carboxylic acid (5-methyl-isoxazol-3-yl)-amide | –O-CH₂CH₂-NMe₂ | H | 5-methyl-isoxazol-3-yl | 1H NMR (400 MHz, CDCl3) 7.95(s, 1H), 7.59(d, 1H), 6.59(d, 1H), 6.23(s, 1H), 4.49(t, 2H), 3.55(br s, 1H), 2.84(t, 2H), 2.34(s, 6H), 2.22(s, 3H) | 329.39/330.3 |
| 65 | 5-(2-Dimethylamino-ethoxy)-1H-pyrrolo[3,2-b]pyridine-3-carboxylic acid pyridin-2-ylamide | –O-CH₂CH₂-NMe₂ | H | 6-methyl-pyridin-2-yl | 1H NMR (400 MHz, CDCl3) 8.33(d, 1H), 8.27(dd, 1H), 7.97 (s, 1H), 7.69–7.65(m, 1H), 7.47(d, 1H), 7.00–6.96(m, 1H), 6.45(d, 1H), 4.68(t, 2H), 2.91(t, 2H), 2.42(s, 6H) | 325.37/326.3 |
| 66 | 5-(2-Dimethylamino-ethoxy)-1H-pyrrolo[3,2-b]pyridine-3-carboxylic acid (1-methyl-1H-pyrazol-3-yl)-amide | –O-CH₂CH₂-NMe₂ | H | 1-methyl-1H-pyrazol-3-yl | 1H NMR (400 MHz, CDCl3) 7.89(s, 1H), 7.56(d, 1H), 7.19(d, 1H), 6.60(d, 1H), 6.56(d, 1H), 4.51(t, 2H), 4.03(br s, 1H), 3.69(s, 3H), 2.81(t, 2H), 2.30(s, 6H) | 328.38/329.3 |
| 67 | 5-(1-Methyl-azetidin-3-yloxy)-1H-pyrrolo[3,2-b]pyridine-3-carboxylic acid (1-methyl-1H-pyrazol-3-yl)-amide | 1-methyl-azetidin-3-yloxy | H | 1-methyl-1H-pyrazol-3-yl |  | 326.15/327.3 |
| 68 | 5-(3-Dimethylamino-2,2-dimethyl-propoxy)-1H-pyrrolo[3,2-b]pyridine-3-carboxylic acid (1-methyl-1H-pyrazol-3-yl)-amide | 3-dimethylamino-2,2-dimethyl-propoxy | H | 1-methyl-1H-pyrazol-3-yl |  | 370.21/371.4 |

TABLE II-continued

| Cpd. # | Name | R₁ | R₂ | Ar | ¹H NMR | Mass Spec (Calc/Obs. M + 1 or M − 1) |
|---|---|---|---|---|---|---|
| 69 | 5-(3-Dimethylamino-2,2-dimethyl-propoxy)-1H-pyrrolo[3,2-b]pyridine-3-carboxylic acid pyridin-2-ylamide | (CH₃)₂N-CH₂-C(CH₃)₂-CH₂-O- | H | 6-methylpyridin-2-yl | 13C NMR (100 MHz, CDCl3) 163.4, 160.9, 152.7, 148.4, 139.2, 138.1, 131.1, 124.8, 123.6, 119.3, 114.4, 110.6, 107.1, 73.2, 67.9, 49.0, 36.7, 23.7 | 367.2/368.4 |
| 70 | 5-(3-Dimethylamino-propoxy)-1H-pyrrolo[3,2-b]pyridine-3-carboxylic acid (6-methoxy-pyridin-3-yl)-amide | (CH₃)₂N-(CH₂)₃-O- | H | 6-methoxy-pyridin-3-yl |  | 369.18/370.2 |
| 71 | 5-(3-Dimethylamino-propoxy)-1H-pyrrolo[3,2-b]pyridine-3-carboxylic acid (3-fluoro-phenyl)-amide | (CH₃)₂N-(CH₂)₃-O- | H | 3-fluoro-phenyl |  | 356.16/357.2 |
| 72 | 5-(3-Dimethylamino-propoxy)-1H-pyrrolo[3,2-b]pyridine-3-carboxylic acid (3-methyl-isothiazol-5-yl)-amide | (CH₃)₂N-(CH₂)₃-O- | H | 3-methyl-isothiazol-5-yl |  | 359.14/360.2 |

TABLE II-continued

| Cpd. # | Name | R₁ | R₂ | Ar | ¹H NMR | Mass Spec (Calc/Obs. M + 1 or M − 1) |
|---|---|---|---|---|---|---|
| 73 | 5-(3-Dimethylamino-propoxy)-1H-pyrrolo[3,2-b]pyridine-3-carboxylic acid pyrimidin-2-ylamide | dimethylaminopropoxy | H | pyrimidin-2-yl | | 340.16/341.3 |
| 74 | 5-(3-Dimethylamino-propoxy)-1H-pyrrolo[3,2-b]pyridine-3-carboxylic acid (5-methyl-[1,3,4]thiadiazol-2-yl)-amide | dimethylaminopropoxy | H | 5-methyl-[1,3,4]thiadiazol-2-yl | | 360.14/361.2 |
| 75 | 5-(3-Dimethylamino-propoxy)-1H-pyrrolo[3,2-b]pyridine-3-carboxylic acid (6-methyl-pyridin-2-yl)-amide | dimethylaminopropoxy | H | 6-methyl-pyridin-2-yl | | 353.19/354.2 |
| 76 | 5-(3-Dimethylamino-propoxy)-1H-pyrrolo[3,2-b]pyridine-3-carboxylic acid (4,6-dimethyl-pyridin-2-yl)-amide | dimethylaminopropoxy | H | 4,6-dimethyl-pyridin-2-yl | | 367.20/368.3 |

TABLE II-continued

| Cpd. # | Name | R₁ | R₂ | Ar | ¹H NMR | Mass Spec (Calc/Obs. M + 1 or M − 1) |
|---|---|---|---|---|---|---|
| 77 | 5-(3-Dimethylamino-propoxy)-1H-pyrrolo[3,2-b]pyridine-3-carboxylic acid (3-methyl-isoxazol-5-yl)-amide | (dimethylaminopropoxy) | H | 3-methyl-isoxazol-5-yl | | 343.16/344.3 |
| 78 | 5-(3-Dimethylamino-propoxy)-1H-pyrrolo[3,2-b]pyridine-3-carboxylic acid pyridin-2-ylamide | (dimethylaminopropoxy) | H | pyridin-2-yl | 13C NMR (100 MHz, CDCl3) 163.5, 159.8, 152.2, 148.1, 138.9, 138.4, 131.9, 125.2, 124.1, 119.5, 114.6, 109.4, 106.6, 63.4, 55.9, 43.6, 25.3 | 339.17/340.4 |
| 79 | 5-(3-Dimethylamino-propoxy)-1H-pyrrolo[3,2-b]pyridine-3-carboxylic acid (1-methyl-1H-pyrazol-3-yl)-amide | (dimethylaminopropoxy) | H | 1-methyl-1H-pyrazol-3-yl | | 342.18/343.4 |
| 80 | 5-(3-Dimethylamino-propoxy)-1H-pyrrolo[3,2-b]pyridine-3-carboxylic acid (1-ethyl-1H-pyrazol-3-yl)-amide | (dimethylaminopropoxy) | H | 1-ethyl-1H-pyrazol-3-yl | | 356.20/357.3 |

TABLE II-continued

| Cpd. # | Name | R₁ | R₂ | Ar | ¹H NMR | Mass Spec (Calc/Obs. M + 1 or M − 1) |
|---|---|---|---|---|---|---|
| 81 | 5-(3-Dimethylamino-propoxy)-1H-pyrrolo[3,2-b]pyridine-3-carboxylic acid (1-propyl-1H-pyrazol-3-yl)-amide | | H | | | 370.21/371.3 |
| 82 | 5-(3-Dimethylamino-propoxy)-1H-pyrrolo[3,2-b]pyridine-3-carboxylic acid (1-butyl-1H-pyrazol-3-yl)-amide | | H | | | 384.23/385.3 |
| 83 | 5-(3-Diethylamino-propoxy)-1H-pyrrolo[3,2-b]pyridine-3-carboxylic acid (6-ethyl-pyridin-2-yl)-amide | | H | | | 395.23/396.3 |
| 84 | 5-(3-Diethylamino-propoxy)-1H-pyrrolo[3,2-b]pyridine-3-carboxylic acid (6-methyl-pyridin-2-yl)-amide | | H | | | 381.22/382.3 |

TABLE II-continued

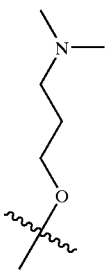

| Cpd. # | Name | R₁ | R₂ | Ar | ¹H NMR | Mass Spec (Calc/Obs. M + 1 or M − 1) |
|---|---|---|---|---|---|---|
| 85 | 5-(3-Diethylamino-propoxy)-1H-pyrrolo[3,2-b]pyridine-3-carboxylic acid (1-methyl-1H-pyrazol-3-yl)-amide | 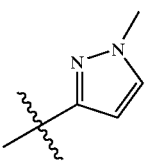 | H | 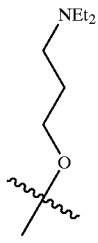 | 1H (400 MHz, CDCl3) 7.95(s, 1H), 7.58(d, 1H, J=8.7Hz), 7.27(d, 1H, J=2.1Hz), 6.79(d, 1H, J=2.1Hz), 6.57(d, 1H, J=8.7Hz), 4.52(t, 2H, J=6.6Hz), 3.82(s, 3H), 2.72(t, 2H, J=7.0Hz), 2.59(q, 4H, J=7.1Hz), 2.08–2.01 (m, 2H), 1.05(t, 6H, J=7.1Hz) | 370.21/371.4 |
| 86 | 5-(3-Diethylamino-propoxy)-1H-pyrrolo[3,2-b]pyridine-3-carboxylic acid pyridin-2-ylamide | 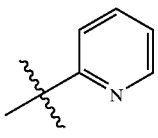 | H | 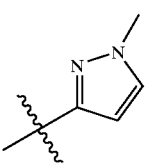 | | 367.20/368.3 |
| 87 | 5-Oxo-4,5-dihydro-1H-pyrrolo[3,2-b]pyridine-3-carboxylic acid (1-methyl-1H-pyrazol-3-yl)-amide | H | H | 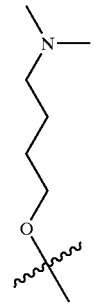 | | 257.25/258.3 |
| 88 | 5-(4-Dimethylamino-butoxy)-1H-pyrrolo[3,2-b]pyridine-3-carboxylic acid pyridin-2-ylamide | 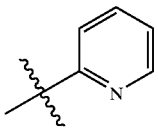 | H | 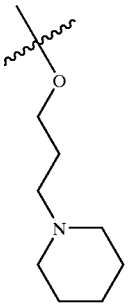 | | 353.19/354.4 |
| 89 | 5-(3-Piperidin-1-yl-propoxy)-1H-pyrrolo[3,2-b]pyridine-3-carboxylic acid (1-methyl-1H-pyrazol-3-yl)-amide | 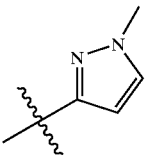 | H | 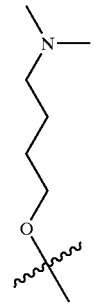 | | 382.21/383.4 |

TABLE II-continued

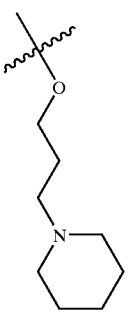

| Cpd. # | Name | R₁ | R₂ | Ar | ¹H NMR | Mass Spec (Calc/Obs. M + 1 or M − 1) |
|---|---|---|---|---|---|---|
| 90 | 5-(3-Piperidin-1-yl-propoxy)-1H-pyrrolo[3,2-b]pyridine-3-carboxylic acid pyridin-2-ylamide | 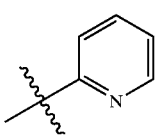 | H | 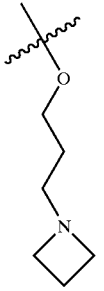 | 1H (400 MHz, CDCl3) 8.41(d, 1H, J=8.3 Hz), 8.31–8.30(m, 1H), 7.90(s, 1H), 7.73–7.68(m, 1H), 7.43(d, 1H, J=8.7 Hz), 7.02–6.99(m, 1H), 6.44(d, 1H, J=8.7Hz), 4.56(t, 2H, J=6.4Hz), 2.65 (t, 2H, J=7.5Hz), 2.52(br s, 2H), 2.19–2.112(m, 2H), 2.08 (br s, 2H), 1.64–1.58 (m, 4H), 1.45(br s, 2H) | 379.20/380.4 |
| 91 | 5-(3-Azetidin-1-yl-propoxy)-1H-pyrrolo[3,2-b]pyridine-3-carboxylic acid (1-methyl-1H-pyrazol-3-yl)-amide | 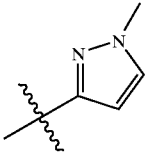 | H | 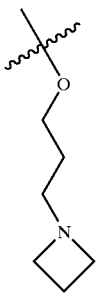 | | 354.18/355.3 |
| 92 | 5-(3-Azetidin-1-yl-propoxy)-1H-pyrrolo[3,2-b]pyridine-3-carboxylic acid pyridin-2-ylamide | 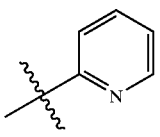 | H |  | | 351.17/352.3 |
| 93 | 5-[2-(1-Methyl-pyrrolidin-2-yl)-ethoxy]-1H-pyrrolo[3,2-b]pyridine-3-carboxylic acid (1-methyl-1H-pyrazol-3-yl)-amide | 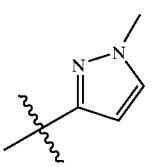 | H | | | 368.20/369.3 |

TABLE II-continued

| Cpd. # | Name | R₁ | R₂ | Ar | ¹H NMR | Mass Spec (Calc/Obs. M + 1 or M − 1) |
|---|---|---|---|---|---|---|
| 94 | 5-[2-(1-Methyl-pyrrolidin-2-yl)-ethoxy]-1H-pyrrolo[3,2-b]pyridine-3-carboxylic acid pyridin-2-ylamide | (1-methylpyrrolidin-2-yl)ethoxy | H | pyridin-2-yl | | 365.19/366.2 |
| 95 | 5-(3-Pyrrol-1-yl-propoxy)-1H-pyrrolo[3,2-b]pyridine-3-carboxylic acid pyridin-2-ylamide | 3-(pyrrol-1-yl)propoxy | H | pyridin-2-yl | | 361.15/362.1 |
| 96 | 5-(3-Pyrrol-1-yl-propoxy)-1H-pyrrolo[3,2-b]pyridine-3-carboxylic acid (1-methyl-1H-pyrazol-3-yl)-amide | 3-(pyrrol-1-yl)propoxy | H | 1-methyl-1H-pyrazol-3-yl | | 364.16/365.2 |
| 97 | 5-[3-(3-Methyl-piperidin-1-yl)-propoxy]-1H-pyrrolo[3,2-b]pyridine-3-carboxylic acid pyridin-2-ylamide | 3-(3-methylpiperidin-1-yl)propoxy | H | pyridin-2-yl | | 393.22/394.2 |

TABLE II-continued

| Cpd. # | Name | R₁ | R₂ | Ar | ¹H NMR | Mass Spec (Calc/Obs. M + 1 or M − 1) |
|---|---|---|---|---|---|---|
| 98 | 5-[3-(3-Methyl-piperidin-1-yl)-propoxy]-1H-pyrrolo[3,2-b]pyridine-3-carboxylic acid (1-methyl-1H-pyrazol-3-yl)-amide | (3-methylpiperidinyl)propoxy | H | 1-methyl-1H-pyrazol-3-yl | | 396.23/397.2 |
| 99 | 5-(3-Hydroxy-3-methyl-butoxy)-1H-pyrrolo[3,2-b]pyridine-3-carboxylic acid (4,6-dimethyl-pyridin-2-yl)-amide | 3-hydroxy-3-methylbutoxy | H | 4,6-dimethylpyridin-2-yl | | 368.18/369.1 |
| 100 | 5-(3-Hydroxy-3-methyl-butoxy)-1H-pyrrolo[3,2-b]pyridine-3-carboxylic acid (6-methyl-pyridin-2-yl)-amide | 3-hydroxy-3-methylbutoxy | H | 6-methylpyridin-2-yl | | 354.17/355.1 |
| 101 | 5-(3-Hydroxy-3-methyl-butoxy)-1H-pyrrolo[3,2-b]pyridine-3-carboxylic acid pyridin-2-ylamide | 3-hydroxy-3-methylbutoxy | H | pyridin-2-yl | 13C (100 MHz, CDCl3) 163.8, 160.4, 152.0, 147.7, 138.8, 132.0, 131.8, 125.2, 123.8, 119.5, 114.8, 110.0, 107.1, 69.9, 63.7, 41.8, 29.3 | 340.15/341.2 |

TABLE II-continued

| Cpd. # | Name | R₁ | R₂ | Ar | ¹H NMR | Mass Spec (Calc/Obs. M + 1 or M − 1) |
|---|---|---|---|---|---|---|
| 102 | 5-(4-Hydroxy-4-methyl-pentyloxy)-1H-pyrrolo[3,2-b]pyridine-3-carboxylic acid pyridin-2-ylamide | (4-hydroxy-4-methylpentyloxy group) | H | pyridin-2-yl | | 354.17/355.2 |
| 103 | 5-[3-(6-Aza-bicyclo[3.2.2]non-6-yl)-propoxy]-1H-pyrrolo[3,2-b]pyridine-3-carboxylic acid (1-methyl-1H-pyrazol-3-yl)-amide | 3-(6-azabicyclo[3.2.2]non-6-yl)propoxy | H | 1-methyl-1H-pyrazol-3-yl | | 422.24/423.2 |
| 104 | 5-[3-(6-Aza-bicyclo[3.2.2]non-6-yl)-propoxy]-1H-pyrrolo[3,2-b]pyridine-3-carboxylic acid pyridin-2-ylamide | 3-(6-azabicyclo[3.2.2]non-6-yl)propoxy | H | pyridin-2-yl | | 419.23/420.2 |

TABLE III

Example 4
Preparation of Radiolabeled Probe Compounds of the Invention

The compounds of the invention are prepared as radiolabeled probes by carrying out their synthesis using precursors comprising at least one atom that is a radioisotope. The radioisotope is preferably selected from of at least one of carbon (preferably $^{14}C$), hydrogen (preferably $^3H$), sulfur (preferably $^{35}S$), or iodine (preferably $^{125}I$). Such radiolabeled probes are conveniently synthesized by a radioisotope supplier specializing in custom synthesis of radiolabeled probe compounds. Such suppliers include Amersham Corporation, Arlington Heights, Ill.; Cambridge Isotope Laboratories, Inc. Andover, Mass.; SRI International, Menlo Park, Cailf.; Wizard Laboratories, West Sacramento, Cailf.; ChemSyn Laboratories, Lexena, Kans.; American Radiolabeled Chemicals, Inc., St. Louis, Mo.; and Moravek Biochemicals Inc., Brea, Calif.

Tritium labeled probe compounds are also conveniently prepared catalytically via platinum-catalyzed exchange in tritiated acetic acid, acid-catalyzed exchange in tritiated trifluoroacetic acid, or heterogeneous-catalyzed exchange with tritium gas. Such preparations are also conveniently carried out as a custom radiolabeling by any of the suppliers listed in the preceding paragraph using the compound of the invention as substrate. In addition, certain precursors may be subjected to tritium-halogen exchange with tritium gas, tritium gas reduction of unsaturated bonds, or reduction using sodium borotritide, as appropriate.

Example 5
Receptor Autoradiography

Receptor autoradiography (receptor mapping) is carried out in vitro as described by Kuhar in sections 8.1.1 to 8.1.9 of Current Protocols in Pharmacology (1998) John Wiley & Sons, New York, using radiolabeled compounds of the invention prepared as described in the preceding Example.

Example 6
Binding Assay

The high affinity and high selectivity of compounds of this invention for the benzodiazepine site of the $GABA_A$ receptor is confirmed using the binding assay described by Thomas and Tallman (J. Bio. Chem. 1981; 156:9838–9842, and J. Neurosci. 1983; 3:433–440).

Rat cortical tissue is dissected and homogenized in 25 volumes (w/v) of Buffer A (0.05 M Tris HCl buffer, pH 7.4 at 4° C.). The tissue homogenate is centrifuged in the cold (4° C.) at 20,000×g for 20 minutes. The supernatant is decanted, the pellet rehomogenized in the same volume of buffer, and centrifuged again at 20,000×g. The supernatant of this centrifugation step is decanted. The resulting pellet may be stored at −20° C. overnight. The pellet is then thawed and resuspended in 25 volumes of Buffer A (original wt/vol), centrifuged at 20,000×g and the supernatant decanted. This wash step is repeated once. The pellet is finally resuspended in 50 volumes of Buffer A.

Incubations contain 100 μl of tissue homogenate, 100 μl of radioligand, (0.5 nM $^3H$-Ro15-1788 [$^3H$-Flumazenil], specific activity 80 Ci/mmol), and test compound or control (see below), and are brought to a total volume of 500 μl with Buffer A. Incubations are carried for 30 minutes at 4° C. and then rapidly filtered through Whatman GFB filters to separate free and bound ligand. Filters are washed twice with fresh Buffer A and counted in a liquid scintillation counter. Nonspecific binding (control) is determined by displacement of $^3H$ Ro15-1788 with 10 μM Diazepam (Research Biochemicals International, Natick, Mass.). Data are collected in triplicate, averaged, and percent inhibition of total specific binding (Total Specific Binding=Total—Nonspecific) is calculated for each compound.

A competition binding curve may obtained with up to 11 points spanning the compound concentration range from $10^{-12}M$ to $10^{-5}M$ obtained per curve by the method described above for determining percent inhibition. $K_i$ values are calculated according the Cheng-Prussof equation. Each of the compounds disclosed in Example 3 was tested in this fashion and each was found to have a $K_i$ of <4 μM. Preferred compounds of the invention exhibit $K_i$ values of less than 100 nM and more preferred compounds of the invention exhibit $K_i$ values of less than 10 nM.

Example 7
Electrophysiology

The following assay is used to determine if a compound of the invention acts as an agonist, an antagonist, or an inverse agonist at the benzodiazepine site of the $GABA_A$ receptor.

Assays are carried out as described in White and Gurley (NeuroReport 6: 1313–1316, 1995) and White, Gurley, Hartnett, Stirling, and Gregory (Receptors and Channels 3: 1–5, 1995) with modifications. Electrophysiological recordings are carried out using the two electrode voltage-clamp technique at a membrane holding potential of −70 mV. *Xenopus Laevis* oocytes are enzymatically isolated and injected with non-polyadenylated cRNA mixed in a ratio of 4:1:4 for α, β and γ subunits, respectively. Of the nine combinations of α, β and γ subunits described in the White et al. publications, preferred combinations are $\alpha_1\beta_2\gamma_2$, $\alpha_2\beta_3\gamma_2$, $\alpha_3\beta_3\gamma_2$, and $\alpha_5\beta_3\gamma_2$. Preferably all of the subunit cRNAs in each combination are human clones or all are rat clones. The sequence of each of these cloned subunits is available from GENBANK, e.g., human $\alpha_1$, GENBANK accession no. X14766, human $\alpha_2$, GENBANK accession no. A28100; human $\alpha_3$, GENBANK accession no. A28102; human $\alpha_5$, GENBANK accession no. A28104; human $\beta_2$, GENBANK accession no. NM 021911; human $_{62\ 3}$, GENBANK accession no. M82919 and accession no. Z20136; human $\gamma_2$, GENBANK accession no. X15376; rat $\alpha_1$, GENBANK accession no. L08490, rat $\alpha_2$, GENBANK accession no. L08491; rat $\alpha_3$, GENBANK accession no. L08492; rat $\alpha_5$, GENBANK accession no. L08494; rat $\beta_2$, GENBANK accession no. X15467; rat $\beta_3$, GENBANK accession no. X15468; and rat $\gamma_2$, GENBANK accession no. L08497. For each subunit combination, sufficient message for each constituent subunit is injected to provide current amplitudes of >10 nA when 1 μM GABA is applied.

Compounds are evaluated against a GABA concentration that evokes <10% of the maximal evokable GABA current (e.g. 1 μM–9 μM). Each oocyte is exposed to increasing concentrations of a compound being evaluated (test compound) in order to evaluate a concentration/effect relationship. Test compound efficacy is calculated as a percent-change in current amplitude: $100*((Ic/I)-1)$, where Ic is the GABA evoked current amplitude observed in the presence of test compound and I is the GABA evoked current amplitude observed in the absence of the test compound.

Specificity of a test compound for the benzodiazepine site is determined following completion of a concentration/effect curve. After washing the oocyte sufficiently to remove previously applied test compound, the oocyte is exposed to GABA+1 μM RO15-1788, followed by exposure to GABA+1 μM RO15-1788+test compound. Percent change due to addition of compound is calculated as described above. Any percent change observed in the presence of RO15-1788 is subtracted from the percent changes in current amplitude observed in the absence of 1 μM RO15-1788. These net values are used for the calculation of average efficacy and $EC_{50}$ values by standard methods. To evaluate average efficacy and $EC_{50}$ values, the concentration/effect data are averaged across cells and fit to the logistic equation.

It is to be understood that the foregoing describes preferred embodiments of the present invention and that modifications may be made therein without departing from the scope of the present invention as set forth in the following claims.

What is claimed is:

1. A compound of the Formula:

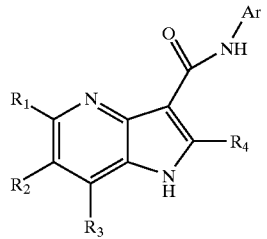

or a pharmaceutically acceptable salt thereof, wherein $R_1$, $R_2$, and $R_3$ are independently A) hydrogen, halogen, halo($C_1$–$C_6$)alkyl, hydroxy, cyano, amino, alkyl, alkoxy, mono- or di-($C_1$–$C_6$)alkylamino, mono- or di-($C_1$–$C_6$)alkylamino($C_1$–$C_6$)alkyl, —C(=O)$NR_{10}R_{11}$, —C(=O)$OR_{10}$, and —OC(=O) $R_{10}$, —C(=O)$R_{10}$, wherein $R_{10}$ and $R_{11}$ are independently hydrogen, $C_1$–$C_6$ alkyl, phenyl, phenyl($C_1$–$C_6$) alkyl, pyridyl, or pyridyl($C_1$–$C_6$)alkyl;

B) haloalkoxy, alkenyl, alkynyl, hydroxyalkyl, —D—$R_{20}$, —E—$R_{35}$, —$C_1$–$C_4$alkyl-D—$R_{20}$, —$C_1$–$C_4$alkyl-O—$R_{20}$, —E—$R_{20}$—G—$R_{30}$, —E—L, —E—$R_{20}$—L, J, —C(=O)—L, or —$C_1$–$C_4$alkyl-J;

where D is —S(O)$_n$—, —S(O)$_n$NH—, —S(O)$_n$NH$_2$, —S(O)$_n$$NR_{30}$—, —NHC(=O)—, —NHC(=O)H, —$NR_{30}$C(=O)—, —$NR_{30}$C(=O)H, —NHS(O) $_n$—, and —$NR_{30}$S(O)$_n$—;

E and G are independently —NH—, —N($C_1$–$C_6$alkyl)—, S, and O;

each $R_{20}$ and $R_{30}$ is independently a ($C_1$–$C_8$)alkyl, ($C_3$–$C_8$)cycloalkyl or ($C_3$–$C_8$)cycloalkyl($C_1$–$C_6$) alkyl group, where each alkyl and cycloalkyl group contains zero or one or more double or triple bonds and where each carbon atom in the $R_{20}$ and $R_{30}$ groups is optionally substituted with one or more substituents independently selected from group C) where C) consists of of oxo, hydroxy, halogen, cyano, amino, $C_1$–$C_6$alkoxy, —NH($C_1$–$C_6$alkyl), —N($C_1$–$C_6$alkyl)($C_1$–$C_6$alkyl), —NHC(=O) ($C_1$–$C_6$alkyl), —N($C_1$–$C_6$alkyl)C(=O) ($C_1$–$C_6$alkyl), —NHS(O)$_n$($C_1$–$C_6$alkyl), —S(O)$_n$ ($C_1$–$C_6$alkyl), —S(O)$_n$NH($C_1$–$C_6$alkyl), —S(O)$_n$N ($C_1$–$C_6$alkyl)($C_1$–$C_6$alkyl), or L, where n is 0, 1, or 2;

each $R_{35}$ is independently a ($C_1$–$C_8$)straight, ($C_1$–$C_8$) branched, ($C_3$–$C_8$)cyclic alkyl or ($C_3$–$C_8$)cycloalkyl ($C_1$–$C_6$)alkyl group, where each alkyl and cycloalkyl group contains zero or one or more double or triple bonds and where each carbon atom in $R_{35}$ is independently substituted with one or substituents selected from group C);

J and L are independently selected at each occurrence from saturated, partially unsaturated, and aromatic rings having from 4 to 7 ring atoms, where 0, 1, or 2 of the ring atoms are oxygen or nitrogen and the remaining ring atoms are carbon, where the rings are unsubstituted or substituted with one or more substituents independently selected from i) halogen, oxo, hydroxy, amino, cyano, $C_1$–$C_6$alkyl, $C_1$–$C_6$alkoxy, $C_1$–$C_6$alkoxy($C_1$–$C_6$alkyl), $C_1$–$C_6$haloalkyl, $C_1$–$C_6$haloalkoxy, and mono- or di-($C_1$–$C_6$)alkylamino; and ii) phenyl, pyridyl, pyrimidyl, and pyrazinyl, each of which is unsubstituted or substituted with from 1 to 3 substituents independently chosen from halogen, hydroxy, amino, cyano, $C_1$–$C_4$alkyl, $C_1$–$C_4$alkoxy, $C_1$–$C_2$haloalkyl, $C_1$–$C_2$haloalkoxy, and mono- or di-($C_1$–$C_4$)alkylamino; with the proviso that J is not phenyl or pyridyl;

wherein at least 1 of $R_1$, $R_2$, and $R_3$ is selected from B) $R_4$ is hydrogen, halogen, or hydroxyl;

Ar represents an aryl, arylalkyl, heteroarylalkyl or heteroaryl group, each aryl having 1 or 2 aromatic rings, 4 to 7 ring atoms in each aromatic ring and where 0, 1, or 2 of the ring atoms are oxygen, nitrogen, or sulfur and the remaining ring atoms are carbon and where each ring is optionally substituted by 1 or more of $R_{40}$; where each $R_{40}$ is independently hydroxy, halogen, cyano, nitro, amino, $XR_{50}$, $C_1$–$C_4$alkyl-$XR_{50}$, or Y;

X is independently selected at each occurrence from the group consisting of a bond, —CH$_2$—, —CHR$_{60}$—, —O—, —C(=O)—, —C(=O)O—, —OC(=O)—, —S(O)$_n$—, —NH—, —NR$_{60}$—, —C(=O)NH—, —C(=O)NR$_{60}$—, —S(O)$_n$NH—, —S(O)$_n$NR$_{60}$—, —NHC(=O)—, —NR$_{60}$C(=O)—, —NHS(O)$_n$—, and —NR$_{60}$S(O)$_n$—;

$R_{50}$ and $R_{60}$ are independently selected at each occurrence from hydrogen, $C_1$–$C_8$ alkyl, $C_3$–$C_8$cycloalkyl, and ($C_3$–$C_8$)cycloalkyl($C_1$–$C_6$) alkyl, where each alkyl and cycloalkyl contains zero or one or more double or triple bonds, and where each carbon atom of the alkyl, cycloalkyl or cycloalkylalkyl is optionally independently substituted with one or more of oxo, hydroxy, halogen, cyano, amino, $C_1$–$C_6$alkoxy, —NH($C_1$–$C_6$alkyl), —N($C_1$–$C_6$alkyl)($C_1$–$C_6$alkyl), —NHC(=O) ($C_1$–$C_6$alkyl), —N($C_1$–$C_6$alkyl)C(=O) ($C_1$–$C_6$alkyl), —NHS(O)$_n$($C_1$–$C_6$alkyl), —S(O)$_n$ ($C_1$–$C_6$alkyl), —S(O)$_n$NH($C_1$–$C_6$alkyl), —S(O)$_n$N ($C_1$–$C_6$alkyl)($C_1$–$C_6$alkyl), and Z, where n is 0, 1, or 2; and Y and Z are independently selected at each occurrence from: saturated, partially unsaturated, or aromatic rings having from 4 to 7 ring atoms, 0, 1, or 2 ring atoms chosen from oxygen and nitrogen, with remaining ring atoms being carbon, wherein Y and Z are unsubstituted or substituted with one or more substituents independently selected from halogen, oxo, hydroxy, amino, cyano, $C_1$–$C_6$alkyl, $C_1$–$C_6$alkoxy, $C_1$–$C_6$alkoxy($C_1$–$C_6$alkyl ), $C_1$–$C_6$haloalkyl, $C_1$–$C_6$haloalkoxy, and mono- or di-($C_1$–$C_6$)alkylamino; and each n is independently 0, 1, or 2.

2. A compound of the Formula:

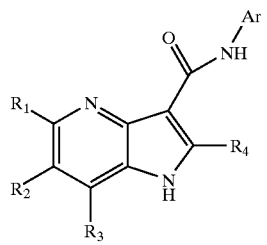

or a pharmaceutically acceptable salt thereof, wherein $R_1$, $R_2$, and $R_3$ are independently chosen from:
A) hydrogen, halogen, halo($C_1$–$C_6$)alkyl, hydroxy, cyano, amino, alkyl, alkoxy, mono- or di-($C_1$–$C_6$)alkylamino, mono- or di-($C_1$–$C_6$)alkylamino($C_1$–$C_6$)alkyl, —C(=O)$NR_{10}R_{11}$, —C(=O)$OR_{10}$, and —OC(=O)$R_{10}$, —C(=O)$R_{10}$, wherein $R_{10}$ and $R_{11}$ are independently chosen from hydrogen, $C_1$–$C_6$ alkyl, phenyl, phenyl($C_1$–$C_6$)alkyl, pyridyl, and pyridyl($C_1$–$C_6$)alkyl;
B) haloalkoxy, alkenyl, alkynyl, hydroxyalkyl, —D—$R_{20}$, —E—$R_{35}$, —$C_1$–$C_4$alkyl-$DpR_{20}$, —$C_1$–$C_4$alkyl-O—$R_{20}$, —E—$R_{20}$—G—$R_{30}$, —E—L, —E—$R_{20}$—L, J, —C(=O)—L, and —$C_1$–$C_4$alkyl-J;
wherein D is —S(O)$_n$—, —S(O)$_n$NH—, —S(O)$_n$NH$_2$, —S(O)$_n$NR$_{30}$—, —NHC(=O)—, —NHC(=O)H, —NR$_{30}$C(=O)—, —NR$_{30}$C(=O)H, —NHS(O)$_n$—, and —NR$_{30}$S(O)$_n$—;
E and G are independently NH, N—$C_1$–$C_6$alkyl, S, and O;
$R_{20}$, $R_{30}$, and $R_{35}$ are independently selected at each occurrence from straight, branched, and cyclic alkyl groups, and (cycloalkyl)alkyl groups, said straight, branched, and cyclic alkyl groups, and (cycloalkyl) alkyl groups consisting of 1 to 8 carbon atoms, and containing zero or one or more double or triple bonds, wherein in $R_{20}$ and $R_{35}$ each of the 1 to 8 carbon atoms may be further substituted with one or more substituent(s) independently selected from group C) and in $R_{35}$ at least one of the 1 to 8 carbon atoms is further substituted by one or more substituent(s) independently selected from group C) wherein group C) consists of: oxo, hydroxy, halogen, cyano, amino, $C_1$–$C_6$alkoxy, —NH($C_1$–$C_6$alkyl), —N($C_1$–$C_6$alkyl)($C_1$–$C_6$alkyl), —NHC(=O) ($C_1$–$C_6$alkyl), —N($C_1$–$C_6$alkyl)C(=O) ($C_1$–$C_6$alkyl), —NHS(O)($C_1$–$C_6$alkyl ), —S(O)$_n$ ($C_1$–$C_6$alkyl), —S(O)$_n$NH($C_1$–$C_6$alkyl), —S(O)$_n$N ($C_1$–$C_6$alkyl)($C_1$–$C_6$alkyl), and L;
J and L are independently selected at each occurrence from: saturated, partially unsaturated, or aromatic rings having from 4 to 7 ring atoms, 0, 1, or 2 ring atoms chosen from oxygen and nitrogen, with remaining ring atoms being carbon, which rings are unsubstituted or substituted with one or more substituents independently selected from: i) halogen, oxo, hydroxy, amino, cyano, $C_1$–$C_6$alkyl, $C_1$–$C_6$alkoxy, $C_1$–$C_6$alkoxy($C_1$–$C_6$alkyl), $C_1$–$C_6$haloalkyl, $C_1$–$C_6$haloalkoxy, and mono- or di-($C_1$–$C_6$)alkylamino and ii)phenyl, pyridyl, pyrimidyl, and pyrazinyl, each of which is unsubstituted or substituted with from 1 to 3 substituents independently chosen from halogen, hydroxy, amino, cyano, $C_1$–$C_4$alkyl, $C_1$–$C_4$alkoxy, $C_1$–$C_2$haloalkyl, $C_1$–$C_2$haloalkoxy, and mono- or di-($C_1$–$C_4$)alkylamino;

$R_4$ is hydrogen, halogen, or hydroxyl;
Ar represents heteroaryl or heteroaryl($C_1$–$C_6$)alkyl, where the heteroaryl is selected from quinolinyl, benzothienyl, indolyl, pryidazinyl, pyazinyl, isoindolyl, isoquinolyl, quinazolinyl, quinoxalinyl, phthalazinyl, imidazolyl, isoxazolyl, pyrazolyl, oxazolyl, thienyl, thiazolyl, indolizinyl, indazolyl, benzothiazolyl, benzimidazolyl, benzofuranyl, benzoisoxolyl, dihydro-benzodioxinyl, furanyl, pyrrolyl, oxadiazolyl, thiadiazolyl, triazolyl, tetrazolyl, oxazolopyridinyl, imidazopyridinyl, isothiazolyl, naphthyridinyl, cinnolinyl, carbazolyl, beta-carbolinyl, isochromanyl, chromanonyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, phenoxazinyl, phenothiazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromanyl, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, and benzothiopyranyl S,S-dioxide, wherein Ar is optionally substituted by 1 or more of $R_{40}$;
$R_{40}$ is independently selected at each occurrence from hydroxy, halogen, cyano, nitro, amino, $XR_{50}$, $C_1$–$C_4$alkyl-$XR_{50}$, and Y;
X is independently selected at each occurrence from the group consisting of a bond, —$CH_2$—, —$CHR_{60}$—, —O—, —C(=O)—, —C(=O)O—, —OC(=O)—, —S(O)$_n$—, —NH—, —NR$_{60}$—, —C(=O)NH—, —C(=O)NR$_{60}$—, —S(O)$_n$NH—, —S(O)$_n$NR$_{60}$—, —NHC(=O)—, —NR$_{60}$C(=O)—, —NHS(O)$_n$—, and —NR$_{60}$S(O)$_n$—;
$R_{50}$ and $R_{60}$ are independently selected at each occurrence from hydrogen, and straight, branched, and cyclic alkyl groups, and (cycloalkyl)alkyl groups, said straight, branched, and cyclic alkyl groups, and (cycloalkyl) alkyl groups consisting of 1 to 8 carbon atoms, and containing zero or one or more double or triple bonds, each of which may be further substituted with one or more substituent(s) independently selected from oxo, hydroxy, halogen, cyano, amino, $C_1$–$C_6$alkoxy, —NH ($C_1$–$C_6$alkyl), —N($C_1$–$C_6$alkyl)($C_1$–$C_6$alkyl), —NHC (=O)($C_1$–$C_6$alkyl), —N($C_1$–$C_6$alkyl)C(=O) ($C_1$–$C_6$alkyl), —NHS(O)$_n$($C_1$–$C_6$alkyl), —S(O)$_n$ ($C_1$–$C_6$alkyl), —S(O)$_n$NH($C_1$–$C_6$alkyl), —S(O)$_n$N ($C_1$–$C_6$alkyl)($C_1$–$C_6$alkyl), and Z;
Y and Z are independently selected at each occurrence from: saturated, partially unsaturated, or aromatic rings having from 4 to 7 ring atoms, 0, 1, or 2 ring atoms chosen from oxygen and nitrogen, with remaining ring atoms being carbon, wherein Y and Z are unsubstituted or substituted with one or more substituents independently selected from halogen, oxo, hydroxy, amino, cyano, $C_1$–$C_6$alkyl, $C_1$–$C_6$alkoxy, $C_1$–$C_6$alkoxy($C_1$–$C_6$alkyl), —$C_1$–$C_6$haloalkyl, $C_1$–$C_6$haloalkoxy, and mono- or di-($C_1$–$C_6$)alkylamino; and n is independently selected at each occurrence from 0, 1, and 2.

3. A compound of the Formula:

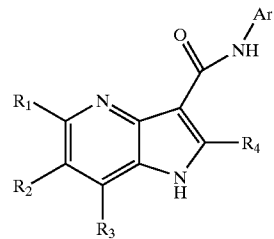

or a pharmaceutically acceptable salt thereof, wherein $R_1$, $R_2$, and $R_3$ are independently chosen from:

A) hydrogen, halogen, halo($C_1$–$C_6$)alkyl, hydroxy, cyano, amino, alkyl, alkoxy, mono- or di-($C_1$–$C_6$)alkylamino, mono- or di-($C_1$–$C_6$)alkylamino($C_1$–$C_6$)alkyl, —C(=O)$NR_{10}R_{11}$, —C(=O)$OR_{10}$, and —OC(=O) $R_{10}$, —C(=O)$R_{10}$, wherein $R_{10}$ and $R_{11}$ are independently chosen from hydrogen, $C_1$–$C_6$ alkyl, phenyl, phenyl($C_1$–$C_6$)alkyl, pyridyl, and pyridyl($C_1$–$C_6$)alkyl;

B) haloalkoxy, alkenyl, alkynyl, hydroxyalkyl, —D—$R_{20}$, —E—$R_{35}$, —$C_1$–$C_4$alkyl-D—$R_{20}$, —$C_1$–$C_4$alkyl-O—$R_{20}$, —E—$R_{20}$—G—$R_{30}$, —E—L, —E—$R_{20}$—L, J, —C(=O)—L, and —$C_1$–$C_4$alkyl-J; wherein D is —S(O)$_n$—, —S(O)$_n$NH—, —S(O)$_n$NH$_2$, —S(O)$_n$NR$_{30}$—, —NHC(=O)—, —NHC(=O)H, —NR$_{30}$C(=O)—, —NR$_{30}$C(=O)H, —NHS(O)$_n$—, and —NR$_{30}$S(O)$_n$—;

E and G are independently NH, N—$C_1$–$C_6$alkyl, S, and O;

$R_{20}$, $R_{30}$, and $R_{35}$ are independently selected at each occurrence from straight, branched, and cyclic alkyl groups, and (cycloalkyl)alkyl groups, said straight, branched, and cyclic alkyl groups, and (cycloalkyl) alkyl groups consisting of 1 to 8 carbon atoms, and containing zero or one or more double or triple bonds, wherein in $R_{20}$ and $R_{35}$ each of the 1 to 8 carbon atoms may be further substituted with one or more substituent(s) independently selected from group C) and in $R_{35}$ at least one of the 1 to 8 carbon atoms is further substituted by one or more substituent(s) independently selected from group C) wherein group C) consists of: oxo, hydroxy, halogen, cyano, amino, $C_1$–$C_6$alkoxy, —NH($C_1$–$C_6$alkyl), —N($C_1$–$C_6$alkyl)($C_1$–$C_6$alkyl), —NHC(=O) ($C_1$–$C_6$alkyl), —N($C_1$–$C_6$alkyl)C(=O) ($C_1$–$C_6$alkyl), —NHS(O)$_n$($C_1$–$C_6$alkyl), —S(O)$_n$ ($C_1$–$C_6$alkyl), —S(O)$_n$NH($C_1$–$C_6$alkyl), —S(O)$_n$N ($C_1$–$C_6$alkyl)($C_1$–$C_6$alkyl), and L;

J and L are independently selected at each occurrence from: saturated, partially unsaturated, or aromatic rings having from 4 to 7 ring atoms, 0, 1, or 2 ring atoms chosen from oxygen and nitrogen, with remaining ring atoms being carbon, which rings are unsubstituted or substituted with one or more substituents independently selected from i) halogen, oxo, hydroxy, amino, cyano, $C_1$–$C_6$alkyl, $C_1$–$C_6$alkoxy, $C_1$–$C_6$alkoxy($C_1$–$C_6$alkyl), $C_1$–$C_6$haloalkyl, $C_1$–$C_6$haloalkoxy, and mono- or di-($C_1$–$C_6$)alkylamino and ii)phenyl, pyridyl, pyrimidyl, and pyrazinyl, each of which is unsubstituted or substituted with from 1 to 3 substituents independently chosen from halogen, hydroxy, amino, cyano, $C_1$–$C_4$alkyl, $C_1$–$C_4$alkoxy, $C_1$–$C_2$haloalkyl, $C_1$–$C_2$haloalkoxy, and mono- or di-($C_1$–$C_4$)alkylamino;

$R_4$ is hydrogen, halogen, or hydroxyl;

Ar represents phenyl, pyridyl, or pyrimidinyl wherein

Ar is optionally substituted by 1 or more of $R_{40}$;

$R_{40}$ is independently selected at each occurrence from hydroxy, halogen, cyano, nitro, amino, $C_1$–$C_6$alkyl, $C_1$–$C_6$alkoxy, $C_1$–$C_6$alkanoyl, $C_3$–$C_7$cycloalkyl, $C_3$–$C_7$cycloalkyl($C_1$–$C_4$)alkyl, $C_3$–$C_7$cycloalkyl-O—, $C_3$–$C_7$cycloalkyl($C_1$–$C_4$)alkoxy-, $C_2$–$C_6$alkenyl, $C_1$–$C_6$alkylthio-, halo($C_1$–$C_6$)alkyl, and halo($C_1$–$C_6$)alkoxy, and Ar is substituted by at least one of —E—$R_{50}$—G—$R_{60}$, —E—$R_{50}$—G—Y, $C_1$–$C_4$alkyl-X$R_{50}$, —NH—$R_{60}$—Y, —(NR$_{50}$)$R_{60}$—Y, and Y;

X is independently selected at each occurrence from the group consisting of —O—, —C(=O)—, —C(=O) O—, —OC(=O)—, —S(O)$_n$—, —NH—, —NR$_{60}$—, —C(=O)NH—, —C(=O)NR$_{60}$—, —S(O)$_n$NH—, —S(O)$_n$NR$_{60}$—, —NHC(=O)—, —NR$_{60}$C(=O)—, —NHS(O)$_n$—, and —NR$_{60}$S(O)$_n$—;

$R_{50}$ and $R_{60}$ are independently selected at each occurrence from:

hydrogen, and straight, branched, and cyclic alkyl groups, and (cycloalkyl)alkyl groups, said straight, branched, and cyclic alkyl groups, and (cycloalkyl) alkyl groups consisting of 1 to 8 carbon atoms, and containing zero or one or more double or triple bonds, which 1 to 8 carbon atoms may be further substituted with one or more substituent(s) independently selected from oxo, hydroxy, halogen, cyano, amino, $C_1$–$C_6$alkoxy, —NH($C_1$–$C_6$alkyl), —N($C_1$–$C_6$alkyl)($C_1$–$C_6$alkyl), —NHC(=O) ($C_1$–$C_6$alkyl), —N($C_1$–$C_6$alkyl)C(=O) ($C_1$–$C_6$alkyl), —NHS(O)$_n$($C_1$–$C_6$alkyl), —S(O)$_n$ ($C_1$–$C_6$alkyl), —S(O)$_n$NH($C_1$–$C_6$alkyl), —S(O)$_n$N ($C_1$–$C_6$alkyl)($C_1$–$C_6$alkyl), and Z;

Y and Z are independently selected at each occurrence from:

saturated, partially unsaturated, or aromatic rings having from 4 to 7 ring atoms, 0, 1, or 2 ring atoms chosen from oxygen and nitrogen, with remaining ring atoms being carbon, wherein Y and Z are unsubstituted or substituted with one or more substituents independently selected from halogen, oxo, hydroxy, amino, cyano, $C_1$–$C_6$alkyl, $C_1$–$C_6$alkoxy, $C_1$–$C_6$alkoxy($C_1$–$C_6$alkyl), $C_1$–$C_6$haloalkyl, $C_1$–$C_6$haloalkoxy, and mono- or di-($C_1$–$C_6$) alkylamino; and n is independently selected at each occurrence from 0, 1, and 2.

4. A compound or salt according to claim 1, wherein

Ar represents an aryl, arylalkyl, heteroaryl, or heteroarylalkyl group, the aryl or heteroaryl of which is selected from phenyl, pyridyl, pyrimidinyl, pyrazinyl, pyrrolyl, imidazolyl, thienyl, thiazolyl, isothiazolyl, oxazolyl [1,3,4]thiadiazolyl, triazolyl, indolyl, quionolinyl, isoquinolinyl benzodioxolyl, benzofuranyl, benzimiazolyl, benzoisoxolyl, and dihydro-benzodioxinyl, and is optionally substituted by one or more of $R_{40}$.

5. A compound or salt according to claim 4, wherein $R_4$ is hydrogen.

6. A compound or salt according to claim 4, wherein $R_1$ is selected from B);

$R_2$ and $R_3$ are independently selected from hydrogen, halogen, $C_1-C_6$haloalkyl, $C_1-C_6$haloalkoxy, hydroxy, cyano, amino, $C_1-C_6$alkyl, $C_1-C_6$alkoxy, and mono- or di-$(C_1-C_6)$alkylamino; and $R_4$ is hydrogen.

7. A compound or salt according to claim 4, wherein $R_1$ is selected from B);

$R_2$ and $R_3$ are independently selected from hydrogen, halogen, $CF_3$, $CHF_2$, $—OCF_3$, hydroxy, cyano, $C_1-C_2$alkyl, $C_1-C_2$alkoxy, and mono- or di-$(C_1-C_2)$alkylamino; and $R_4$ is hydrogen.

8. A compound or salt according to claim 4, wherein $R_1$ is selected from B);

$R_2$ and $R_3$ are independently selected from hydrogen, halogen, methyl and ethyl;

$R_4$ is hydrogen.

9. A compound or salt according to claim 4, wherein:

$R_{40}$ is independently selected at each occurrence from hydroxy, halogen, cyano, amino, $XR_{50}$, $—(C_1-C_4)$alkyl-$XR_{50}$, and Y;

X is independently selected at each occurrence from the group consisting of a bond, $—CH_2—$, $—CHR_{60}—$, $—O—$, $—C(=O)—$, $—S(O)_n—$, $—NH—$, and $—NR_{60}—$;

$R_{50}$ and $R_{60}$ are independently selected at each occurrence from:

hydrogen, and straight, branched, and cyclic alkyl groups, and (cycloalkyl)alkyl groups, said straight, branched, and cyclic alkyl groups, and (cycloalkyl)alkyl groups consisting of 1 to 8 carbon atoms, and containing zero or one or more double or triple bonds, each of which 1 to 8 carbon atoms may be further substituted with one or more substituent(s) independently selected from oxo, hydroxy, halogen, cyano, amino, $C_1-C_6$alkoxy, $—NH(C_1-C_6$alkyl$)$, $—N(C_1-C_6$alkyl$)(C_1-C_6$alkyl$)$, $—NHC(=O)(C_1-C_6$alkyl$)$, $—N(C_1-C_6$alkyl$)C(=O)(C_1-C_6$alkyl$)$, $—NHS(O)_n(C_1-C_6$alkyl$)$, $—S(O)_n(C_1-C_6$alkyl$)$, $—S(O)_nNH(C_1-C_6$alkyl$)$, $—S(O)_nN(C_1-C_6$alkyl$)(C_1-C_6$alkyl$)$, and Z;

Y and Z are independently selected at each occurrence from:

saturated, partially unsaturated, or aromatic rings having from 4 to 7 ring atoms, 0, 1, or 2 ring atoms chosen from oxygen and nitrogen, with remaining ring atoms being carbon, wherein Y and Z are unsubstituted or substituted with one or more substituents independently selected from halogen, oxo, hydroxy, amino, cyano, $C_1-C_6$alkyl, $C_1-C_6$alkoxy, $C_1-C_6$alkoxy$(C_1-C_6$alkyl$)$, $C_1-C_6$haloalkyl, $C_1-C_6$haloalkoxy, and mono- or di-$(C_1-C_6)$alkylamino; and n is independently selected at each occurrence from 0, 1, and 2.

10. A compound or salt according to claim 9 wherein:

$R_1$ is selected from B);

$R_2$ and $R_3$ are independently selected from hydrogen, halogen, methyl and ethyl; and $R_4$ is hydrogen.

11. A compound or salt according to claim 4 wherein:

$R_1$ is selected from B);

$R_2$ and $R_3$ are independently selected from hydrogen, halogen, methyl and ethyl;

$R_4$ is hydrogen; and $R_{40}$ is independently selected at each occurrence from $C_1-C_6$alkyl, $C_1-C_6$alkoxy; halogen, mono or di-$(C_1-C_6)$alkylamino, mono or di-$(C_1-C_6)$alkylamino$(C_1-C_6)$alkoxy, $(C_1-C_6)$alkoxy$(C_1-C_6)$alkyl, and $(C_1-C_6)$alkoxy$(C_1-C_6)$alkoxy.

12. A compound or salt according to claim 4 wherein:

$R_1$ is selected from B);

B) is $—E—R_{35}$, $—C_1-C_4$alkyl-$O—R_{20}$, $—E—R_{20}—G—R_{30}$, $—E—L$, $—E—R_{20}—L$, J, or $—C_1-C_4$alkyl-J;

E and G are independently NH, N$—C_1-C_6$alkyl, or O;

$R_{20}$, $R_{30}$, and $R_{35}$ are independently selected at each occurrence from:

straight, branched, and cyclic alkyl groups, and (cycloalkyl)alkyl groups, said straight, branched, and cyclic alkyl groups, and (cycloalkyl)alkyl groups consisting of 1 to 8 carbon atoms, and containing zero or one or more double or triple bonds, wherein in $R_{20}$ and $R_{35}$ each of which 1 to 8 carbon atoms may be further substituted with one or more substituent(s) independently selected from group C) and in $R_{35}$ at least one of which 1 to 8 carbon atoms is further substituted by one or more substituent(s) independently selected from group C) wherein group C) consists of: oxo, hydroxy, halogen, cyano, amino, $C_1-C_6$alkoxy, $—NH(C_1-C_6$alkyl$)$, $—N(C_1-C_6$alkyl$)(C_1-C_6$alkyl$)$, $—NHC(=O)(C_1-C_6$alkyl$)$, $—N(C_1-C_6$alkyl$)C(=O)(C_1-C_6$alkyl$)$, $—NHS(O)_n(C_1-C_6$alkyl$)$, $—S(O)_n(C_1-C_6$alkyl$)$, $—S(O)_nNH(C_1-C_6$alkyl$)$, $—S(O)_nN(C_1-C_6$alkyl$)(C_1-C_6$alkyl$)$, and L;

J and L are independently selected at each occurrence from:

saturated heterocyclic rings having from 4 to 7 ring atoms, wherein 1 or 2 ring atoms are nitrogen, with remaining ring atoms being carbon, which rings are unsubstituted or substituted with one or more substituents independently selected from halogen, oxo, hydroxy, amino, cyano, $C_1-C_6$alkyl, $C_1-C_6$alkoxy, $C_1-C_6$alkoxy$(C_1-C_6$alkyl$)$, $C_1-C_6$haloalkyl, $C_1-C_6$haloalkoxy, and mono- or di-$(C_1-C_6)$alkylamino; with the proviso that J is not phenyl or pyridyl;

$R_2$ and $R_3$ are independently selected from hydrogen, halogen, methyl and ethyl;

$R_4$ is hydrogen; and $R_{40}$ is independently selected at each occurrence from $C_1-C_6$alkyl, $C_1-C_6$alkoxy; halogen, mono or di-$(C_1-C_6)$alkylamino, mono or di-$(C_1-C_6)$alkylamino$(C_1-C_6)$alkoxy, $(C_1-C_6)$alkoxy$(C_1-C_6)$alkyl, and $(C_1-C_6)$alkoxy$(C_1-C_6)$alkoxy.

13. A compound or salt according to claim 2, wherein

Ar represents an aryl, arylalkyl, heteroaryl, or heteroarylalkyl group, the aryl or heteroaryl of which is selected from piperazinyl, pyrrolyl, imidazolyl, thienyl, thiazolyl, isothiazolyl, oxazolyl [1,3,4]thiadiazolyl, triazolyl, indolyl, quionolinyl, isoquinolinyl benzodioxolyl, benzofuranyl, benzimiazolyl, benzoisoxolyl, and dihydro-benzodioxinyl, and is optionally substituted by one or more of $R_{40}$.

14. A compound or salt according to claim 13, wherein $R_4$ is hydrogen.

15. A compound or salt according to claim 13, wherein
$R_1$ is selected from hydrogen, halogen, $C_1$–$C_6$haloalkyl, $C_1$–$C_6$haloalkoxy, hydroxy, cyano, amino, $C_1$–$C_6$alkyl, $C_1$–$C_6$alkoxy, mono- or di-($C_1$–$C_6$)alkylamino and B);
$R_2$ and $R_3$ are independently selected from hydrogen, halogen, $C_1$–$C_6$haloalkyl, $C_1$–$C_6$haloalkoxy, hydroxy, cyano, amino, $C_1$–$C_6$alkyl, $C_1$–$C_6$alkoxy, and mono- or di-($C_1$–$C_6$)alkylamino; and
$R_4$ is hydrogen.

16. A compound or salt according to claim 13, wherein
$R_1$ is selected from hydrogen, halogen, $C_1$–$C_6$haloalkyl, $C_1$–$C_6$haloalkoxy, hydroxy, cyano, amino, $C_1$–$C_6$alkyl, $C_1$–$C_6$alkoxy, mono- or di-($C_1$–$C_6$)alkylamino and B);
$R_2$ and $R_3$ are independently selected from hydrogen, halogen, $CF_3$, $CHF_2$, —$OCF_3$, hydroxy, cyano, $C_1$–$C_2$alkyl, $C_1$–$C_2$alkoxy, and mono- or di-($C_1$–$C_2$)alkylamino; and
$R_4$ is hydrogen.

17. A compound or salt according to claim 13, wherein
$R_1$ is selected from hydrogen, halogen, $C_1$–$C_6$haloalkyl, $C_1$–$C_6$haloalkoxy, hydroxy, cyano, amino, $C_1$–$C_6$alkyl, $C_1$–$C_6$alkoxy, mono- or di-($C_1$–$C_6$)alkylamino and B);
B) is —E—$R_{35}$, —$C_1$–$C_4$alkyl-O—$R_{20}$, —E—$R_{20}$—G—$R_{30}$, —E—L, —E—$R_{20}$—L, J, or —$C_1$–$C_4$alkyl-J;
E and G are independently NH, N—$C_1$–$C_6$alkyl, or O;
$R_2$ and $R_3$ are independently selected from hydrogen, halogen, methyl and ethyl;
$R_4$ is hydrogen.

18. A compound or salt according to claim 13, wherein:
$R_{40}$ is independently selected at each occurrence from hydroxy, halogen, cyano, amino, $XR_{50}$, —($C_1$–$C_4$)alkyl-$XR_{50}$, and Y;
X is independently selected at each occurrence from the group consisting of a bond, —$CH_2$—, —$CHR_{60}$—, —O—, —C(=O)—, —S(O)$_n$—, —NH—, and —$NR_{60}$—;
$R_{50}$ and $R_{60}$ are independently selected at each occurrence from:
hydrogen, and straight, branched, and cyclic alkyl groups, and (cycloalkyl)alkyl groups, said straight, branched, and cyclic alkyl groups, and (cycloalkyl)alkyl groups consisting of 1 to 8 carbon atoms, and containing zero or one or more double or triple bonds, each of which 1 to 8 carbon atoms may be further substituted with one or more substituent(s) independently selected from oxo, hydroxy, halogen, cyano, amino, $C_1$–$C_6$alkoxy, —NH($C_1$–$C_6$alkyl), —N($C_1$–$C_6$alkyl)($C_1$–$C_6$alkyl), —NHC(=O)($C_1$–$C_6$alkyl), —N($C_1$–$C_6$alkyl)C(=O)($C_1$–$C_6$alkyl), —NHS(O)$_n$($C_1$–$C_6$alkyl), —S(O)$_n$($C_1$–$C_6$alkyl), —S(O)$_n$NH($C_1$–$C_6$alkyl), —S(O)$_n$N($C_1$–$C_6$alkyl)($C_1$–$C_6$alkyl), and Z;
Y and Z are independently selected at each occurrence from:
saturated, partially unsaturated, or aromatic rings having from 4 to 7 ring atoms, 0, 1, or 2 ring atoms chosen from oxygen and nitrogen, with remaining ring atoms being carbon, wherein Y and Z are unsubstituted or substituted with one or more substituents independently selected from halogen, oxo, hydroxy, amino, cyano, $C_1$–$C_6$alkyl, $C_1$–$C_6$alkoxy, $C_1$–$C_6$alkoxy($C_1$–$C_6$alkyl), $C_1$–$C_6$halo alkyl, $C_1$–$C_6$halo alkoxy, and mono- or di-($C_1$–$C_6$)alkyl amino; and
n is independently selected at each occurrence from 0, 1, and 2.

19. A compound or salt according to claim 18 wherein:
$R_1$ is selected from hydrogen, halogen, $C_1$–$C_6$haloalkyl, $C_1$–$C_6$haloalkoxy, hydroxy, cyano, amino, $C_1$–$C_6$alkyl, $C_1$–$C_6$alkoxy, mono- or di-($C_1$–$C_6$)alkylamino and B);
$R_2$ and $R_3$ are independently selected from hydrogen, halogen, methyl and ethyl; and
$R_4$ is hydrogen.

20. A compound or salt according to claim 13 wherein:
$R_1$ is selected from hydrogen, halogen, $C_1$–$C_6$haloalkyl, $C_1$–$C_6$haloalkoxy, hydroxy, cyano, amino, $C_1$–$C_6$alkyl, $C_1$–$C_6$alkoxy, mono- or di-($C_1$–$C_6$)alkylamino and B);
$R_2$ and $R_3$ are independently selected from hydrogen, halogen, methyl and ethyl;
$R_4$ is hydrogen; and
$R_{40}$ is independently selected at each occurrence from $C_1$–$C_6$alkyl, $C_1$–$C_6$alkoxy; halogen, mono or di-($C_1$–$C_6$)alkylamino, mono or di-($C_1$–$C_6$)alkylamino ($C_1$–$C_6$)alkoxy, ($C_1$–$C_6$)alkoxy($C_1$–$C_6$)alkyl, and ($C_1$–$C_6$)alkoxy($C_1$–$C_6$)alkoxy.

21. A compound or salt according to claim 13 wherein:
$R_1$ is selected from hydrogen, halogen, $C_1$–$C_6$haloalkyl, $C_1C_6$haloalkoxy, hydroxy, cyano, amino, $C_1$–$C_6$alkyl, $C_1$–$C_6$alkoxy, mono- or di-($C_1$–$C_6$)alkylamino and B);
B) is —E—$R_{35}$, —$C_1$–$C_4$alkyl-O—$R_{20}$, —E—$R_{20}$—G—$R_{30}$, —E—L, —E—$R_{20}$—L, J, or —$C_1$–$C_4$alkyl-J;
E and G are independently NH, N—$C_1$–$C_6$alkyl, or O;
$R_{20}$, $R_{30}$, and $R_{35}$ are independently selected at each occurrence from:
straight, branched, and cyclic alkyl groups, and (cycloalkyl)alkyl groups, said straight, branched, and cyclic alkyl groups, and (cycloalkyl)alkyl groups consisting of 1 to 8 carbon atoms, and containing zero or one or more double or triple bonds, wherein in $R_{20}$ and $R_{35}$ each of which 1 to 8 carbon atoms may be further substituted with one or more substituent(s) independently selected from group C) and in $R_{35}$ at least one of which 1 to 8 carbon atoms is further substituted by one or more substituent(s) independently selected from group C) wherein group C) consists of: oxo, hydroxy, halogen, cyano, amino, $C_1$–$C_6$alkoxy, —NH($C_1$–$C_6$alkyl), —N($C_1$–$C_6$alkyl)($C_1$–$C_6$alkyl), —NHC(=O)($C_1$–$C_6$alkyl), —N($C_1$–$C_6$alkyl)C(=O)($C_1$–$C_6$alkyl), —NHS(O)$_n$($C_1$–$C_6$alkyl), —S(O)$_n$($C_1$–$C_6$alkyl), —S(O)$_n$NH($C_1$–$C_6$alkyl), —S(O)$_n$N($C_1$–$C_6$alkyl)($C_1$–$C_6$alkyl), and L;
J and L are independently selected at each occurrence from:
saturated heterocyclic rings having from 4 to 7 ring atoms, wherein 1 or 2 ring atoms are nitrogen, with remaining ring atoms being carbon, which rings are unsubstituted or substituted with one or more substituents independently selected from halogen, oxo, hydroxy, amino, cyano, $C_1$–$C_6$alkyl, $C_1$–$C_6$alkoxy, $C_1$–$C_6$alkoxy($C_1$–$C_6$alkyl), $C_1$–$C_6$haloalkyl, $C_1$–$C_6$haloalkoxy, and mono- or di-($C_1$–$C_6$)alkylamino; with the proviso that J is not phenyl or pyridyl;
$R_2$ and $R_3$ are independently selected from hydrogen, halogen, methyl and ethyl;
$R_4$ is hydrogen; and
$R_{40}$ is independently selected at each occurrence from $C_1$–$C_6$alkyl, $C_1$–$C_6$alkoxy; halogen, mono or di- ($C_1$–$C_6$)alkylamino, mono or di-($C_1$–$C_6$)alkylamino ($C_1$–$C_6$)alkoxy, ($C_1$–$C_6$)alkoxy($C_1$–$C_6$)alkyl, and ($C_1$–$C_6$)alkoxy($C_1$–$C_6$)alkoxy.

22. A compound or salt according to claim 3, wherein $R_4$ is hydrogen.

23. A compound or salt according to claim 3, wherein
$R_1$ is selected from hydrogen, halogen, $C_1$–$C_6$haloalkyl, $C_1$–$C_6$haloalkoxy, hydroxy, cyano, amino, $C_1$–$C_6$alkyl, $C_1$–$C_6$alkoxy, and mono- or di-($C_1$–$C_6$)alkylamino and B);
$R_2$ and $R_3$ are independently selected from hydrogen, halogen, $C_1$–$C_6$haloalkyl, $C_1$–$C_6$haloalkoxy, hydroxy, cyano, amino, $C_1C_6$alkyl, $C_1$–$C_6$alkoxy, and mono- or di-($C_1$–$C_6$)alkylamino; and
$R_4$ is hydrogen.

24. A compound or salt according to claim 3, wherein
$R_1$ is selected from hydrogen, halogen, $C_1$–$C_6$haloalkyl, $C_1$–$C_6$haloalkoxy, hydroxy, cyano, amino, $C_1$–$C_6$alkyl, $C_1$–$C_6$alkoxy, and mono- or di-($C_1$–$C_6$)alkylamino;
$R_2$ and $R_3$ are independently selected from hydrogen, halogen, $CF_3$, $CHF_2$, —$OCF_3$, hydroxy, cyano, $C_1$–$C_2$alkyl, $C_1$–$C_2$alkoxy, and mono- or di-($C_1$–$C_2$)alkylamino; and
$R_4$ is hydrogen.

25. A compound or salt according to claim 3, wherein:
Ar is optionally substituted by 1 or more of $R_{40}$;
$R_{40}$ is independently selected at each occurrence from hydroxy, halogen, cyano, amino, $C_1$–$C_6$alkyl, $C_1$–$C_6$alkoxy, halo($C_1$–$C_6$)alkyl, and halo($C_1$–$C_6$) alkoxy, and
Ar is substituted by at least one of —E—$R_{50}$—G—$R_{60}$, —E—$R_{50}$—G—Y, $C_1$–$C_4$alkyl-$XR_{50}$, —NH—$R_{60}$—Y, —($NR_{50}$)$R_{60}$—Y, and Y;
X is independently selected at each occurrence from the group consisting of —O—, —C(=O)—, —C(=O)O—, —OC(=O)—, —S(O)$_n$—, —NH—, —$NR_{60}$—, —C(=O)NH—, —C(=O)$NR_{60}$—, —NHC(=O)—, and —$NR_{60}$C(=O);
$R_{50}$ and $R_{60}$ are independently selected at each occurrence from:
hydrogen, and
straight, branched, and cyclic alkyl groups, and (cycloalkyl)alkyl groups, said straight, branched, and cyclic alkyl groups, and (cycloalkyl)alkyl groups consisting of 1 to 8 carbon atoms, and containing zero or one or more double or triple bonds, each of which 1 to 8 carbon atoms may be further substituted with one or more substituent(s) independently selected from oxo, hydroxy, halogen, cyano, amino, $C_1$–$C_6$alkoxy, —NH($C_1$–$C_6$alkyl), —N($C_1$–$C_6$alkyl)($C_1$–$C_6$alkyl), —NHC(=O)($C_1$–$C_6$alkyl), —N($C_1$–$C_6$alkyl)C(=O)($C_1$–$C_6$alkyl), and Z.

26. A compound or salt according to claim 25, wherein:
$R_1$ is selected from hydrogen, halogen, $C_1$–$C_6$haloalkyl, $C_1$–$C_6$haloalkoxy, hydroxy, cyano, amino, $C_1$–$C_6$alkyl, $C_1$–$C_6$alkoxy, and mono- or di-($C_1$–$C_6$)alkylamino;
$R_2$ and $R_3$ are independently selected from hydrogen, halogen, $CF_3$, $CHF_2$, —$OCF_3$, hydroxy, cyano, $C_1$–$C_2$alkyl, $C_1$–$C_2$alkoxy, and mono- or di-($C_1$–$C_2$)alkylamino; and
$R_4$ is hydrogen.

27. A compound or salt according to claim 25, wherein:
$R_1$ is selected from hydrogen, halogen, $C_1$–$C_6$haloalkyl, $C_1$–$C_6$haloalkoxy, hydroxy, cyano, amino, $C_1$–$C_6$alkyl, $C_1$–$C_6$alkoxy, mono- or di-($C_1$–$C_6$)alkylamino and B);
$R_2$ and $R_3$ are independently selected from hydrogen, halogen, methyl and ethyl; and
$R_4$ is hydrogen.

28. A compound or salt according to claim 1 which is selected from the group consisting of
5-(1-Methyl-piperidin-4-yloxy)-1H-pyrrolo[3,2-b]pyridine-3-carboxylic acid pyridin-2-ylamide;
1H-Pyrrolo[3,2-b]pyridine-3-carboxylic acid (2-fluoro-phenyl)-amide;
1H-Pyrrolo[3,2-b]pyridine-3-carboxylic acid pyridin-2-ylamide;
7-Chloro-1H-pyrrolo[3,2-b]pyridine-3-carboxylic acid (2-fluoro-phenyl)-amide;
6-Methyl-1H-pyrrolo[3,2-b]pyridine-3-carboxylic acid (4-methoxy-phenyl)-amide;
6-Methyl-1H-pyrrolo[3,2-b]pyridine-3-carboxylic acid (5-propoxy-pyridin-2-yl)-amide;
6-Methyl-1H-pyrrolo[3,2-b]pyridine-3-carboxylic acid pyridin-3-ylamide;
5-Methoxy-1H-pyrrolo[3,2-b]pyridine-3-carboxylic acid (2-fluoro-phenyl)-amide;
5-Methoxy-1H-pyrrolo[3,2-b]pyridine-3-carboxylic acid pyridin-2-ylamide;
5-Methoxy-1H-pyrrolo[3,2-b]pyridine-3-carboxylic acid (4-methoxy-phenyl)-amide;
5-Ethylamino-1H-pyrrolo[3,2-b]pyridine-3-carboxylic acid (4-methoxy-phenyl)-amide;
5-Ethylamino-1H-pyrrolo[3,2-b]pyridine-3-carboxylic acid (2-fluoro-phenyl)-amide;
5-Ethoxy-1H-pyrrolo[3,2-b]pyridine-3-carboxylic acid (2-fluoro-phenyl)-amide;
5-Ethoxy-1H-pyrrolo[3,2-b]pyridine-3-carboxylic acid (4-methoxy-phenyl)-amide;
5-Ethoxy-1H-pyrrolo[3,2-b]pyridine-3-carboxylic acid pyridin-2-ylamide;
5-Ethoxy-1H-pyrrolo[3,2-b]pyridine-3-carboxylic acid (5-chloro-pyridin-2-yl)-amide;
5-Ethoxy-1H-pyrrolo[3,2-b]pyridine-3-carboxylic acid (6-bromo-pyridin-3-yl)-amide;
5-Isopropoxy-1H-pyrrolo[3,2-b]pyridine-3-carboxylic acid (3-fluoro-phenyl)-amide;
5-Isopropoxy-1H-pyrrolo[3,2-b]pyridine-3-carboxylic acid (3-fluoro-4-methoxy-phenyl)-amide;
1H-Pyrrolo[3,2-b]pyridine-3-carboxylic acid quinolin-8-ylamide;
1H-Pyrrolo[3,2-b]pyridine-3-carboxylic acid [4-(3-methanesulfonylamino-propoxy)-phenyl]-amide;
1H-Pyrrolo[3,2-b]pyridine-3-carboxylic acid (3-propyl-[1,2,4]thiadiazol-5-yl)-amide;
1H-Pyrrolo[3,2-b]pyridine-3-carboxylic acid (1-methyl-1H-pyrazol-3-yl)-amide;
6-Methyl-1H-pyrrolo[3,2-b]pyridine-3-carboxylic acid (1-propyl-1H-pyrazol-3-yl)-amide;
6-Methyl-1H-pyrrolo[3,2-b]pyridine-3-carboxylic acid pyrazin-2-ylamide;
5-Methoxy-1H-pyrrolo[3,2-b]pyridine-3-carboxylic acid [6-(3-diethylamino-propoxy)-pyridin-3-yl]-amide;
5-Methoxy-1H-pyrrolo[3,2-b]pyridine-3-carboxylic acid (pyridin-2-ylmethyl)-amide;
5-Ethoxy-1H-pyrrolo[3,2-b]pyridine-3-carboxylic acid [6-(3-diethylamino-propoxy)-pyridin-3-yl]-amide;
5-Ethoxy-1H-pyrrolo[3,2-b]pyridine-3-carboxylic acid [4-(2-ethoxy-ethoxy)-phenyl]-amide;

5-Ethoxy-1H-pyrrolo[3,2-b]pyridine-3-carboxylic acid [6-(tetrahydro-furan-3-yloxy)-pyridin-3-yl]-amide;

5-Ethoxy-1H-pyrrolo[3,2-b]pyridine-3-carboxylic acid (3-methyl-isothiazol-5-yl)-amide;

5-Ethoxy-1H-pyrrolo[3,2-b]pyridine-3-carboxylic acid (5-methyl-1H-pyrazol-3-yl)-amide;

5-Ethoxy-1H-pyrrolo[3,2-b]pyridine-3-carboxylic acid (3-methyl-isoxazol-5-yl)-amide;

5-Ethoxy-1H-pyrrolo[3,2-b]pyridine-3-carboxylic acid (5-methyl-isoxazol-3-yl)-amide;

5-Ethoxy-1H-pyrrolo[3,2-b]pyridine-3-carboxylic acid (1-ethyl-1H-pyrazol-3-yl)-amide;

5-Ethoxy-1H-pyrrolo[3,2-b]pyridine-3-carboxylic acid [4-(2-hydroxy-ethyl)-phenyl]-amide;

5-Ethoxy-1H-pyrrolo[3,2-b]pyridine-3-carboxylic acid [4-(2-diethylamino-ethyl)-phenyl]-amide;

5-Ethoxy-1H-pyrrolo[3,2-b]pyridine-3-carboxylic acid (3-hydroxymethyl-phenyl)-amide;

5-Ethoxy-1H-pyrrolo[3,2-b]pyridine-3-carboxylic acid (3-pyrrolidin-1-ylmethyl-phenyl)-amide;

5-Ethoxy-1H-pyrrolo[3,2-b]pyridine-3-carboxylic acid [4-(2-pyrrolidin-1-yl-ethyl)-phenyl]-amide;

5-Isopropoxy-1H-pyrrolo[3,2-b]pyridine-3-carboxylic acid (3-methyl-isothiazol-5-yl)-amide;

5-Isopropoxy-1H-pyrrolo[3,2-b]pyridine-3-carboxylic acid (3-methyl-isoxazol-5-yl)-amide;

5-Isopropoxy-1H-pyrrolo[3,2-b]pyridine-3-carboxylic acid (5-methyl-isoxazol-3-yl)-amide;

5-Isopropoxy-1H-pyrrolo[3,2-b]pyridine-3-carboxylic acid (5-methyl-1H-pyrazol-3-yl)-amide;

5-Isopropoxy-1H-pyrrolo[3,2-b]pyridine-3-carboxylic acid (1-ethyl-1H-pyrazol-3-yl)-amide;

5-(2-Methoxy-ethoxy)-1H-pyrrolo[3,2-b]pyridine-3-carboxylic acid (5-methyl-isoxazol-3-yl)-amide;

5-(2-Methoxy-ethoxy)-1H-pyrrolo[3,2-b]pyridine-3-carboxylic acid (3-methyl-isoxazol-5-yl)-amide;

5-(2-Methoxy-ethoxy)-1H-pyrrolo[3,2-b]pyridine-3-carboxylic acid (3-methyl-isothiazol-5-yl)-amide;

5-(2-Methoxy-ethoxy)-1H-pyrrolo[3,2-b]pyridine-3-carboxylic acid (5-methyl-1H-pyrazol-3-yl)-amide;

5-(1-Methyl-piperidin-4-yloxy)-1H-pyrrolo[3,2-b]pyridine-3-carboxylic acid (5-methyl-isoxazol-3-yl)-amide;

5-(1-Methyl-piperidin-4-yloxy)-1H-pyrrolo[3,2-b]pyridine-3-carboxylic acid pyridin-2-ylamide;

5-(1-Methyl-piperidin-4-yloxy)-1H-pyrrolo[3,2-b]pyridine-3-carboxylic acid (1-methyl-1H-pyrazol-3-yl)-amide;

5-(1-Methyl-piperidin-4-yloxy)-1H-pyrrolo[3,2-b]pyridine-3-carboxylic acid (6-methoxy-pyrazin-2-yl)-amide;

5-(1-Methyl-piperidin-4-yloxy)-1H-pyrrolo[3,2-b]pyridine-3-carboxylic acid pyridin-4-ylamide;

5-(2-Diethylamino-ethoxy)-1H-pyrrolo[3,2-b]pyridine-3-carboxylic acid (5-methyl-isoxazol-3-yl)-amide;

5-(2-Diethylamino-ethoxy)-1H-pyrrolo[3,2-b]pyridine-3-carboxylic acid pyridin-2-ylamide;

5-(2-Diethylamino-ethoxy)-1H-pyrrolo[3,2-b]pyridine-3-carboxylic acid (1-methyl-1H-pyrazol-3-yl)-amide;

5-(2-Pyrrolidin-1-yl-ethoxy)-1H-pyrrolo[3,2-b]pyridine-3-carboxylic acid (5-methyl-isoxazol-3-yl)-amide;

5-(2-Pyrrolidin-1-yl-ethoxy)-1H-pyrrolo[3,2-b]pyridine-3-carboxylic acid pyridin-2-ylamide;

5-(2-Pyrrolidin-1-yl-ethoxy)-1H-pyrrolo[3,2-b]pyridine-3-carboxylic acid (1-methyl-1H-pyrazol-3-yl)-amide;

5-(1-Methyl-pyrrolidin-3-yloxy)-1H-pyrrolo[3,2-b]pyridine-3-carboxylic acid (5-methyl-isoxazol-3-yl)-amide;

5-(1-Methyl-pyrrolidin-3-yloxy)-1H-pyrrolo[3,2-b]pyridine-3-carboxylic acid pyridin-2-ylamide;

5-(1-Methyl-pyrrolidin-3-yloxy)-1H-pyrrolo[3,2-b]pyridine-3-carboxylic acid (1-methyl-1H-pyrazol-3-yl)-amide;

5-(2-Dimethylamino-ethoxy)-1H-pyrrolo[3,2-b]pyridine-3-carboxylic acid (5-methyl-isoxazol-3-yl)-amide;

5-(2-Dimethylamino-ethoxy)-1H-pyrrolo[3,2-b]pyridine-3-carboxylic acid pyridin-2-ylamide;

5-(2-Dimethylamino-ethoxy)-1H-pyrrolo[3,2-b]pyridine-3-carboxylic acid (1-methyl-1H-pyrazol-3-yl)-amide;

5-(1-Methyl-azetidin-3-yloxy)-1H-pyrrolo[3,2-b]pyridine-3-carboxylic acid (1-methyl-1H-pyrazol-3-yl)-amide;

5-(3-Dimethylamino-2,2-dimethyl-propoxy)-1H-pyrrolo[3,2-b]pyridine-3-carboxylic acid (1-methyl-1H-pyrazol-3-yl)-amide;

5-(3-Dimethylamino-2,2-dimethyl-propoxy)-1H-pyrrolo[3,2-b]pyridine-3-carboxylic acid pyridin-2-ylamide;

5-(3-Dimethylamino-propoxy)-1H-pyrrolo[3,2-b]pyridine-3-carboxylic acid (6-methoxy-pyridin-3-yl)-amide;

5-(3-Dimethylamino-propoxy)-1H-pyrrolo[3,2-b]pyridine-3-carboxylic acid (3-fluoro-phenyl)-amide;

5-(3-Dimethylamino-propoxy)-1H-pyrrolo[3,2-b]pyridine-3-carboxylic acid (3-methyl-isothiazol-5-yl)-amide;

5-(3-Dimethylamino-propoxy)-1H-pyrrolo[3,2-b]pyridine-3-carboxylic acid pyrimidin-2-ylamide;

5-(3-Dimethylamino-propoxy)-1H-pyrrolo[3,2-b]pyridine-3-carboxylic acid (5-methyl-[1,3,4]thiadiazol-2-yl)-amide;

5-(3-Dimethylamino-propoxy)-1H-pyrrolo[3,2-b]pyridine-3-carboxylic acid (6-methyl-pyridin-2-yl)-amide;

5-(3-Dimethylamino-propoxy)-1H-pyrrolo[3,2-b]pyridine-3-carboxylic acid (4,6-dimethyl-pyridin-2-yl)-amide;

5-(3-Dimethylamino-propoxy)-1H-pyrrolo[3,2-b]pyridine-3-carboxylic acid (3-methyl-isoxazol-5-yl)-amide;

5-(3-Dimethylamino-propoxy)-1H-pyrrolo[3,2-b]pyridine-3-carboxylic acid pyridin-2-ylamide;

5-(3-Dimethylamino-propoxy)-1H-pyrrolo[3,2-b]pyridine-3-carboxylic acid (1-methyl-1H-pyrazol-3-yl)-amide;

5-(3-Dimethylamino-propoxy)-1H-pyrrolo[3,2-b]pyridine-3-carboxylic acid (1-ethyl-1H-pyrazol-3-yl)-amide;

5-(3-Dimethylamino-propoxy)-1H-pyrrolo[3,2-b]pyridine-3-carboxylic acid (1-propyl-1H-pyrazol-3-yl)-amide;

5-(3-Dimethylamino-propoxy)-1H-pyrrolo[3,2-b]pyridine-3-carboxylic acid (1-butyl-1H-pyrazol-3-yl)-amide;

5-(3-Diethylamino-propoxy)-1H-pyrrolo[3,2-b]pyridine-3-carboxylic acid (6-ethyl-pyridin-2-yl)-amide;

5-(3-Diethylamino-propoxy)-1H-pyrrolo[3,2-b]pyridine-3-carboxylic acid (6-methyl-pyridin-2-yl)-amide;

5-(3-Diethylamino-propoxy)-1H-pyrrolo[3,2-b]pyridine-3-carboxylic acid (1-methyl-1H-pyrazol-3-yl)-amide;

5-(3-Diethylamino-propoxy)-1H-pyrrolo[3,2-b]pyridine-3-carboxylic acid pyridin-2-ylamide;

5-Oxo-4,5-dihydro-1H-pyrrolo[3,2-b]pyridine-3-carboxylic acid (1-methyl-1H-pyrazol-3-yl)-amide;

5-(4-Dimethylamino-butoxy)-1H-pyrrolo[3,2-b]pyridine-3-carboxylic acid pyridin-2-ylamide;

5-(3-Piperidin-1-yl-propoxy)-1H-pyrrolo[3,2-b]pyridine-3-carboxylic acid (1-methyl-1H-pyrazol-3-yl)-amide;

5-(3-Piperidin-1-yl-propoxy)-1H-pyrrolo[3,2-b]pyridine-3-carboxylic acid pyridin-2-ylamide;

5-(3-Azetidin-1-yl-propoxy)-1H-pyrrolo[3,2-b]pyridine-3-carboxylic acid (1-methyl-1H-pyrazol-3-yl)-amide;

5-(3-Azetidin-1-yl-propoxy)-1H-pyrrolo[3,2-b]pyridine-3-carboxylic acid pyridin-2-ylamide;

5-[2-(1-Methyl-pyrrolidin-2-yl)-ethoxy]-1H-pyrrolo[3,2-b]pyridine-3-carboxylic acid (1-methyl-1H-pyrazol-3-yl)-amide;

5-[2-(1-Methyl-pyrrolidin-2-yl)-ethoxy]-1H-pyrrolo[3,2-b]pyridine-3-carboxylic acid pyridin-2-ylamide;

5-(3-Pyrrol-1-yl-propoxy)-1H-pyrrolo[3,2-b]pyridine-3-carboxylic acid pyridin-2-ylamide;

5-(3-Pyrrol-1-yl-propoxy)-1H-pyrrolo[3,2-b]pyridine-3-carboxylic acid (1-methyl-1H-pyrazol-3-yl)-amide;

5-[3-(3-Methyl-piperidin-1-yl)-propoxy]-1H-pyrrolo[3,2-b]pyridine-3-carboxylic acid pyridin-2-ylamide;

5-[3-(3-Methyl-piperidin-1-yl)-propoxy]-1H-pyrrolo[3,2-b]pyridine-3-carboxylic acid (1-methyl-1H-pyrazol-3-yl)-amide;

5-(3-Hydroxy-3-methyl-butoxy)-1H-pyrrolo[3,2-b]pyridine-3-carboxylic acid (4,6-dimethyl-pyridin-2-yl)-amide;

5-(3-Hydroxy-3-methyl-butoxy)-1H-pyrrolo[3,2-b]pyridine-3-carboxylic acid (6-methyl-pyridin-2-yl)-amide;

5-(3-Hydroxy-3-methyl-butoxy)-1H-pyrrolo[3,2-b]pyridine-3-carboxylic acid pyridin-2-ylamide;

5-(4-Hydroxy-4-methyl-pentyloxy)-1H-pyrrolo[3,2-b]pyridine-3-carboxylic acid pyridin-2-ylamide;

5-[3-(6-Aza-bicyclo[3.2.2]non-6-yl)-propoxy]-1H-pyrrolo[3,2-b]pyridine-3-carboxylic acid (1-methyl-1H-pyrazol-3-yl)-amide;

5-[3-(6-Aza-bicyclo[3.2.2]non-6-yl)-propoxy]-1H-pyrrolo[3,2-b]pyridine-3-carboxylic acid pyridin-2-ylamide;

5-(4-Diethylamino-butoxy)-1H-pyrrolo[3,2-b]pyridine-3-carboxylic acid pyridin-2-ylamide;

5-(3-Pyridin-2-yl-propoxy)-1H-pyrrolo[3,2-b]pyridine-3-carboxylic acid (3-methyl-isoxazol-5-yl)-amide;

5-(3-Pyridin-2-yl-propoxy)-1H-pyrrolo[3,2-b]pyridine-3-carboxylic acid (1-ethyl-1H-pyrazol-3-yl)-amide;

5-(3-Pyridin-2-yl-propoxy)-1H-pyrrolo[3,2-b]pyridine-3-carboxylic acid (1-butyl-1H-pyrazol-3-yl)-amide;

5-(3-Pyridin-2-yl-propoxy)-1H-pyrrolo[3,2-b]pyridine-3-carboxylic acid (1-propyl-1H-pyrazol-3-yl)-amide;

5-(3-Pyridin-2-yl-propoxy)-1H-pyrrolo[3,2-b]pyridine-3-carboxylic acid (1-methyl-1H-pyrazol-3-yl)-amide;

5-(3-Pyridin-2-yl-propoxy)-1H-pyrrolo[3,2-b]pyridine-3-carboxylic acid pyridin-2-ylamide;

5-(4-Hydroxy-butoxy)-1H-pyrrolo[3,2-b]pyridine-3-carboxylic acid pyridin-2-ylamide;

5-[3-(4-Methyl-piperazin-1-yl)-propoxy]-1H-pyrrolo[3,2-b]pyridine-3-carboxylic acid pyridin-2-ylamide;

5-[3-(4-Methyl-piperazin-1-yl)-propoxy]-1H-pyrrolo[3,2-b]pyridine-3-carboxylic acid (1-methyl-1H-pyrazol-3-yl)-amide;

5-(3-Morpholin-4-yl-propoxy)-1H-pyrrolo[3,2-b]pyridine-3-carboxylic acid pyridin-2-ylamide;

5-(3-Morpholin-4-yl-propoxy)-1H-pyrrolo[3,2-b]pyridine-3-carboxylic acid (1-methyl-1H-pyrazol-3-yl)-amide;

5-[2-(4-Methyl-piperazin-1-yl)-ethoxy]-1H-pyrrolo[3,2-b]pyridine-3-carboxylic acid pyridin-2-ylamide;

5-[2-(4-Methyl-piperazin-1-yl)-ethoxy]-1H-pyrrolo[3,2-b]pyridine-3-carboxylic acid (1-methyl-1H-pyrazol-3-yl)-amide;

5-(2-Morpholin-4-yl-ethoxy)-1H-pyrrolo[3,2-b]pyridine-3-carboxylic acid pyridin-2-ylamide;

5-(2-Morpholin-4-yl-ethoxy)-1H-pyrrolo[3,2-b]pyridine-3-carboxylic acid (1-methyl-1H-pyrazol-3-yl)-amide; and pharmaceutically acceptable salts thereof.

29. A compound or salt according to claim 1, wherein in an assay of GABA$_A$ receptor binding the compound exhibits an K$_i$ of 100 nanomolar or less.

30. A compound or salt according to claim 1, wherein in an assay of GABA$_A$ receptor binding the compound exhibits an K$_1$ of 10 nanomolar or less.

31. A pharmaceutical composition comprising a compound or salt according to claim 1 together with a pharmaceutically acceptable carrier or excipient.

32. The pharmaceutical composition of claim 31 wherein the pharmaceutical composition is formulated as an injectible fluid, an aerosol, a cream, a gel, a pill, a capsule, a syrup, or a transdermal patch.

33. A method for the treatment of anxiety, depression, a sleep disorder, attention deficit disorder, or Alzheimer's dementia, comprising administering to a patient in need of such treatment a therapeutically effective amount of a compound or salt according to claim 1.

34. A packaged pharmaceutical preparation comprising the pharmaceutical composition of claim 31 in a container and instructions for using the composition to treat a patient suffering from anxiety, depression, a sleep disorder, attention deficit disorder, Alzheimer's dementia, or short-term memory loss.

35. The use of a compound or salt according to any one of claim 1 for the manufacture of a medicament for the treatment of anxiety, depression, a sleep disorder, an attention deficit disorder, Alzheimer's dementia, or short-term memory loss.

36. A compound of the formula

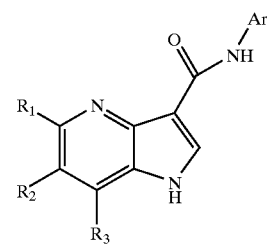

or a pharmaceutically acceptable salt thereof, wherein

R$_1$ is amino(C$_1$–C$_6$)alkoxy, mono(C$_1$–C$_3$)alkylamino(C$_1$–C$_6$)alkoxy, di (C$_1$–C$_3$)alkylamino(C$_1$–C$_6$)alkoxy, pyridyl(C$_1$–C$_6$)alkoxy, hydroxy(C$_1$–C$_6$)alkoxy, ($C_1$–$C_4$)alkoxy($C_1$–$C_6$)alkoxy, piperazinyl($C_1$–$C_6$) alkoxy wherein the piperazinyl group is optionally substituted with ($C_1$–$C_6$)alkyl, morpholinyl($C_1$–$C_6$) alkoxy, or thiomorpholinyl($C_1$–$C_6$)alkoxy;

$R_2$ and $R_3$ are independently selected from H, ($C_1$–$C_6$) alkyl, halogen or ($C_1$–$C_6$)alkoxy;

Ar is pyridyl, isoxazolyl, oxazolyl, thiazolyl, isothiazolyl, pyrazolyl, pyrimidyl, or pyridazinyl, each of which is unsubstituted or substituted with 1, 2, or 3 groups that are independently ($C_1$–$C_6$)alkyl, ($C_1$–$C_6$)alkoxy, halogen, $OCF_3$, or $CF_3$.

37. A compound according to claim 36, wherein $R_1$ is amino($C_1$–$C_4$)alkoxy, mono($C_1$–$C_4$)alkylamino ($C_1$–$C_4$)alkoxy, di($C_1$–$C_4$)alkylamino($C_1$–$C_4$)alkoxy, pyridyl($C_1$–$C_4$)alkoxy, hydroxy($C_1$–$C_4$)alkoxy, piperazinyl($C_1$–$C_4$)alkoxy wherein the piperazinyl group is optionally substituted with ($C_1$–$C_4$)alkyl, or morpholinyl($C_1$–$C_6$)alkoxy.

38. A compound according to claim 37, wherein $R_2$ and $R_3$ are independently selected from H, ($C_1$–$C_4$) alkyl, halogen or ($C_1$–$C_4$)alkoxy, provided that at least one of $R_2$ and $R_3$ is H; and Ar is pyridyl, isoxazolyl, oxazolyl, pyrazolyl, pyrimidyl, or pyridazinyl, each of which is unsubstituted or substituted with 1, 2, or 3 groups that are independently alkyl, alkoxy, halogen, $OCF_3$, or $CF_3$.

39. A compound according to claim 38, wherein $R_1$ is amino($C_1$–$C_4$)alkoxy, mono($C_1$–$C_4$)alkylamino ($C_1$–$C_4$)alkoxy, di($C_1$–$C_4$)alkylamino($C_1$–$C_4$)alkoxy, pyridyl($C_1$–$C_4$)alkoxy, hydroxy($C_1$–$C_4$)alkoxy, piperazinyl($C_1$–$C_4$)alkoxy wherein the piperazinyl group is optionally substituted with ($C_1$–$C_4$)alkyl, or morpholinyl($C_1$–$C_6$)alkoxy;

$R_2$ and $R_3$ are independently selected from H, ($C_1$–$C_4$) alkyl, or ($C_1$–$C_4$)alkoxy, provided that at least one of $R_2$ and $R_3$ is H; and Ar is pyridyl, isoxazolyl, oxazol-5-yl, pyrazolyl, pyrimidyl, or pyridazinyl, each of which is unsubstituted or substituted with 1, 2, or 3 groups that are independently ($C_1$–$C_4$)alkyl, ($C_1$–$C_4$)alkoxy, halogen, $OCF_3$, or $CF_3$.

40. A compound according to claim 39, wherein $R_1$ is amino($C_1$–$C_4$)alkoxy, mono($C_1$–$C_4$)alkylamino ($C_1$–$C_4$)alkoxy, di ($C_1$–$C_4$)alkylamino($C_1$–$C_4$)alkoxy, pyridyl($C_1$–$C_4$)alkoxy, hydroxy($C_1$–$C_4$)alkoxy, piperazinyl($C_1$–$C_4$)alkoxy wherein the piperazinyl group is optionally substituted with ($C_1$–$C_4$)alkyl, or morpholinyl($C_1$–$C_4$)alkoxy;

$R_2$ and $R_3$ are independently selected from H, and ($C_1$–$C_4$)alkyl, provided that at least one of $R_2$ and $R_3$ is H; and Ar is pyrid-2-yl, isoxazol-5-yl, oxazol-5-yl, pyrazol-3-yl, pyrimid-2-yl, or pyridazin-3-yl, each of which is unsubstituted or substituted with 1, or 2 groups that are independently ($C_1$–$C_4$)alkyl, ($C_1$–$C_4$)alkoxy, or halogen.

41. A compound according to claim 36, wherein $R_1$ is amino($C_2$–$C_4$)alkoxy, mono($C_1$–$C_4$)alkylamino ($C_2$–$C_4$)alkoxy, di($C_1$–$C_4$)alkylamino($C_2$–$C_4$)alkoxy, pyridyl($C_2$–$C_4$)alkoxy, hydroxy($C_2$–$C_4$)alkoxy, piperazinyl($C_2$–$C_4$)alkoxy wherein the piperazinyl group is optionally substituted with ($C_1$–$C_4$)alkyl, or morpholinyl($C_2$–$C_4$)alkoxy;

$R_2$ is H or methyl; and $R_3$ is H.

42. A compound according to claim 1, where $R_1$ is amino($C_1$–$C_6$)alkoxy, mono($C_1$–$C_3$)alkylamino ($C_1$–$C_6$)alkoxy, di($C_1$–$C_3$)alkylamino($C_1$–$C_6$)alkoxy, pyridyl($C_1$–$C_6$)alkoxy, hydroxy($C_1$–$C_6$)alkoxy, ($C_1$–$C_4$)alkoxy($C_1$–$C_6$)alkoxy, piperazinyl($C_1$–$C_6$) alkoxy wherein the piperazinyl group is optionally substituted with ($C_1$–$C_6$)alkyl, morpholinyl($C_1$–$C_6$) alkoxy, or thiomorpholinyl($C_1$–$C_6$)alkoxy;

$R_2$ and $R_3$ are independently selected from H, ($C_1$–$C_6$) alkyl, halogen or ($C_1$–$C_6$)alkoxy.

43. A compound according to claim 42, wherein $R_1$ is amino($C_1$–$C_4$)alkoxy, mono($C_1$–$C_4$)alkylamino ($C_1$–$C_4$)alkoxy, di($C_1$–$C_4$)alkylamino($C_1$–$C_4$)alkoxy, pyridyl($C_1$–$C_4$)alkoxy, hydroxy($C_1$–$C_4$)alkoxy, piperazinyl($C_1$–$C_4$)alkoxy wherein the piperazinyl group is optionally substituted with ($C_1$–$C_4$)alkyl, or morpholinyl($C_1$–$C_6$)alkoxy.

44. A compound according to claim 2, where $R_1$ is amino($C_1$–$C_6$)alkoxy, mono($C_1$–$C_3$)alkylamino ($C_1$–$C_6$)alkoxy, di($C_1$–$C_3$)alkylamino($C_1$–$C_6$)alkoxy, pyridyl($C_1$–$C_6$)alkoxy, hydroxy($C_1$–$C_6$)alkoxy, ($C_1$–$C_4$)alkoxy($C_1$–$C_6$)alkoxy, piperazinyl($C_1$–$C_6$) alkoxy wherein the piperazinyl group is optionally substituted with ($C_1$–$C_6$)alkyl, morpholinyl($C_1$–$C_6$) alkoxy, or thiomorpholinyl($C_1$–$C_6$)alkoxy;

$R_2$ and $R_3$ are independently selected from H, ($C_1$–$C_6$) alkyl, halogen or ($C_1$–$C_6$)alkoxy.

45. A compound according to claim 44, wherein $R_1$ is amino($C_1$–$C_4$)alkoxy, mono($C_1$–$C_4$)alkylamino ($C_1$–$C_4$)alkoxy, di($C_1$–$C_4$)alkylamino($C_1$–$C_4$)alkoxy, pyridyl($C_1$–$C_4$)alkoxy, hydroxy($C_1$–$C_4$)alkoxy, piperazinyl($C_1$–$C_4$)alkoxy wherein the piperazinyl group is optionally substituted with ($C_1$–$C_4$)alkyl, or morpholinyl($C_1$–$C_6$)alkoxy.

46. A compound according to claim 3, where $R_1$ is amino($C_1$–$C_6$)alkoxy, mono($C_1$–$C_3$)alkylamino ($C_1$–$C_6$)alkoxy, di($C_1$–$C_3$)alkylamino($C_1$–$C_6$)alkoxy, pyridyl($C_1$–$C_6$)alkoxy, hydroxy($C_1$–$C_6$)alkoxy, ($C_1$–$C_4$)alkoxy($C_1$–$C_6$)alkoxy, piperazinyl($C_1$–$C_6$) alkoxy wherein the piperazinyl group is optionally substituted with ($C_1$–$C_6$)alkyl, morpholinyl($C_1$–$C_6$) alkoxy, or thiomorpholinyl($C_1$–$C_6$)alkoxy;

$R_2$ and $R_3$ are independently selected from H, ($C_1$–$C_6$) alkyl, halogen or ($C_1$–$C_6$)alkoxy.

47. A compound according to claim 46, wherein $R_1$ is amino($C_1$–$C_4$)alkoxy, mono($C_1$–$C_4$)alkylamino ($C_1$–$C_4$)alkoxy, di($C_1$–$C_4$)alkylamino($C_1$–$C_4$)alkoxy, pyridyl($C_1$–$C_4$)alkoxy, hydroxy($C_1$–$C_4$)alkoxy, piperazinyl($C_1$–$C_4$)alkoxy wherein the piperazinyl group is optionally substituted with ($C_1$–$C_4$)alkyl, or morpholinyl($C_1$–$C_6$)alkoxy.

48. A compound or salt according to claim 2, wherein in an assay of $GABA_A$ receptor binding the compound exhibits an $K_i$ of 100 nanomolar or less.

49. A compound or salt according to claim 2, wherein in an assay of $GABA_A$ receptor binding the compound exhibits an $K_i$ of 10 nanomolar or less.

50. A pharmaceutical composition comprising a compound or salt according to claim 2 together with a pharmaceutically acceptable carrier or excipient.

51. A method for the treatment of anxiety, depression, a sleep disorder, attention deficit disorder, or Alzheimer's dementia, comprising administering to a patient in need of such treatment a therapeutically effective amount of a compound or salt according to claim 2.

52. A method for improving short term memory in a patient, comprising the step of administering to a patient a therapeutically effective amount of a compound or salt according to claim 2.

53. A compound or salt according to claim 3, wherein in an assay of $GABA_A$ receptor binding the compound exhibits an $K_i$ of 100 nanomolar or less.

54. A compound or salt according to claim 3, wherein in an assay of $GABA_A$ receptor binding the compound exhibits an $K_i$ of 10 nanomolar or less.

55. A pharmaceutical composition comprising a compound or salt according to claim 3 together with a pharmaceutically acceptable carrier or excipient.

56. A method for the treatment of anxiety, depression, a sleep disorder, attention deficit disorder, or Alzheimer's dementia, comprising administering to a patient in need of such treatment a therapeutically effective amount of a compound or salt according to claim 3.

57. A method for improving short term memory in a patient, comprising the step of administering to a patient a therapeutically effective amount of a compound or salt according to claim 3.

58. A method for improving short term memory in a patient, comprising the step of administering to a patient a therapeutically effective amount of a compound or salt according to claim 1.

* * * * *